(12) United States Patent
Cuff et al.

(10) Patent No.: US 9,879,200 B2
(45) Date of Patent: Jan. 30, 2018

(54) LUBRICATING COMPOSITIONS AND METHODS FOR THE USE THEREOF

(71) Applicant: Ingevity South Carolina, LLC, North Charleston, SC (US)

(72) Inventors: Thomas J. Cuff, Charleston, SC (US); James L. Bowers, Goose Creek, SC (US); Eric J. Olivier, Charleston, SC (US); Kejian Yao, Ladson, SC (US)

(73) Assignee: Ingevity South Carolina, LLC, North Charleston, SC (US)

( * ) Notice: Subject to any disclaimer, the term of this patent is extended or adjusted under 35 U.S.C. 154(b) by 0 days.

(21) Appl. No.: 15/294,342

(22) Filed: Oct. 14, 2016

(65) Prior Publication Data

US 2017/0107440 A1    Apr. 20, 2017

Related U.S. Application Data

(60) Provisional application No. 62/242,100, filed on Oct. 15, 2015.

(51) Int. Cl.

| C10M 129/76 | (2006.01) |
|---|---|
| B05D 1/02 | (2006.01) |
| B05D 1/18 | (2006.01) |
| B05D 1/28 | (2006.01) |
| B05D 1/30 | (2006.01) |
| B05D 7/14 | (2006.01) |
| C07C 69/608 | (2006.01) |
| C10M 173/00 | (2006.01) |

(52) U.S. Cl.
CPC ............. *C10M 129/76* (2013.01); *B05D 1/02* (2013.01); *B05D 1/18* (2013.01); *B05D 1/28* (2013.01); *B05D 1/30* (2013.01); *B05D 7/14* (2013.01); *C07C 69/608* (2013.01); *C10M 173/00* (2013.01); *C07C 2601/16* (2017.05); *C10M 2207/288* (2013.01); *C10N 2230/18* (2013.01); *C10N 2240/40* (2013.01)

(58) Field of Classification Search
CPC .............. C10M 129/76; C10M 173/00; C10M 2207/288; C10N 2230/18; C10N 2240/40; B05D 1/02; B05D 1/18; B05D 1/28; B05D 1/30; B05D 7/14; C07C 69/608; C07C 2601/16

See application file for complete search history.

(56) References Cited

U.S. PATENT DOCUMENTS

| 3,899,476 | A | * | 8/1975 | Ward | ................... | C09F 1/04 |
|---|---|---|---|---|---|---|
| | | | | | | 560/127 |
| 4,394,126 | A | * | 7/1983 | Wilson | ............... | D06M 13/165 |
| | | | | | | 252/8.84 |
| 4,670,168 | A | * | 6/1987 | Laemmle | ............. | C10M 173/02 |
| | | | | | | 508/512 |
| 4,753,743 | A | * | 6/1988 | Sech | ................... | B05D 5/08 |
| | | | | | | 508/312 |

(Continued)

FOREIGN PATENT DOCUMENTS

| EP | 2121802 | 10/2010 |
|---|---|---|
| JP | 54-074845 A | 6/1979 |

*Primary Examiner* — James Goloboy
(74) *Attorney, Agent, or Firm* — Bryan D. Zerhusen; Locke Lord, LLC

(57) ABSTRACT

Disclosed herein are lubricating compositions and methods of use of the same, including for, e.g., use in metalworking operations.

20 Claims, 10 Drawing Sheets

(56) References Cited

U.S. PATENT DOCUMENTS

| | | | | |
|---|---|---|---|---|
| 4,784,796 A | * | 11/1988 | Treybig | C09K 8/54 |
| | | | | 106/14.13 |
| 4,846,986 A | * | 7/1989 | Trivett | C10M 173/02 |
| | | | | 508/283 |
| 5,021,173 A | | 6/1991 | Waddoups | |
| 5,555,756 A | * | 9/1996 | Fischer | B21B 45/0263 |
| | | | | 508/433 |
| 6,420,578 B1 | * | 7/2002 | Cawthorne | A61K 8/361 |
| | | | | 554/156 |
| 2003/0134757 A1 | * | 7/2003 | Milbrath | C10M 105/52 |
| | | | | 508/463 |

* cited by examiner

LUBRICATING COMPOSITIONS AND METHODS FOR THE USE THEREOF

CROSS-REFERENCE TO RELATED APPLICATIONS

This application claims the benefit of U.S. Provisional Patent Application 62/242,100, filed: Oct. 15, 2015, titled, "Lubricating Compositions and Methods for the Use Thereof", which is incorporated herein by reference.

FIELD OF THE INVENTION

This invention relates to compositions and methods of use thereof for lubrication.

BACKGROUND

Lubricating fluids facilitate the reduction of friction (i.e. lubricate), remove heat (i.e. cool), flush away impurities, preserve or improve surface quality, and protect, e.g., tools and machine parts from damage, wear and corrosion as far as possible. In addition to the functions described above, ideal lubricating fluids have the following desirable functions and properties: inhibit corrosion, low foam formation, low toxicity, microbial resistant, waste treatment friendly, biodegradable, and non-objectionable odor.

For example, lubricating fluids are frequently used in metal working processes, e.g., cutting, grinding, forming, lapping, drawing, forming, pressing, punching, rolling, stamping, etc. Metalworking fluids are often straight oil (vegetable or animal oil or fat, a mineral oil, synthetic oil or a mixture thereof) or water-based fluids. Water-based metalworking fluids include soluble oils, which contain less than 2% by weight of water; semi-synthetic fluids, which contain 10-60% by weight of water; synthetic fluids, which are petroleum oil-free and can contain any water-soluble lubricity additive; and neo-synthetic fluids, which use vegetable oil and/or animal oil instead of petroleum and may contain an emulsifier, corrosion inhibitors, alkanolamine, and water. Metalworking fluids may also include agents, for example, an oiliness improver, an extreme pressure agent, a corrosion inhibitor (e.g. a rust preventative), a surfactant, a preservative, an antioxidant, etc.

Petroleum oil rich metalworking fluids are utilized in nearly 80% of metalworking operations. Petroleum based metalworking fluids, however, have several drawbacks, for example: (1) poor heat conductivity and therefore, limited ability to cool; (2) misting results in petroleum residues that are difficult to remove; (3) the emulsion stability is often effected by water hardness; and (4) not environmentally friendly and therefore, result in disposal difficulties.

Amine-containing metalworking fluids are being employed because the amines (e.g. alkanolamines) increase bio-resistance, corrosion protection, and emulsion stability. Effective water-based metalworking fluids are difficult to formulate without employing amines. However, amines can be very toxic. Furthermore, synthetic petroleum oil-free (i.e. water-based) metalworking fluids currently on the market have limited lubricity and stability. As such, there is a need for metalworking fluids that are effective lubricants, which are stable for an extended period of time, and contain less hazardous compounds (e.g. reduced amine content).

DIACID 1550 is often employed in lubricating fluids because it is a co-emulsifier that inhibits corrosion (extends machinery life), has lower bioactivity (prolongs fluid life), and has increased hard water tolerance compared to mixed and fatty acids. As such, employing DIACID 1550 results fewer additives in the lubricating fluid because it functions to lubricate, prevent corrosion, co-emulsifies, etc. However, DIACID 1550 is limited in its hard water tolerance (i.e. stability in hard water), and produces foam when utilized in metalworking fluids.

Therefore, there exists a need to for lubricating fluids that have increased stability (i.e., longer shelf-life), performance in hard water, suitable lubricity, and reduced foam formation during use, e.g., metalworking.

SUMMARY

The present description relates to the surprising and unexpected discovery of agents that provide superior lubrication and hard water tolerance (i.e. stable in hard water), in a non-foaming or low foaming composition. In particular, the present description discloses lubricating compounds and compositions comprising the same. The compounds described herein include partial esters of a compound derived from the Diels-Alder reaction of a diene, e.g., a conjugated fatty acid, and an acid precursor dienophile. The resulting half-esters as described herein demonstrate at least one of increased stability (i.e., longer shelf life), better performance in hard water, lubricity, and reduced foam formation during use. As such, the lubricating compositions as described herein are suitable for numerous applications, including mechanical processes such as metalworking.

In certain embodiments, the diene is a conjugated fatty acid (substituted or unsubstituted).

In certain embodiments the dienophile can be an acrylic acid or an acrylic acid ester. In certain other embodiments the dienophile can be maleic anhydride or fumaric acid or a fumaric acid mono or diester. In certain embodiments, the compound derived from the Diels-Alder reaction of a diene, e.g., a conjugated fatty acid, and an acid precursor dienophile is DIACID 1550, which is derived from the reaction of a fatty acid and acrylic acid.

In certain embodiments, the lubricating compound comprises or consists essentially of a DIACID 1550 partial or half ester. The DIACID 1550 partial ester can be derived from a reaction product of DIACID 1550 and an alcohol. In an embodiment, the lubricating compound is a partial ester of DIACID 1550 and at least one of n-Pentanol, 1-Dodecanol, or 2-ethyl-1-hexanol.

In another aspect, the description provides lubricating compositions comprising a compound as described herein. The lubricating compositions described herein are useful for a variety of applications including, e.g., as a lubricant in mechanical processes or machines such as metalworking.

In a certain embodiments described herein, the composition is a semi-synthetic lubricating fluid. In an exemplary embodiment, the lubricating fluid is a metalworking fluid. The semi-synthetic lubricating fluid can be optimized with a coupling solvent, e.g. tripropylene glycol methyl ether or diethylene glycol monobutyl ether. In another embodiment of the present description, the composition is a synthetic lubricating fluid. The synthetic lubricating fluid can be optimized with a non-ionic surfactant, for example, alkylphenol ethoxylate, a linear alcohol ethoxylate, or a DIACID 1550 ethoxylate.

In an embodiment, the lubricating composition is a semi-synthetic lubricating fluid and further includes a coupling solvent, for example tripropylene glycol methyl ether or diethylene glycol monobutyl ether.

In another embodiment, the lubricating composition is a synthetic lubricating fluid and further includes a nonionic surfactant, for example a alkylphenol ethoxylate, a linear alcohol ethoxylate, or a DIACID 1550 ethoxylate.

In certain embodiments, the lubricating composition includes at least one of a biocide and a fungicide.

In certain aspects, the present disclosure relates to a method of lubricating a metal workpiece by applying the aqueous lubricating composition described herein.

In certain other aspects, the present disclosure relates to a machining process comprising performing a machining operation, e.g., metalworking, by flushing, spraying, high pressure spraying, brushing, flowing, fluting, roll coating, immersion, or any combination thereof with the aqueous lubricating composition described herein.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
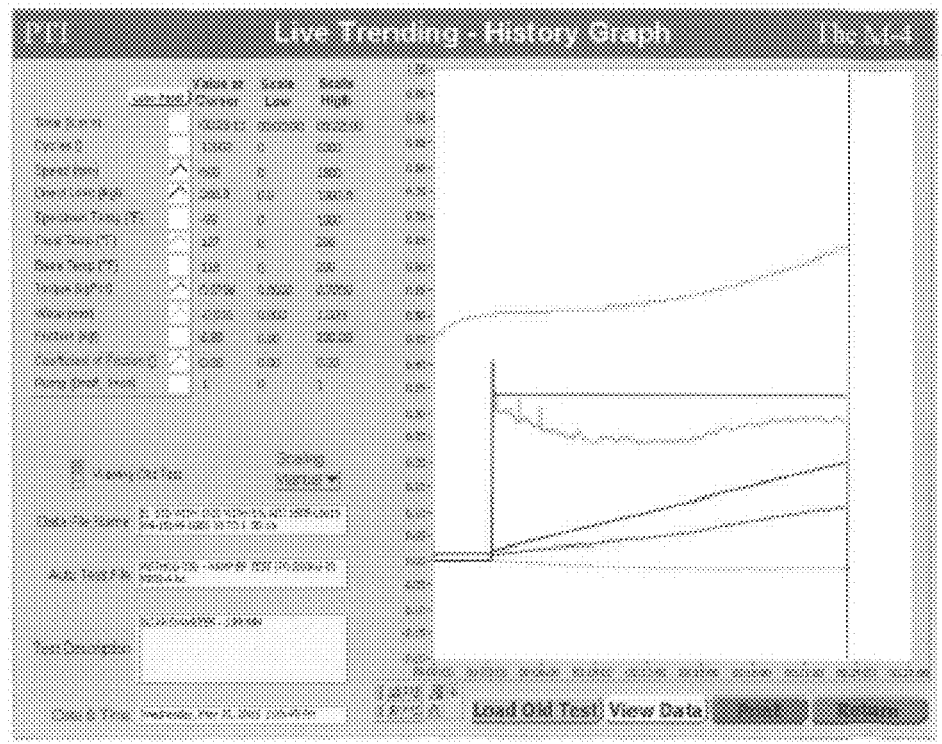
FIG. 1. Graph of DIACID 1550 2-Ethyl-1-hexanol 4Ball Test data.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure. All publications, patent applications, patents, figures and other references mentioned herein are expressly incorporated by reference in their entirety.

As described herein, the present description relates to the surprising and unexpected discovery of an agent that provides superior lubrication and hard water tolerance (i.e. stable in hard water), in a non-foaming or low foaming composition. In particular, the present description discloses lubricating compounds and compositions comprising the same. The compounds described herein include partial esters of a compound derived from the Diels-Alder reaction of a diene, e.g., a conjugated fatty acid, and an acid precursor dienophile. The resulting half-esters as described herein demonstrate at least one of increased stability (i.e., longer shelf life), better performance in hard water, lubricity, and reduced foam formation during use. As such the lubricating compositions as described herein are suitable for numerous applications, including mechanical processes such as metalworking.

In certain embodiments, the diene is a conjugated fatty acid (substituted or unsubstituted).

In certain embodiments the dienophile can be an acrylic acid or an acrylic acid ester. In certain other embodiments the acid precursor dienophile is at least one of methacrylic acid, maleic anhydride, fumaric acid, a fumaric acid mono or diester or a combination thereof. In certain embodiments, the compound derived from the Diels-Alder reaction of a diene, e.g., a conjugated fatty acid, and an acid precursor dienophile is DIACID 1550 (Ingevity Corporation), which is derived from the reaction of a fatty acid and acrylic acid.

In certain embodiments, the lubricating compound is a DIACID 1550 partial or half ester. The DIACID 1550 partial ester can be derived from a reaction product of DIACID 1550 and an alcohol. In an embodiment, the lubricating compound is a partial ester of DIACID 1550 and at least one of n-Pentanol, 1-Dodecanol, or 2-ethyl-1-hexanol.

In another aspect, the description provides lubricating compositions comprising a compound as described herein. The lubricating compositions described herein are useful for a variety of applications including, e.g., metalworking.

In a certain embodiments described herein, the lubricating composition is a semi-synthetic lubricating fluid. The semi-synthetic lubricating fluid can be optimized with a coupling solvent, e.g. tripropylene glycol methyl ether or diethylene glycol monobutyl ether. In another embodiment of the present description, the composition is a synthetic lubricating fluid. The synthetic lubricating fluid can be optimized with a non-ionic surfactant, for example, alkylphenol ethoxylate, a linear alcohol ethoxylate, or a DIACID 1550 ethoxylate.

In another aspect, the description discloses an aqueous lubricating composition comprising a partial ester of a compound derived from the Diels-Alder reaction of a diene, e.g., a conjugated fatty acid, and an acid precursor dienophile, e.g., a DIACID 1550 partial ester. The DIACID 1550 partial ester can be derived from a reaction of an alcohol and DIACID 1550. In a particular embodiment, the alcohol is selected from the group consisting of n-pentanol, 1-dodecanol, 2-ethyl-1-hexanol, and combinations thereof.

DIACID 1550 partial esters, for example a half ester (that is, a monoester), are an effective additive for lubricating fluids, e.g., metalworking fluids. In particular, mixtures comprising DIACID 1550 partial esters, including in combination with at least one of DIACID 1550 bis-esters or diesters or DIACID 1550, are effective additives for lubricating compositions, including, e.g., metalworking fluids. DIACID 1550 half esters have properties that can be used in semi-synthetic and synthetic lubricating fluid formulations. In properly balanced systems, DIACID 1550 half esters provide very good results with regard to emulsion stability in hard water. This hard water stability is a significant improvement over DIACID 1550 alone. The DIACID 1550 half esters also have enhanced lubrication and comparable corrosion inhibition properties compared to DIACID 1550.

In addition, the DIACID 1550 half esters give very good results in synthetic systems when nonionic surfactants are used to adjust the hydrophobic/lipophilic balance (HLB) of the formulation. In semi-synthetic systems, a coupling solvent can be used to optimize formulation stability. The DIACID 1550 half esters appear to be significantly more flexible when compared to DIACID 1550 in these type of formulations.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

As described above, the present description discloses a lubricating fluid composition comprising a partial ester of a Diels-Alder product resulting from the reaction of a diene, e.g., a conjugated fatty acid, with an acid precursor dienophile. In certain embodiments the dienophile can be an acrylic acid or an acrylic acid ester. In certain other embodiments the dienophile can be maleic anhydride or fumaric acid or a fumaric acid mono or diester. In certain embodiments, the compound derived from the Diels-Alder reaction of a diene, e.g., a conjugated fatty acid, and an acid precursor dienophile is DIACID 1550 (Ingevity Corporation), which is derived from the reaction of a fatty acid and acrylic acid.

In certain embodiments, the partial ester is a DIACID 1550 half ester. DIACID 1550 (Ingevity, S.C.) is a Diels-Alder product resulting from the reaction of acrylic acid with a tall oil fatty acid (TOFA). The DIACID 1550 half ester can be derived from a reaction comprising an alcohol and DIACID 1550. In a preferred embodiment, the reaction is performed with a molar excess of carboxyl moieties, such that the majority of esters produced are partial esters. In certain embodiments, the alcohol in the reaction is present at an alcohol to carboxyl moiety molar ratio of less than or equal to 0.5:1. In an embodiment, the half ester is derived from at least one of n-Pentanol, 1-Dodecanol, or 2-ethyl-1-hexanol.

In addition to the DIACID 2-Ethyl-1-hexanol, 1-dodecanol, and n-pentanol half esters, DIACID 1550 half esters of other alcohols can be utilized as a lubricating additive in any of the lubricating compositions described herein, including for metalworking. For example, in an embodiment, the DIACID 1550 half ester alcohol is selected from methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, 2-octadecanol, benzyl alcohol, nonanol, decanol, polyoxyethylene, polyoxypropylene, diol or polyol.

In a particular embodiment, the DIACID 1550 partial ester has Formula (I):

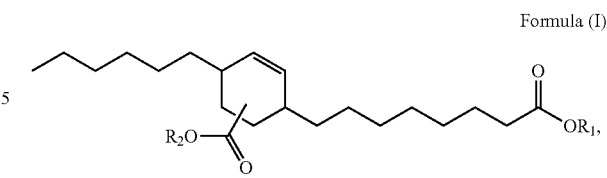

Formula (I)

wherein $R_1$ and $R_2$ are independently selected from the group comprising H, alkyl, alkenyl, cycloalkyl, chloroalkyl, chlorocycloalkyl, polyoxyethylene, polyoxypropylene, or a mixture thereof, and wherein at least one of $R_1$ and $R_2$ is H and the other is not.

In an embodiment, DIACID 1550 has Formula (II):

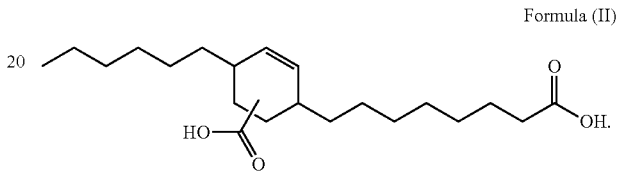

Formula (II)

In certain embodiments, at least one of $R_1$ or $R_2$ but not both is at least one of alkyl, alkenyl, cycloalkyl, chloroalkyl, chlorocycloalkyl, polyoxyethylene and polyoxypropylene.

In a certain embodiment, at least 10 mol-% of $R_1$ and $R_2$ are H. In another embodiment, up to 90 mol-% of $R_1$ or $R_2$ are at least one of alkyl, alkenyl, cycloalkyl, chloroalkyl, chlorocycloalkyl, polyoxyethylene and polyoxypropylene.

The DIACID 1550 partial ester alcohol of the description may have the Formula (III): $HO—R^3—R^4$, wherein $R^3$ comprises an aliphatic group having 1 to 50 carbon atoms, and $R^2$ or $R^4$ comprises either H or an aromatic ring bound to any carbon atom of $R^3$. Alternatively, the DIACID 1550 partial ester alcohol of the description may have the formula As used herein, the term "alcohol" refers to a compound in which a hydroxyl group (—OH) is attached to a carbon atom.

As used here, the term "aliphatic" refers to a carbon and hydrogen group that can be saturated or unsaturated without an aromatic arrangement.

As used herein, "diol" refers to a compound that contains two hydroxyl groups.

As used herein, "polyol" refers to a compound that contains multiple hydroxyl groups.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "chloroalkyl," by itself or as part of another substituent means, unless otherwise states, any alkyl radical having one or more hydrogen atoms replaced by chlorine.

As used herein, the term "chlorocycloalkyl," by itself or as part of another substituent means, unless otherwise states, any cycloalkyl radical having one or more hydrogen atoms replace by chlorine.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

In an embodiment, the esterification of the Diels-Alder reaction product, e.g., DIACID 1550, is not complete (i.e., DIACID 1550 retains at least one unsubstituted carboxyl). For example, by reacting the alcohol or alkoxy with DIACID 1550, wherein the molar ratio of the alcohol to carboxyl moieties is less than 1:1, partial esterification of DIACID 1550 is achieved.

In certain embodiments, the description provides a lubricating composition, e.g., a lubricating fluid composition, comprising a partial (i.e., half) ester of a Diels-Alder reaction product of a diene, e.g., conjugated fatty acid, and a dienophile, e.g., an acid precursor dienophile. In certain additional embodiments, the diene is a conjugated fatty acid (substituted or unsubstituted).

In certain embodiments the dienophile can be an acrylic acid or an acrylic acid ester. In additional embodiments, the acid precursor dienophile is methacrylic acid. In certain other embodiments the dienophile can be maleic anhydride or fumaric acid or a fumaric acid mono or diester. In certain embodiments, the compound derived from the Diels-Alder reaction of a diene, e.g., a conjugated fatty acid, and an acid precursor dienophile is DIACID 1550 (Ingevity Corporation), which is derived from the reaction of a fatty acid and acrylic acid.

In certain embodiments, the conjugated fatty acid is derived from tall oil fatty acid. In additional embodiments, the conjugated fatty acid is linoleic acid.

In certain embodiments, the compound derived from the Diels-Alder reaction of a conjugated fatty acid and acrylic acid is DIACID 1550, and the partial ester is a DIACID 1550 partial ester.

In another aspect, the description provides a lubricating composition, e.g., a lubricating fluid, comprising a partial ester compound as described herein. In certain embodiments, the composition comprises a mixture of DIACID 1550 partial (i.e., half) esters.

In certain embodiments, the description provides a lubricating composition, e.g., a lubricating fluid, comprising a mixture of DIACID 1550 partial (i.e., half) ester, DIACID 1550 bis-ester, and DIACID 1550. In certain embodiments, the composition comprises an excess of DIACID 1550 partial ester relative to at least one of the bis-ester, DIACID 1550 or a combination thereof. In additional embodiments, the amount of DIACID 1550 partial ester is at least 2×, 3×, or 4×, the amount of either the bis-ester or DIACID 1550.

In certain embodiments, the description provides a lubricating composition, e.g., a lubricating fluid or metalworking fluid comprising from about 40% to about 80% (based on Area % as determined by GPC) DIACID 1550 partial ester. In certain additional embodiments, the DIACID 1550 partial ester may be present in a range of about 40% to about 75%, about 40% to about 70%, about 40% to about 65%, about 40% to about 60%, about 40% to about 55%, about 40% to about 50%, about 40% to about 45%, 45% to about 80%, about 45% to about 75%, about 45% to about 70%, about 45% to about 65%, about 45% to about 60%, about 45% to about 55%, about 45% to about 50%, 50% to about 80%, about 50% to about 75%, about 50% to about 70%, about 50% to about 65%, about 50% to about 60%, about 50% to about 55%, 55% to about 80%, about 55% to about 75%, about 55% to about 70%, about 55% to about 65%, about 55% to about 60%, 60% to about 80%, about 60% to about 75%, about 60% to about 70%, about 60% to about 65%, 65% to about 80%, about 65% to about 75%, about 65% to about 70%, 70% to about 80%, about 70% to about 75%, or about 75% to about 80%. In certain embodiments, DIACID 1550 partial ester is present in about 40%, about 42.5%, about 45%, about 47.5%, about 50%, about 52.5%, about 55%, about 57.5%, about 60%, about 62.5%, about 65%, about 67.5%, about 70%, about 72.5%, about 75%, about 77.5%, or about 80% (all of the above percentages are based on Area % as determined by GPC).

In certain embodiments, the lubricating composition, e.g., a lubricating fluid or metalworking fluid further comprises DIACID 1550 in a range of about 5% to about 35%, about 5% to about 32.5%, about 5% to about 30%, about 5% to about 27.5%, about 5% to about 25%, about 5% to about 22.5%, about 5% to about 20%, about 5% to about 17.5%, about 5% to about 15%, about 5% to about 12.5%, about 5% to about 10%, about 5% to about 7.5%, about 7.5% to about 35%, about 7.5% to about 32.5%, about 7.5% to about 30%, about 7.5% to about 27.5%, about 7.5% to about 25%, about 7.5% to about 22.5%, about 7.5% to about 20%, about 7.5% to about 17.5%, about 7.5% to about 15%, about 7.5% to about 12.5%, about 7.5% to about 10%, about 10% to about 35%, about 10% to about 32.5%, about 10% to about 30%, about 10% to about 27.5%, about 10% to about 25%, about 10% to about 22.5%, about 10% to about 20%, about 10% to about 17.5%, about 10% to about 15%, about 10% to about 12.5%, about 12.5% to about 35%, about 12.5% to about 32.5%, about 12.5% to about 30%, about 12.5% to about 27.5%, about 12.5% to about 25%, about 12.5% to about 22.5%, about 12.5% to about 20%, about 12.5% to about 17.5%, about 12.5% to about 15%, about 15% to about 35%, about 15% to about 32.5%, about 15% to about 30%, about 15% to about 27.5%, about 15% to about 25%, about 15% to about 22.5%, about 15% to about 20%, about 15% to about 17.5%, about 17.5% to about 35%, about 17.5% to about 32.5%, about 17.5% to about 30%, about 17.5% to about 27.5%, about 17.5% to about 25%, about 17.5% to about 22.5%, about 17.5% to about 20%, about 20% to about 35%, about 20% to about 32.5%, about 20% to about 30%, about 20% to about 27.5%, about 20% to about 25%, about 20% to about 22.5%, about 22.5% to about 35%, about 22.5% to about 32.5%, about 22.5% to about 30%, about 22.5% to about 27.5%, about 22.5% to about 25%, about 25% to about 35%, about 25% to about 32.5%, about 25% to about 30%, about 25% to about 27.5%, about 27.5% to about 35%, about 27.5% to about 32.5%, about 27.5% to about 30%, about 30% to about 35%, about 30% to about 32.5%, or about 32.5% to about 35%. (All of the above percentages are based on Area % as determined by GPC).

In certain embodiments, the lubricating composition, e.g., a lubricating fluid or metalworking fluid comprises DIACID 1550 in about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35%. (All of the above percentages are based on Area % as determined by GPC).

In certain embodiments, the lubricating composition, e.g., a lubricating fluid or metalworking fluid further comprises DIACID 1550 bis-ester in a range of about 5% to about 35%, about 5% to about 32.5%, about 5% to about 30%, about 5% to about 27.5%, about 5% to about 25%, about 5% to about 22.5%, about 5% to about 20%, about 5% to about 17.5%, about 5% to about 15%, about 5% to about 12.5%, about 5% to about 10%, about 5% to about 7.5%, about 7.5% to about 35%, about 7.5% to about 32.5%, about 7.5% to about 30%, about 7.5% to about 27.5%, about 7.5% to about 25%, about 7.5% to about 22.5%, about 7.5% to about 20%, about 7.5% to about 17.5%, about 7.5% to about 15%, about 7.5% to about 12.5%, about 7.5% to about 10%, about 10% to about 35%, about 10% to about 32.5%, about 10% to about 30%, about 10% to about 27.5%, about 10% to about 25%, about 10% to about 22.5%, about 10% to about 20%, about 10% to about 17.5%, about 10% to about 15%, about 10% to about 12.5%, about 12.5% to about 35%, about 12.5% to about 32.5%, about 12.5% to about 30%, about 12.5% to about 27.5%, about 12.5% to about 25%, about 12.5% to about 22.5%, about 12.5% to about 20%, about 12.5% to about 17.5%, about 12.5% to about 15%, about 15% to about 35%, about 15% to about 32.5%, about 15% to about 30%, about 15% to about 27.5%, about 15% to about 25%, about 15% to about 22.5%, about 15% to about 20%, about 15% to about 17.5%, about 17.5% to about 35%, about 17.5% to about 32.5%, about 17.5% to about 30%, about 17.5% to about 27.5%, about 17.5% to about 25%, about 17.5% to about 22.5%, about 17.5% to about 20%, about 20% to about 35%, about 20% to about 32.5%, about 20% to about 30%, about 20% to about 27.5%, about 20% to about 25%, about 20% to about 22.5%, about 22.5% to about 35%, about 22.5% to about 32.5%, about 22.5% to about 30%, about 22.5% to about 27.5%, about 22.5% to about 25%, about 25% to about 35%, about 25% to about 32.5%, about 25% to about 30%, about 25% to about 27.5%, about 27.5% to about 35%, about 27.5% to about 32.5%, about 27.5% to about 30%, about 30% to about 35%, about 30% to about 32.5%, or about 32.5% to about 35%. (All of the above percentages are based on Area % as determined by GPC).

In certain embodiments, the DIACID 1550 bis-ester is present in about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35%. (All of the above percentages are based on Area % as determined by GPC).

In an embodiment, the DIACID 1550 partial ester composition may include a ratio of DIACID 1550 half ester to DIACID 1550 bis ester in a range of about 16:1 to about 1:1, about 15:1 to about 1:1, about 14:1 to about 1:1, about 13:1 to about 1:1, about 12:1 to about 1:1, about 11:1 to about 1:1, about 10:1 to about 1:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, about 2:1 to about 1:1, about 16:1 to about 2:1, about 15:1 to about 2:1, about 14:1 to about 2:1, about 13:1 to about 2:1, about 12:1 to about 2:1, about 11:1 to about 2:1, about 10:1 to about 2:1, about 9:1 to about 2:1, about 8:1 to about 2:1, about 7:1 to about 2:1, about 6:1 to about 2:1, about 5:1 to about 2:1, about 4:1 to about 2:1, about 3:1 to about 2:1, about 16:1 to about 3:1, about 15:1 to about 3:1, about 14:1 to about 3:1, about 13:1 to about 3:1, about 12:1 to about 3:1, about 11:1 to about 3:1, about 10:1 to about 3:1, about 9:1 to about 3:1, about 8:1 to about 3:1, about 7:1 to about 3:1, about 6:1 to about 3:1, about 5:1 to about 3:1, about 4:1 to about 3:1, about 16:1 to about 4:1, about 15:1 to about 4:1, about 14:1 to about 4:1, about 13:1 to about 4:1, about 12:1 to about 4:1, about 11:1 to about 4:1, about 10:1 to about 4:1, about 9:1 to about 4:1, about 8:1 to about 4:1, about 7:1 to about 4:1, about 6:1 to about 4:1, about 5:1 to about 4:1, about 16:1 to about 5:1, about 15:1 to about 5:1, about 14:1 to about 5:1, about 13:1 to about 5:1, about 12:1 to about 5:1, about 11:1 to about 5:1, about 10:1 to about 5:1, about 9:1 to about 5:1, about 8:1 to about 5:1, about 7:1 to about 5:1, about 6:1 to about 5:1, about 16:1 to about 6:1, about 15:1 to about 6:1, about 14:1 to about 6:1, about 13:1 to about 6:1, about 12:1 to about 6:1, about 11:1 to about 6:1, about 10:1 to about 6:1, about 9:1 to about 6:1, about 8:1 to about 6:1, about 7:1 to about 6:1, about 16:1 to about 7:1, about 15:1 to about 7:1, about 14:1 to about 7:1, about 13:1 to about 7:1, about 12:1 to about 7:1, about 11:1 to about 7:1, about 10:1 to about 7:1, about 9:1 to about 7:1, about 8:1 to about 7:1, about 16:1 to about 8:1, about 15:1 to about 8:1, about 14:1 to about 8:1, about 13:1 to about 8:1, about 12:1 to about 8:1, about 11:1 to about 8:1, about 10:1 to about 8:1, about 9:1 to about 8:1, about 16:1 to about 9:1, about 15:1 to about 9:1, about 14:1 to about 9:1, about 13:1 to about 9:1, about 12:1 to about 9:1, about 11:1 to about 9:1, about 10:1 to about 9:1, about 16:1 to about 10:1, about 15:1 to about 10:1, about 14:1 to about 10:1, about 13:1 to about 10:1, about 12:1 to about 10:1, about 11:1 to about 10:1, about 16:1 to about 11:1, about 15:1 to about 11:1, about 14:1 to about 11:1, about 13:1 to about 11:1, about 12:1 to about 11:1, about 16:1 to about 12:1, about 15:1 to about 12:1, about 14:1 to about 12:1, about 13:1 to about 12:1, about 16:1 to about 13:1, about 15:1 to about 13:1, about 14:1 to about 13:1, about 16:1 to about 14:1, about 15:1 to about 14:1, or about 16:1 to about 15:1. In a certain embodiment, a ratio of DIACID 1550 half ester to DIACID 1550 bis ester is about 16:1, about 15:1, about 14:1 about 13:1, about 12:1, about 11:1, about 10:1, about 9:1, about 8:1, about 7:1, about 6:1, about 5:1, about 4:1, about 3:1, about 2:1, about 8:7, or about 1:1.

In an embodiment, the DIACID 1550 partial ester composition may include a ratio of DIACID 1550 half ester to DIACID 1550 in a range of about 16:1 to about 1:1, about 15:1 to about 1:1, about 14:1 to about 1:1, about 13:1 to about 1:1, about 12:1 to about 1:1, about 11:1 to about 1:1, about 10:1 to about 1:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, about 2:1 to about 1:1, about 16:1 to about 2:1, about 15:1 to about 2:1, about 14:1 to about 2:1, about 13:1 to about 2:1, about 12:1 to about 2:1, about 11:1 to about 2:1, about 10:1 to about 2:1, about 9:1 to about 2:1, about 8:1 to about 2:1, about 7:1 to about 2:1, about 6:1 to about 2:1, about 5:1 to about 2:1, about 4:1 to about 2:1, about 3:1 to about 2:1, about 16:1 to about 3:1, about 15:1 to about 3:1, about 14:1 to about 3:1, about 13:1 to about 3:1, about 12:1 to about 3:1, about 11:1 to about 3:1, about 10:1 to about 3:1, about 9:1 to about 3:1, about 8:1 to about 3:1, about 7:1 to about 3:1, about 6:1 to about 3:1, about 5:1 to about 3:1, about 4:1 to about 3:1, about 16:1 to about 4:1, about 15:1 to about 4:1, about 14:1 to about 4:1, about 13:1 to about 4:1, about 12:1 to about 4:1, about 11:1 to about 4:1, about 10:1 to about 4:1, about 9:1 to about 4:1, about 8:1 to about 4:1, about 7:1 to about 4:1, about 6:1 to about 4:1, about 5:1 to about 4:1, about 16:1 to about 5:1, about 15:1 to about 5:1, about 14:1 to about 5:1, about 13:1 to about 5:1, about 12:1 to about 5:1, about 11:1 to about 5:1, about 10:1 to about 5:1, about 9:1 to about 5:1, about 8:1 to about 5:1, about 7:1 to about 5:1, about 6:1 to about 5:1, about 16:1 to about 6:1, about 15:1 to about 6:1, about 14:1 to about 6:1, about 13:1 to about 6:1, about 12:1 to about 6:1, about 11:1 to about 6:1, about 10:1 to about 6:1, about 9:1 to about 6:1, about 8:1 to about 6:1, about 7:1 to about 6:1, about 16:1 to about 7:1, about 15:1 to about 7:1, about 14:1 to about 7:1, about 13:1 to about 7:1, about 12:1 to about 7:1, about 11:1 to about 7:1, about 10:1 to about 7:1, about 9:1 to about 7:1, about 8:1 to about 7:1, about 16:1 to about 8:1, about 15:1 to about 8:1, about 14:1 to about 8:1, about 13:1 to about 8:1, about 12:1 to about 8:1, about 11:1 to about 8:1, about 10:1 to about 8:1, about 9:1 to about 8:1, about 16:1 to about 9:1, about 15:1 to about 9:1, about 14:1 to about 9:1, about 13:1 to about 9:1, about 12:1 to about 9:1, about 11:1 to about 9:1, about 10:1 to about 9:1, about 16:1 to about 10:1, about 15:1 to about 10:1, about 14:1 to about 10:1, about 13:1 to about 10:1, about 12:1 to about 10:1, about 11:1 to about 10:1, about 16:1 to about 11:1, about 15:1 to about 11:1, about 14:1 to about 11:1, about 13:1 to about 11:1, about 12:1 to about 11:1, about 16:1 to about 12:1, about 15:1 to about 12:1, about 14:1 to about 12:1, about 13:1 to about 12:1, about 16:1 to about 13:1, about 15:1 to about 13:1, about 14:1 to about 13:1, about 16:1 to about 14:1, about 15:1 to about 14:1, or about 16:1 to about 15:1. In a certain embodiment, a ratio of DIACID 1550 half ester to DIACID 1550 is about 16:1, about 15:1, about 14:1 about 13:1, about 12:1, about 11:1, about 10:1, about 9:1, about 8:1, about 7:1, about 6:1, about 5:1, about 4:1, about 3:1, about 2:1, about 8:7, or about 1:1.

In certain aspects, the partial esterification of DIACID 1550 can take place in the presence of one or more (i.e., a mixture) of alcohols, for example, at least two alcohols, at least three alcohols, or at least four alcohols. For example, the at least two alcohols can be selected from 2-ethyl-1-hexanol, 1-dodecanol, and n-pentanol. In an embodiment, the DIACID 1550 ester is a partially esterified DIACID 1550.

In certain embodiments, the lubricating composition, e.g., a lubricating fluid or metalworking fluid described herein comprises a counterion. In certain embodiments, the counterion is selected from the group consisting of sodium, potassium, ammonium, or triethanolamine (TEA).

In an embodiment, the description provides a semi-synthetic lubricating composition, e.g., a lubricating fluid or metalworking fluid. The semi-synthetic lubricating composition, e.g., a lubricating fluid or metalworking fluid can be optimized with a coupling solvent, e.g. tripropylene glycol methyl ether or diethylene glycol monobutyl ether. In another embodiment of the present description, the composition is a synthetic lubricating composition, e.g., a lubricating fluid or metalworking fluid. The synthetic lubricating composition, e.g., a lubricating fluid or metalworking fluid can be optimized with a non-ionic surfactant, for example, a alkylphenol ethoxylate, a linear alcohol ethoxylate, or a DIACID 1550 ethoxylate.

In another aspect, the description discloses an aqueous lubricating composition, e.g., a lubricating fluid or metalworking fluid composition comprising a DIACID 1550 partial ester (e.g. a half ester). The DIACID 1550 partial ester can be derived from a reaction of an alcohol and DIACID 1550. In a particular embodiment, the alcohol is selected from the group consisting of n-pentanol, 1-dodecanol, 2-ethyl-1-hexanol, and combinations thereof.

In an embodiment, the lubricating composition, e.g., a lubricating fluid or metalworking fluid is a semi-synthetic lubricating composition, e.g., a lubricating fluid or metalworking fluid and further includes a coupling solvent, for example tripropylene glycol methyl ether or diethylene glycol monobutyl ether.

In another embodiment, the lubricating composition, e.g., a lubricating fluid or metalworking fluid is a synthetic lubricating composition, e.g., a lubricating fluid or metalworking fluid and further includes a nonionic surfactant, for example, an alkylphenol ethoxylate, a linear alcohol ethoxylate, or a DIACID 1550 ethoxylate. Other exemplary nonionic surfactants include, for example, include ethylene oxide adducts of alcohols, polyols, phenols, carboxylic acids and carboxylic acid esters such as ethylene oxide adducts of oleyl alcohol, nonyl phenol, glycerol, sorbitol, mannitol, pentaerythritol, sorbitan monolaurate, glycerol monooleate, pentaerythritol monostearate, oleic acid, stearic acid, and the like.

In certain embodiment, the lubricating composition, e.g., a lubricating fluid or metalworking fluid includes at least one of a biocide and a fungicide. In an embodiment, the biocide is at least one of CONTRAM™ 121, CONTRAM™ CB Metalworking Fluid System Cleaners, CONTRAM™ MBO, CONTRAM™ OF-G, CONTRAM™ ST-1, BIOBAN™ 1487, ROCIMA™ BT 2S, BIOBAN™ DB-20, SUMP BUDDY™ MWF, BIOBAN™ BP-30, KORDEK™ LX5000, UCARCIDE™ 50, UCARCIDE™ 25, DOWICIL™ 75, BIOBAN™ P-1487, DOWACIDE™ A, DOWICIDE™ 25L, KATHON™ 886 MW, DOWICIDE™ 1E. In an embodiment, the fungicide is at least one of Polyphase FX-40, BIOBAN™ IPBC-40, BIOBAN™ IPBC-40 L E, DOWICIDE™ 25L, DOWICIDE™ A, KATHON™ 893 MW, KATHON™ 886 MW, DOWICIDE™ A, DOWICIDE™ 1E, BIOBAN™ P-1487, and Omacide™ fungicides (iodopropynyl butyl carbamate).

In certain aspects, the present disclosure relates to a method of lubricating a metal workpiece by applying the aqueous metalworking composition described herein.

In certain other aspects, the present disclosure relates to a metalworking process comprising performing a metalworking operation by flushing, spraying, high pressure spraying, brushing, flowing, fluting, roll coating, immersion, or any combination thereof with the aqueous metalworking composition described herein.

In an embodiment, the description provides a full synthetic formulation comprising a DIACID partial ester, including from about 1 to about 10% by weight of TEA, from about 5 to about 25% by weight of DIACID 1550 partial ester (e.g., 2-ethylhexanol, 1-dodecanol, or n-pentanol), from about 1 to about 10% by weight emulsifier (e.g. TOFA Alkanolamide), and optionally, from about 0.1 to about 5% by weight coupler (e.g. propylene glycol butyl ether). The DIACID half ester full synthetic formulation may further comprise from about 0.1 to about 10% by weight of a biocide (e.g. BIOBAN™ 1487) and/or from about 0.1 to about 10% by weight of a fungicide. In another embodiment, DIACID partial ester full synthetic formulation comprises from about 5 to about 8% by weight of TEA, from about 16 to about 20% by weight of DIACID 1550 partial ester (e.g., 2-ethylhexanol, 1-dodecanol, or n-pentanol), from about 4 to about 8% by weight emulsifier (e.g. TOFA Alkanolamide), and optionally, from about 0.1 to about 5% by weight coupler (e.g. propylene glycol butyl ether). The DIACID partial ester full synthetic formulation may further comprise from about 1 to about 7% by weight of a biocide (e.g. BIOBAN™ 1487) and/or from about 1 to about 7% by weight of a fungicide. In a particular embodiment, the DIACID half ester full synthetic formulation comprises about 6.6% by weight of TEA, about 18% by weight of DIACID 1550 partial ester (e.g., 2-ethylhexanol, 1-dodecanol, or n-pentanol), about 6.5% by weight emulsifier (e.g. TOFA Alkanolamide), and optionally, about 1.5% by weight coupler (e.g. DOWANOL™ PnB).

In another embodiment, the description provides semi-synthetic formulation comprising a DIACID partial ester, including from about 5 to about 50% by weight of oil (e.g. 100 SU naphthenic oil), from about 1 to about 10% by weight of DIACID 1550 partial ester (e.g., 2-ethylhexanol, 1-dodecanol, or n-pentanol), from about 0.1 to about 5% by weight of TEA, from about 5 to about 25% by weight of an emulsifier (e.g. TOFA Alkanolamide), and optionally, from about 1 to about 10% by weight coupler (e.g. propylene glycol butyl ether). The DIACID partial ester semi-synthetic formulation may further comprise from about 1 to about 10% by weight of a second emulsifier (e.g. petroleum sulfonate). In an embodiment, the DIACID partial ester semi-synthetic formulation comprises from about 8 to about 20% by weight of oil (e.g. 100 SU naphthenic oil), from about 3 to about 8% by weight of DIACID 1550 partial ester (e.g., 2-ethylhexanol, 1-dodecanol, or n-pentanol), from about 0.75 to about 3.5% by weight of TEA, from about 10 to about 20% by weight of an emulsifier (e.g. TOFA Alkanolamide), and optionally, from about 2 to about 8% by weight coupler (e.g. propylene glycol butyl ether). The DIACID partial ester semi-synthetic formulation can further comprise from about 2 to about 8% by weight of a second emulsifier (e.g. petroleum sulfonate). The DIACID 1550 partial ester semi-synthetic formulation may comprise from about 0.1 to about 10% by weight of a biocide (e.g. BIOBAN™ 1487) and/or from about 0.1 to about 10% by weight of a fungicide. In a particular embodiment, the DIACID partial ester semi-synthetic formulation comprises about 10% by weight of oil (e.g. 100 SU naphthenic oil), about 5% by weight of DIACID 1550 partial ester (e.g., 2-ethylhexanol, 1-dodecanol, or n-pentanol), about 1.75% by weight of TEA, about 15% by weight of a first emulsifier (e.g. TOFA Alkanolamide), about 5% by weight of a second emulsifier (e.g. petroleum sulfonate), about 3% by weight of a biocide (e.g. BIOBAN™ 1487), and optionally, about 5% by weight coupler (e.g. DOWANOL™ PnB).

In certain embodiments, the DIACID 1550 partial ester is present in a range of about 1% to about 25% by weight, about 1% to about 24% by weight, about 1% to about 23% by weight, about 1% to about 22% by weight, about 1% to about 21% by weight, about 1% to about 20% by weight, about 1% to about 19% by weight, about 1% to about 18% by weight, about 1% to about 17% by weight, about 1% to about 16% by weight, about 1% to about 15% by weight, about 1% to about 14% by weight, about 1% to about 13% by weight, about 1% to about 12% by weight, about 1% to about 11% by weight, about 1% to about 10% by weight, about 1% to about 9% by weight, about 1% to about 8% by weight, about 1% to about 7% by weight, about 1% to about 6% by weight, about 1% to about 5% by weight, about 1% to about 4% by weight, about 1% to about 3% by weight, about 1% to about 2% by weight, including all ranges in between. about 2% to about 25% by weight, about 2% to about 24% by weight, about 2% to about 23% by weight, about 2% to about 22% by weight, about 2% to about 21% by weight, about 2% to about 20% by weight, about 2% to about 19% by weight, about 2% to about 18% by weight, about 2% to about 17% by weight, about 2% to about 16% by weight, about 2% to about 15% by weight, about 2% to about 14% by weight, about 2% to about 13% by weight, about 2% to about 12% by weight, about 2% to about 11% by weight, about 2% to about 10% by weight, about 2% to about 9% by weight, about 2% to about 8% by weight, about 2% to about 7% by weight, about 2% to about 6% by weight, about 2% to about 5% by weight, about 2% to about 4% by weight, about 2% to about 3% by weight, about 3% to about 25% by weight, about 3% to about 24% by weight, about 3% to about 23% by weight, about 3% to about 22% by weight, about 3% to about 21% by weight, about 3% to about 20% by weight, about 3% to about 19% by weight, about 3% to about 18% by weight, about 3% to about 17% by weight, about 3% to about 16% by weight, about 3% to about 15% by weight, about 3% to about 14% by weight, about 3% to about 13% by weight, about 3% to about 12% by weight, about 3% to about 11% by weight, about 3% to about 10% by weight, about 3% to about 9% by weight, about 3% to about 8% by weight, about 3% to about 7% by weight, about 3% to about 6% by weight, about 3% to about 5% by weight, about 3% to about 4% by weight, about 4% to about 25% by weight, about 4% to about 24% by weight, about 4% to about 23% by weight, about 4% to about 22% by weight, about 4% to about 21% by weight, about 4% to about 20% by weight, about 4% to about 19% by weight, about 4% to about 18% by weight, about 4% to about 17% by weight, about 4% to about 16% by weight, about 4% to about 15% by weight, about 4% to about 14% by weight, about 4% to about 13% by weight, about 4% to about 12% by weight, about 4% to about 11% by weight, about 4% to about 10% by weight, about 4% to about 9% by weight, about 4% to about 8% by weight, about 4% to about 7% by weight, about 4% to about 6% by weight, about 4% to about 5% by weight, about 5% to about 25% by weight, about 5% to about 24% by weight, about 5% to about 23% by weight, about 5% to about 22% by weight, about 5% to about 21% by weight, about 5% to about 20% by weight, about 5% to about 19% by weight, about 5% to about 18% by weight, about 5% to about 17% by weight, about 5% to about 16% by weight, about 5% to about 15% by weight, about 5% to about 14% by weight, about 5% to about 13% by weight, about 5% to about 12% by weight, about 5% to about 11% by weight, about 5% to about 10% by weight, about 5% to about 9% by weight, about 5% to about 8% by weight, about 5% to about 7% by weight, about 5% to about 6% by weight, about 6% to about 25% by weight, about 6% to about 24% by weight, about 6% to about 23% by weight, about 6% to about 22% by weight, about 6% to about 21% by weight, about 6% to about 20% by weight, about 6% to about 19% by weight, about 6% to about 18% by weight, about 6% to about 17% by weight, about 6% to about 16% by weight, about 6% to about 15% by weight, about 6% to about 14% by weight, about 6% to about 13% by weight, about 6% to about 12% by weight, about 6% to about 11% by weight, about 6% to about 10% by weight, about 6% to about 9% by weight, about 6% to about 8% by weight, about 6% to about 7% by weight, about 7% to about 25% by weight, about 7% to about 24% by weight, about 7% to about 23% by weight, about 7% to about 22% by weight, about 7% to about 21% by weight, about 7% to about 20% by weight, about 7% to about 19% by weight, about 7% to about 18% by weight, about 7% to about 17% by weight, about 7% to about 16% by weight, about 7% to about 15% by weight, about 7% to about 14% by weight, about 7% to about 13% by weight, about 7% to about 12% by weight, about 7% to about 11% by weight, about 7% to about 10% by weight, about 7% to about 9% by weight, about 7% to about 8% by weight, about 8% to about 25% by weight, about 8% to about 24% by weight, about 8% to about 23% by weight, about 8% to about 22% by weight, about 8% to about 21% by weight, about 8% to about 20% by weight, about 8% to about 19% by weight, about 8% to about 18% by weight, about 8% to about 17% by weight, about 8% to about 16% by weight, about 8% to about 15% by weight, about 8% to about 14% by weight, about 8% to about 13% by weight, about 8% to about 12% by weight, about 8% to about 11% by weight, about 8% to about 10% by weight, about 8% to about 9% by weight, about 9% to about 25% by weight, about 9% to about 24% by weight, about 9% to about 23% by weight, about 9% to about 22% by weight, about 9% to about 21% by weight, about 9% to about 20% by weight, about 9% to about 19% by weight, about 9% to about 18% by weight, about 9% to about 17% by weight, about 9% to about 16% by weight, about 9% to about 15% by weight, about 9% to about 14% by weight, about 9% to about 13% by weight, about 9% to about 12% by weight, about 9% to about 11% by weight, about 9% to about 10% by weight, about 10% to about 25% by weight, about 10% to about 24% by weight, about 10% to about 23% by weight, about 10% to about 22% by weight, about 10% to about 21% by weight, about 10% to about 20% by weight, about 10% to about 19% by weight, about 10% to about 18% by weight, about 10% to about 17% by weight, about 10% to about 16% by weight, about 10% to about 15% by weight, about 10% to about 14% by weight, about 10% to about 13% by weight, about 10% to about 12% by weight, about 10% to about 11% by weight, about 11% to about 25% by weight, about 11% to about 24% by weight, about 11% to about 23% by weight, about 11% to about 22% by weight, about 11% to about 21% by weight, about 11% to about 20% by weight, about 11% to about 19% by weight, about 11% to about 18% by weight, about 11% to about 17% by weight, about 11% to about 16% by weight, about 11% to about 15% by weight, about 11% to about 14% by weight, about 11% to about 13% by weight, about 11% to about 12% by weight, about 12% to about 25% by weight, about 12% to about 24% by weight, about 12% to about 23% by weight, about 12% to about 22% by weight, about 12% to about 21% by weight, about 12% to about 20% by weight, about 12% to about 19% by weight, about 12% to about 18% by weight, about 12% to about 17% by weight, about 12% to about 16% by weight, about 12% to about 15% by weight, about 12% to about 14% by weight, about 12% to about 13% by weight, about 13% to about 25% by weight, about 13% to about 24% by weight, about 13% to about 23% by weight, about 13% to about 22% by weight, about 13% to about 21% by weight, about 13% to about 20% by weight, about 13% to about 19% by weight, about 13% to about 18% by weight, about 13% to about 17% by weight, about 13% to about 16% by weight, about 13% to about 15% by weight, about 13% to about 14% by weight, about 14% to about 25% by weight, about 14% to about 24% by weight, about 14% to about 23% by weight, about 14% to about 22% by weight, about 14% to about 21% by weight, about 14% to about 20% by weight, about 14% to about 19% by weight, about 14% to about 18% by weight, about 14% to about 17% by weight, about 14% to about 16% by weight, about 14% to about 15% by weight, about 15% to about 25% by weight, about 15% to about 24% by weight, about 15% to about 23% by weight, about 15% to about 22% by weight, about 15% to about 21% by weight, about 15% to about 20% by weight, about 15% to about 19% by weight, about 15% to about 18% by weight, about 15% to about 17% by weight, about 15% to about 16% by weight, about 16% to about 25% by weight, about 16% to about 24% by weight, about 16% to about 23% by weight, about 16% to about 22% by weight, about 16% to about 21% by weight, about 16% to about 20% by weight, about 16% to about 19% by weight, about 16% to about 18% by weight, about 16% to about 17% by weight, about 17% to about 25% by weight, about 17% to about 24% by weight, about 17% to about 23% by weight, about 17% to about 22% by weight, about 17% to about 21% by weight, about 17% to about 20% by weight, about 17% to about 19% by weight, about 17% to about 18% by weight, about 18% to about 25% by weight, about 18% to about 24% by weight, about 18% to about 23% by weight, about 18% to about 22% by weight, about 18% to about 21% by weight, about 18% to about 20% by weight, about 18% to about 19% by weight, about 19% to about 25% by weight, about 19% to about 24% by weight, about 19% to about 23% by weight, about 19% to about 22% by weight, about 19% to about 21% by weight, about 19% to about 20% by weight, about 20% to about 25% by weight, about 20% to about 24% by weight, about 20% to about 23% by weight, about 20% to about 22% by weight, about 20% to about 21% by weight, about 21% to about 25% by weight, about 21% to about 24% by weight, about 21% to about 23% by weight, about 21% to about 22% by weight, about 22% to about 25% by weight, about 22% to about 24% by weight, about 22% to about 23% by weight, about 23% to about 25% by weight, about 23% to about 24% by weight, or about 24% to about 25% by weight. In certain embodiments, DIACID 1550 partial ester is present in about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 6.5% by weight, about 7% by weight, about 7.5% by weight, about 8% by weight, about 8.5% by weight, about 9% by weight, about 9.5% by weight, about 10% by weight, about 10.5% by weight, about 11% by weight, about 11.5% by weight, about 12% by weight, about 12.5% by weight, about 13% by weight, about 13.5% by weight, about 14% by weight, about 14.5% by weight, about 15% by weight, about 15.5% by weight, about 16% by weight, about 16.5% by weight, about 17% by weight, about 17.5% by weight, about 18% by weight, about 18.5% by weight, about 19% by weight, about 19.5% by weight, about 20% by weight, about 20.5% by weight, about 21% by weight, about 21.5% by weight, about 22% by weight, about 22.5% by weight, about 23% by weight, about 23.5% by weight, about 24% by weight, about 24.5% by weight, or about 25% by weight.

In additional embodiments, the base (e.g., TEA or potassium hydroxide) is present in a range of about 0.1% to about 10% by weight, about 0.1% to about 9.5% by weight, about 0.1% to about 9% by weight, about 0.1% to about 8.5% by weight, about 0.1% to about 8% by weight, about 0.1% to about 7.5% by weight, about 0.1% to about 7% by weight, about 0.1% to about 6.5% by weight, about 0.1% to about 6% by weight, about 0.1% to about 5.5% by weight, about 0.1% to about 5% by weight, about 0.1% to about 4.5% by weight, about 0.1% to about 4% by weight, about 0.1% to about 3.5% by weight, about 0.1% to about 3% by weight, about 0.1% to about 2.5% by weight, about 0.1% to about 2% by weight, about 0.1% to about 1.5% by weight, about 0.1% to about 1% by weight, about 0.1% to about 0.75% by weight, about 0.1% to about 0.5% by weight, about 0.1% to about 0.25% by weight, about 0.5% to about 7% by weight, about 0.5% to about 6.5% by weight, about 0.5% to about 6% by weight, about 0.5% to about 5.5% by weight, about 0.5% to about 5% by weight, about 0.5% to about 4.5% by weight, about 0.5% to about 4% by weight, about 0.5% to about 3.5% by weight, about 0.5% to about 3% by weight, about 0.5% to about 2.5% by weight, about 0.5% to about 2% by weight, about 0.5% to about 1.5% by weight, about 0.5% to about 1% by weight, about 0.25% to about 10% by weight, about 0.25% to about 9.5% by weight, about 0.25% to about 9% by weight, about 0.25% to about 8.5% by weight, about 0.25% to about 8% by weight, about 0.25% to about 7.5% by weight, about 0.25% to about 7% by weight, about 0.25% to about 6.5% by weight, about 0.25% to about 6% by weight, about 0.25% to about 5.5% by weight, about 0.25% to about 5% by weight, about 0.25% to about 4.5% by weight, about 0.25% to about 4% by weight, about 0.25% to about 3.5% by weight, about 0.25% to about 3% by weight, about 0.25% to about 2.5% by weight, about 0.25% to about 2% by weight, about 0.25% to about 1.5% by weight, about 0.25% to about 1% by weight, about 0.25% to about 0.75% by weight, about 0.25% to about 0.5% by weight, about 0.5% to about 10% by weight, about 0.5% to about 9.5% by weight, about 0.5% to about 9% by weight, about 0.5% to about 8.5% by weight, about 0.5% to about 8% by weight, about 0.5% to about 7.5% by weight, about 0.5% to about 7% by weight, about 0.5% to about 6.5% by weight, about 0.5% to about 6% by weight, about 0.5% to about 5.5% by weight, about 0.5% to about 5% by weight, about 0.5% to about 4.5% by weight, about 0.5% to about 4% by weight, about 0.5% to about 3.5% by weight, about 0.5% to about 3% by weight, about 0.5% to about 2.5% by weight, about 0.5% to about 2% by weight, about 0.5% to about 1.5% by weight, about 0.5% to about 1% by weight, about 0.5% to about 0.75% by weight, about 0.75% to about 10% by weight, about 0.75% to about 9.5% by weight, about 0.75% to about 9% by weight, about 0.75% to about 8.5% by weight, about 0.75% to about 8% by weight, about 0.75% to about 7.5% by weight, about 0.75% to about 7% by weight, about 0.75% to about 6.5% by weight, about 0.75% to about 6% by weight, about 0.75% to about 5.5% by weight, about 0.75% to about 5% by weight, about 0.75% to about 4.5% by weight, about 0.75% to about 4% by weight, about 0.75% to about 3.5% by weight, about 0.75% to about 3% by weight, about 0.75% to about 2.5% by weight, about 0.75% to about 2% by weight, about 0.75% to about 1.5% by weight, about 0.75% to about 1% by weight, about 1% to about 10% by weight, about 1% to about 9.5% by weight, about 1% to about 9% by weight, about 1% to about 8.5% by weight, about 1% to about 8% by weight, about 1% to about 7.5% by weight, about 1% to about 7% by weight, about 1% to about 6.5% by weight, about 1% to about 6% by weight, about 1% to about 5.5% by weight, about 1% to about 5% by weight, about 1% to about 4.5% by weight, about 1% to about 4% by weight, about 1% to about 3.5% by weight, about 1% to about 3% by weight, about 1% to about 2.5% by weight, about 1% to about 2% by weight, about 1% to about 1.5% by weight, about 1.5% to about 10% by weight, about 1.5% to about 9.5% by weight, about 1.5% to about 9% by weight, about 1.5% to about 8.5% by weight, about 1.5% to about 8% by weight, about 1.5% to about 7.5% by weight, about 1.5% to about 7% by weight, about 1.5% to about 6.5% by weight, about 1.5% to about 6% by weight, about 1.5% to about 5.5% by weight, about 1.5% to about 5% by weight, about 1.5% to about 4.5% by weight, about 1.5% to about 4% by weight, about 1.5% to about 3.5% by weight, about 1.5% to about 3% by weight, about 1.5% to about 2.5% by weight, about 1.5% to about 2% by weight, about 2% to about 10% by weight, about 2% to about 9.5% by weight, about 2% to about 9% by weight, about 2% to about 8.5% by weight, about 2% to about 8% by weight, about 2% to about 7.5% by weight, about 2% to about 7% by weight, about 2% to about 6.5% by weight, about 2% to about 6% by weight, about 2% to about 5.5% by weight, about 2% to about 5% by weight, about 2% to about 4.5% by weight, about 2% to about 4% by weight, about 2% to about 3.5% by weight, about 2% to about 3% by weight, about 2% to about 2.5% by weight, about 2.5% to about 10% by weight, about 2.5% to about 9.5% by weight, about 2.5% to about 9% by weight, about 2.5% to about 8.5% by weight, about 2.5% to about 8% by weight, about 2.5% to about 7.5% by weight, about 2.5% to about 7% by weight, about 2.5% to about 6.5% by weight, about 2.5% to about 6% by weight, about 2.5% to about 5.5% by weight, about 2.5% to about 5% by weight, about 2.5% to about 4.5% by weight, about 2.5% to about 4% by weight, about 2.5% to about 3.5% by weight, about 2.5% to about 3% by weight, about 3% to about 10% by weight, about 3% to about 9.5% by weight, about 3% to about 9% by weight, about 3% to about 8.5% by weight, about 3% to about 8% by weight, about 3% to about 7.5% by weight, about 3% to about 7% by weight, about 3% to about 6.5% by weight, about 3% to about 6% by weight, about 3% to about 5.5% by weight, about 3% to about 5% by weight, about 3% to about 4.5% by weight, about 3% to about 4% by weight, about 3% to about 3.5% by weight, about 3.5% to about 7% by weight, about 3.5% to about 10% by weight, about 3.5% to about 9.5% by weight, about 3.5% to about 9% by weight, about 3.5% to about 8.5% by weight, about 3.5% to about 8% by weight, about 3.5% to about 7.5% by weight, about 3.5% to about 6.5% by weight, about 3.5% to about 6% by weight, about 3.5% to about 5.5% by weight, about 3.5% to about 5% by weight, about 3.5% to about 4.5% by weight, about 3.5% to about 4% by weight, about 4% to about 10% by weight, about 4% to about 9.5% by weight, about 4% to about 9% by weight, about 4% to about 8.5% by weight, about 4% to about 8% by weight, about 4% to about 7.5% by weight, about 4% to about 7% by weight, about 4% to about 6.5% by weight, about 4% to about 6% by weight, about 4% to about 5.5% by weight, about 4% to about 5% by weight, about 4% to about 4.5% by weight, about 4.5% to about 10% by weight, about 4.5% to about 9.5% by weight, about 4.5% to about 9% by weight, about 4.5% to about 8.5% by weight, about 4.5% to about 8% by weight, about 4.5% to about 7.5% by weight, about 4.5% to about 7% by weight, about 4.5% to about 6.5% by weight, about 4.5% to about 6% by weight, about 4.5% to about 5.5% by weight, about 4.5% to about 5% by weight, about 5% to about 10% by weight, about 5% to about 9.5% by weight, about 5% to about 9% by weight, about 5% to about 8.5% by weight, about 5% to about 8% by weight, about 5% to about 7.5% by weight, about 5% to about 7% by weight, about 5% to about 6.5% by weight, about 5% to about 6% by weight, about 5% to about 5.5% by weight, about 5.5% to about 10% by weight, about 5.5% to about 9.5% by weight, about 5.5% to about 9% by weight, about 5.5% to about 8.5% by weight, about 5.5% to about 8% by weight, about 5.5% to about 7.5% by weight, about 5.5% to about 7% by weight, about 5.5% to about 6.5% by weight, about 5.5% to about 6% by weight, about 6% to about 10% by weight, about 6% to about 9.5% by weight, about 6% to about 9% by weight, about 6% to about 8.5% by weight, about 6% to about 8% by weight, about 6% to about 7.5% by weight, about 6% to about 7% by weight, about 6% to about 6.5% by weight, about 6.5% to about 10% by weight, about 6.5% to about 9.5% by weight, about 6.5% to about 9% by weight, about 6.5% to about 8.5% by weight, about 6.5% to about 8% by weight, about 6.5% to about 7.5% by weight, about 6.5% to about 7% by weight, about 7% to about 10% by weight, about 7% to about 9.5% by weight, about 7% to about 9% by weight, about 7% to about 8.5% by weight, about 7% to about 8% by weight, about 7% to about 7.5% by weight, about 7.5% to about 10% by weight, about 7.5% to about 9.5% by weight, about 7.5% to about 9% by weight, about 7.5% to about 8.5% by weight, about 7.5% to about 8% by weight, about 8% to about 10% by weight, about 8% to about 9.5% by weight, about 8% to about 9% by weight, about 8% to about 8.5% by weight, about 9% to about 10% by weight, about 9% to about 9.5% by weight, or about 9.5% to about 10% by weight. In certain embodiments, TEA is present in about 0.1% by weight, about 0.25% by weight, about 0.5% by weight, about 0.75% by weight, about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 7% by weight about 7.5% by weight, about 8% by weight, about 8.5% by weight, about 9% by weight, about 9.5% by weight, or about 10% by weight.

In certain embodiments, the emulsifier is present in a range of about 1% to about 25% by weight, about 1% to about 24% by weight, about 1% to about 23% by weight, about 1% to about 22% by weight, about 1% to about 21% by weight, about 1% to about 20% by weight, about 1% to about 19% by weight, about 1% to about 18% by weight, about 1% to about 17% by weight, about 1% to about 16% by weight, about 1% to about 15% by weight, about 1% to about 14% by weight, about 1% to about 13% by weight, about 1% to about 12% by weight, about 1% to about 11% by weight, about 1% to about 10% by weight, about 1% to about 9% by weight, about 1% to about 8% by weight, about 1% to about 7% by weight, about 1% to about 6% by weight, about 1% to about 5% by weight, about 1% to about 4% by weight, about 1% to about 3% by weight, about 1% to about 2% by weight, about 2% to about 25% by weight, about 2% to about 24% by weight, about 2% to about 23% by weight, about 2% to about 22% by weight, about 2% to about 21% by weight, about 2% to about 20% by weight, about 2% to about 19% by weight, about 2% to about 18% by weight, about 2% to about 17% by weight, about 2% to about 16% by weight, about 2% to about 15% by weight, about 2% to about 14% by weight, about 2% to about 13% by weight, about 2% to about 12% by weight, about 2% to about 11% by weight, about 2% to about 10% by weight, about 2% to about 9% by weight, about 2% to about 8% by weight, about 2% to about 7% by weight, about 2% to about 6% by weight, about 2% to about 5% by weight, about 2% to about 4% by weight, about 2% to about 3% by weight, about 3% to about 25% by weight, about 3% to about 24% by weight, about 3% to about 23% by weight, about 3% to about 22% by weight, about 3% to about 21% by weight, about 3% to about 20% by weight, about 3% to about 19% by weight, about 3% to about 18% by weight, about 3% to about 17% by weight, about 3% to about 16% by weight, about 3% to about 15% by weight, about 3% to about 14% by weight, about 3% to about 13% by weight, about 3% to about 12% by weight, about 3% to about 11% by weight, about 3% to about 10% by weight, about 3% to about 9% by weight, about 3% to about 8% by weight, about 3% to about 7% by weight, about 3% to about 6% by weight, about 3% to about 5% by weight, about 3% to about 4% by weight, about 4% to about 25% by weight, about 4% to about 24% by weight, about 4% to about 23% by weight, about 4% to about 22% by weight, about 4% to about 21% by weight, about 4% to about 20% by weight, about 4% to about 19% by weight, about 4% to about 18% by weight, about 4% to about 17% by weight, about 4% to about 16% by weight, about 4% to about 15% by weight, about 4% to about 14% by weight, about 4% to about 13% by weight, about 4% to about 12% by weight, about 4% to about 11% by weight, about 4% to about 10% by weight, about 4% to about 9% by weight, about 4% to about 8% by weight, about 4% to about 7% by weight, about 4% to about 6% by weight, about 4% to about 5% by weight, about 5% to about 25% by weight, about 5% to about 24% by weight, about 5% to about 23% by weight, about 5% to about 22% by weight, about 5% to about 21% by weight, about 5% to about 20% by weight, about 5% to about 19% by weight, about 5% to about 18% by weight, about 5% to about 17% by weight, about 5% to about 16% by weight, about 5% to about 15% by weight, about 5% to about 14% by weight, about 5% to about 13% by weight, about 5% to about 12% by weight, about 5% to about 11% by weight, about 5% to about 10% by weight, about 5% to about 9% by weight, about 5% to about 8% by weight, about 5% to about 7% by weight, about 5% to about 6% by weight, about 6% to about 25% by weight, about 6% to about 24% by weight, about 6% to about 23% by weight, about 6% to about 22% by weight, about 6% to about 21% by weight, about 6% to about 20% by weight, about 6% to about 19% by weight, about 6% to about 18% by weight, about 6% to about 17% by weight, about 6% to about 16% by weight, about 6% to about 15% by weight, about 6% to about 14% by weight, about 6% to about 13% by weight, about 6% to about 12% by weight, about 6% to about 11% by weight, about 6% to about 10% by weight, about 6% to about 9% by weight, about 6% to about 8% by weight, about 6% to about 7% by weight, about 7% to about 25% by weight, about 7% to about 24% by weight, about 7% to about 23% by weight, about 7% to about 22% by weight, about 7% to about 21% by weight, about 7% to about 20% by weight, about 7% to about 19% by weight, about 7% to about 18% by weight, about 7% to about 17% by weight, about 7% to about 16% by weight, about 7% to about 15% by weight, about 7% to about 14% by weight, about 7% to about 13% by weight, about 7% to about 12% by weight, about 7% to about 11% by weight, about 7% to about 10% by weight, about 7% to about 9% by weight, about 7% to about 8% by weight, about 8% to about 25% by weight, about 8% to about 24% by weight, about 8% to about 23% by weight, about 8% to about 22% by weight, about 8% to about 21% by weight, about 8% to about 20% by weight, about 8% to about 19% by weight, about 8% to about 18% by weight, about 8% to about 17% by weight, about 8% to about 16% by weight, about 8% to about 15% by weight, about 8% to about 14% by weight, about 8% to about 13% by weight, about 8% to about 12% by weight, about 8% to about 11% by weight, about 8% to about 10% by weight, about 8% to about 9% by weight, about 9% to about 25% by weight, about 9% to about 24% by weight, about 9% to about 23% by weight, about 9% to about 22% by weight, about 9% to about 21% by weight, about 9% to about 20% by weight, about 9% to about 19% by weight, about 9% to about 18% by weight, about 9% to about 17% by weight, about 9% to about 16% by weight, about 9% to about 15% by weight, about 9% to about 14% by weight, about 9% to about 13% by weight, about 9% to about 12% by weight, about 9% to about 11% by weight, about 9% to about 10% by weight, about 10% to about 25% by weight, about 10% to about 24% by weight, about 10% to about 23% by weight, about 10% to about 22% by weight, about 10% to about 21% by weight, about 10% to about 20% by weight, about 10% to about 19% by weight, about 10% to about 18% by weight, about 10% to about 17% by weight, about 10% to about 16% by weight, about 10% to about 15% by weight, about 10% to about 14% by weight, about 10% to about 13% by weight, about 10% to about 12% by weight, about 10% to about 11% by weight, about 11% to about 25% by weight, about 11% to about 24% by weight, about 11% to about 23% by weight, about 11% to about 22% by weight, about 11% to about 21% by weight, about 11% to about 20% by weight, about 11% to about 19% by weight, about 11% to about 18% by weight, about 11% to about 17% by weight, about 11% to about 16% by weight, about 11% to about 15% by weight, about 11% to about 14% by weight, about 11% to about 13% by weight, about 11% to about 12% by weight, about 12% to about 25% by weight, about 12% to about 24% by weight, about 12% to about 23% by weight, about 12% to about 22% by weight, about 12% to about 21% by weight, about 12% to about 20% by weight, about 12% to about 19% by weight, about 12% to about 18% by weight, about 12% to about 17% by weight, about 12% to about 16% by weight, about 12% to about 15% by weight, about 12% to about 14% by weight, about 12% to about 13% by weight, about 13% to about 25% by weight, about 13% to about 24% by weight, about 13% to about 23% by weight, about 13% to about 22% by weight, about 13% to about 21% by weight, about 13% to about 20% by weight, about 13% to about 19% by weight, about 13% to about 18% by weight, about 13% to about 17% by weight, about 13% to about 16% by weight, about 13% to about 15% by weight, about 13% to about 14% by weight, about 14% to about 25% by weight, about 14% to about 24% by weight, about 14% to about 23% by weight, about 14% to about 22% by weight, about 14% to about 21% by weight, about 14% to about 20% by weight, about 14% to about 19% by weight, about 14% to about 18% by weight, about 14% to about 17% by weight, about 14% to about 16% by weight, about 14% to about 15% by weight, about 15% to about 25% by weight, about 15% to about 24% by weight, about 15% to about 23% by weight, about 15% to about 22% by weight, about 15% to about 21% by weight, about 15% to about 20% by weight, about 15% to about 19% by weight, about 15% to about 18% by weight, about 15% to about 17% by weight, about 15% to about 16% by weight, about 16% to about 25% by weight, about 16% to about 24% by weight, about 16% to about 23% by weight, about 16% to about 22% by weight, about 16% to about 21% by weight, about 16% to about 20% by weight, about 16% to about 19% by weight, about 16% to about 18% by weight, about 16% to about 17% by weight, about 17% to about 25% by weight, about 17% to about 24% by weight, about 17% to about 23% by weight, about 17% to about 22% by weight, about 17% to about 21% by weight, about 17% to about 20% by weight, about 17% to about 19% by weight, about 17% to about 18% by weight, about 18% to about 25% by weight, about 18% to about 24% by weight, about 18% to about 23% by weight, about 18% to about 22% by weight, about 18% to about 21% by weight, about 18% to about 20% by weight, about 18% to about 19% by weight, about 19% to about 25% by weight, about 19% to about 24% by weight, about 19% to about 23% by weight, about 19% to about 22% by weight, about 19% to about 21% by weight, about 19% to about 20% by weight, about 20% to about 25% by weight, about 20% to about 24% by weight, about 20% to about 23% by weight, about 20% to about 22% by weight, about 20% to about 21% by weight, about 21% to about 25% by weight, about 21% to about 24% by weight, about 21% to about 23% by weight, about 21% to about 22% by weight, about 22% to about 25% by weight, about 22% to about 24% by weight, about 22% to about 23% by weight, about 23% to about 25% by weight, about 23% to about 24% by weight, or about 24% to about 25% by weight. In certain embodiments, the emulsifier is present in about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 6.5% by weight, about 7% by weight, about 7.5% by weight, about 8% by weight, about 8.5% by weight, about 9% by weight, about 9.5% by weight, about 10% by weight, about 10.5% by weight, about 11% by weight, about 11.5% by weight, about 12% by weight, about 12.5% by weight, about 13% by weight, about 13.5% by weight, about 14% by weight, about 14.5% by weight, about 15% by weight, about 15.5% by weight, about 16% by weight, about 16.5% by weight, about 17% by weight, about 17.5% by weight, about 18% by weight, about 18.5% by weight, about 19% by weight, about 19.5% by weight, about 20% by weight, about 20.5% by weight, about 21% by weight, about 21.5% by weight, about 22% by weight, about 22.5% by weight, about 23% by weight, about 23.5% by weight, about 24% by weight, about 24.5% by weight, or about 25% by weight.

In additional embodiments, the oil is present in a range of about 1% to about 50% by weight, about 1% to about 49% by weight, about 1% to about 48% by weight, about 1% to about 47% by weight, about 1% to about 46% by weight, about 1% to about 45% by weight, about 1% to about 44% by weight, about 1% to about 43% by weight, about 1% to about 42% by weight, about 1% to about 41% by weight, about 1% to about 40% by weight, about 1% to about 39% by weight, about 1% to about 38% by weight, about 1% to about 37% by weight, about 1% to about 36% by weight, about 1% to about 35% by weight, about 1% to about 34% by weight, about 1% to about 33% by weight, about 1% to about 32% by weight, about 1% to about 31% by weight, about 1% to about 30% by weight, about 1% to about 29% by weight, about 1% to about 28% by weight, about 1% to about 27% by weight, about 1% to about 26% by weight, about 1% to about 25% by weight, about 1% to about 24% by weight, about 1% to about 23% by weight, about 1% to about 22% by weight, about 1% to about 21% by weight, about 1% to about 20% by weight, about 1% to about 19% by weight, about 1% to about 18% by weight, about 1% to about 17% by weight, about 1% to about 16% by weight, about 1% to about 15% by weight, about 1% to about 14% by weight, about 1% to about 13% by weight, about 1% to about 12% by weight, about 1% to about 11% by weight, about 1% to about 10% by weight, about 1% to about 9% by weight, about 1% to about 8% by weight, about 1% to about 7% by weight, about 1% to about 6% by weight, about 1% to about 5% by weight, about 1% to about 4% by weight, about 1% to about 3% by weight, about 1% to about 2% by weight, about 2% to about 50% by weight, about 2% to about 49% by weight, about 2% to about 48% by weight, about 2% to about 47% by weight, about 2% to about 46% by weight, about 2% to about 45% by weight, about 2% to about 44% by weight, about 2% to about 43% by weight, about 2% to about 42% by weight, about 2% to about 41% by weight, about 2% to about 40% by weight, about 2% to about 39% by weight, about 2% to about 38% by weight, about 2% to about 37% by weight, about 2% to about 36% by weight, about 2% to about 35% by weight, about 2% to about 34% by weight, about 2% to about 33% by weight, about 2% to about 32% by weight, about 2% to about 31% by weight, about 2% to about 30% by weight, about 2% to about 29% by weight, about 2% to about 28% by weight, about 2% to about 27% by weight, about 2% to about 26% by weight, about 2% to about 25% by weight, about 2% to about 24% by weight, about 2% to about 23% by weight, about 2% to about 22% by weight, about 2% to about 21% by weight, about 2% to about 20% by weight, about 2% to about 19% by weight, about 2% to about 18% by weight, about 2% to about 17% by weight, about 2% to about 16% by weight, about 2% to about 15% by weight, about 2% to about 14% by weight, about 2% to about 13% by weight, about 2% to about 12% by weight, about 2% to about 11% by weight, about 2% to about 10% by weight, about 2% to about 9% by weight, about 2% to about 8% by weight, about 2% to about 7% by weight, about 2% to about 6% by weight, about 2% to about 5% by weight, about 2% to about 4% by weight, about 2% to about 3% by weight, about 3% to about 50% by weight, about 3% to about 49% by weight, about 3% to about 48% by weight, about 3% to about 47% by weight, about 3% to about 46% by weight, about 3% to about 45% by weight, about 3% to about 44% by weight, about 3% to about 43% by weight, about 3% to about 42% by weight, about 3% to about 41% by weight, about 3% to about 40% by weight, about 3% to about 39% by weight, about 3% to about 38% by weight, about 3% to about 37% by weight, about 3% to about 36% by weight, about 3% to about 35% by weight, about 3% to about 34% by weight, about 3% to about 33% by weight, about 3% to about 32% by weight, about 3% to about 31% by weight, about 3% to about 30% by weight, about 3% to about 29% by weight, about 3% to about 28% by weight, about 3% to about 27% by weight, about 3% to about 26% by weight, about 3% to about 25% by weight, about 3% to about 24% by weight, about 3% to about 23% by weight, about 3% to about 22% by weight, about 3% to about 21% by weight, about 3% to about 20% by weight, about 3% to about 19% by weight, about 3% to about 18% by weight, about 3% to about 17% by weight, about 3% to about 16% by weight, about 3% to about 15% by weight, about 3% to about 14% by weight, about 3% to about 13% by weight, about 3% to about 12% by weight, about 3% to about 11% by weight, about 3% to about 10% by weight, about 3% to about 9% by weight, about 3% to about 8% by weight, about 3% to about 7% by weight, about 3% to about 6% by weight, about 3% to about 5% by weight, about 3% to about 4% by weight, about 4% to about 50% by weight, about 4% to about 49% by weight, about 4% to about 48% by weight, about 4% to about 47% by weight, about 4% to about 46% by weight, about 4% to about 45% by weight, about 4% to about 44% by weight, about 4% to about 43% by weight, about 4% to about 42% by weight, about 4% to about 41% by weight, about 4% to about 40% by weight, about 4% to about 39% by weight, about 4% to about 38% by weight, about 4% to about 37% by weight, about 4% to about 36% by weight, about 4% to about 35% by weight, about 4% to about 34% by weight, about 4% to about 33% by weight, about 4% to about 32% by weight, about 4% to about 31% by weight, about 4% to about 30% by weight, about 4% to about 29% by weight, about 4% to about 28% by weight, about 4% to about 27% by weight, about 4% to about 26% by weight, about 4% to about 25% by weight, about 4% to about 24% by weight, about 4% to about 23% by weight, about 4% to about 22% by weight, about 4% to about 21% by weight, about 4% to about 20% by weight, about 4% to about 19% by weight, about 4% to about 18% by weight, about 4% to about 17% by weight, about 4% to about 16% by weight, about 4% to about 15% by weight, about 4% to about 14% by weight, about 4% to about 13% by weight, about 4% to about 12% by weight, about 4% to about 11% by weight, about 4% to about 10% by weight, about 4% to about 9% by weight, about 4% to about 8% by weight, about 4% to about 7% by weight, about 4% to about 6% by weight, about 4% to about 5% by weight, about 5% to about 50% by weight, about 5% to about 49% by weight, about 5% to about 48% by weight, about 5% to about 47% by weight, about 5% to about 46% by weight, about 5% to about 45% by weight, about 5% to about 44% by weight, about 5% to about 43% by weight, about 5% to about 42% by weight, about 5% to about 41% by weight, about 5% to about 40% by weight, about 5% to about 39% by weight, about 5% to about 38% by weight, about 5% to about 37% by weight, about 5% to about 36% by weight, about 5% to about 35% by weight, about 5% to about 34% by weight, about 5% to about 33% by weight, about 5% to about 32% by weight, about 5% to about 31% by weight, about 5% to about 30% by weight, about 5% to about 29% by weight, about 5% to about 28% by weight, about 5% to about 27% by weight, about 5% to about 26% by weight, about 5% to about 25% by weight, about 5% to about 24% by weight, about 5% to about 23% by weight, about 5% to about 22% by weight, about 5% to about 21% by weight, about 5% to about 20% by weight, about 5% to about 19% by weight, about 5% to about 18% by weight, about 5% to about 17% by weight, about 5% to about 16% by weight, about 5% to about 15% by weight, about 5% to about 14% by weight, about 5% to about 13% by weight, about 5% to about 12% by weight, about 5% to about 11% by weight, about 5% to about 10% by weight, about 5% to about 9% by weight, about 5% to about 8% by weight, about 5% to about 7% by weight, about 5% to about 6% by weight, about 6% to about 50% by weight, about 6% to about 49% by weight, about 6% to about 48% by weight, about 6% to about 47% by weight, about 6% to about 46% by weight, about 6% to about 45% by weight, about 6% to about 44% by weight, about 6% to about 43% by weight, about 6% to about 42% by weight, about 6% to about 41% by weight, about 6% to about 40% by weight, about 6% to about 39% by weight, about 6% to about 38% by weight, about 6% to about 37% by weight, about 6% to about 36% by weight, about 6% to about 35% by weight, about 6% to about 34% by weight, about 6% to about 33% by weight, about 6% to about 32% by weight, about 6% to about 31% by weight, about 6% to about 30% by weight, about 6% to about 29% by weight, about 6% to about 28% by weight, about 6% to about 27% by weight, about 6% to about 26% by weight, about 6% to about 25% by weight, about 6% to about 24% by weight, about 6% to about 23% by weight, about 6% to about 22% by weight, about 6% to about 21% by weight, about 6% to about 20% by weight, about 6% to about 19% by weight, about 6% to about 18% by weight, about 6% to about 17% by weight, about 6% to about 16% by weight, about 6% to about 15% by weight, about 6% to about 14% by weight, about 6% to about 13% by weight, about 6% to about 12% by weight, about 6% to about 11% by weight, about 6% to about 10% by weight, about 6% to about 9% by weight, about 6% to about 8% by weight, about 6% to about 7% by weight, about 7% to about 50% by weight, about 7% to about 49% by weight, about 7% to about 48% by weight, about 7% to about 47% by weight, about 7% to about 46% by weight, about 7% to about 45% by weight, about 7% to about 44% by weight, about 7% to about 43% by weight, about 7% to about 42% by weight, about 7% to about 41% by weight, about 7% to about 40% by weight, about 7% to about 39% by weight, about 7% to about 38% by weight, about 7% to about 37% by weight, about 7% to about 36% by weight, about 7% to about 35% by weight, about 7% to about 34% by weight, about 7% to about 33% by weight, about 7% to about 32% by weight, about 7% to about 31% by weight, about 7% to about 30% by weight, about 7% to about 29% by weight, about 7% to about 28% by weight, about 7% to about 27% by weight, about 7% to about 26% by weight, about 7% to about 25% by weight, about 7% to about 24% by weight, about 7% to about 23% by weight, about 7% to about 22% by weight, about 7% to about 21% by weight, about 7% to about 20% by weight, about 7% to about 19% by weight, about 7% to about 18% by weight, about 7% to about 17% by weight, about 7% to about 16% by weight, about 7% to about 15% by weight, about 7% to about 14% by weight, about 7% to about 13% by weight, about 7% to about 12% by weight, about 7% to about 11% by weight, about 7% to about 10% by weight, about 7% to about 9% by weight, about 7% to about 8% by weight, about 8% to about 50% by weight, about 8% to about 49% by weight, about 8% to about 48% by weight, about 8% to about 47% by weight, about 8% to about 46% by weight, about 8% to about 45% by weight, about 8% to about 44% by weight, about 8% to about 43% by weight, about 8% to about 42% by weight, about 8% to about 41% by weight, about 8% to about 40% by weight, about 8% to about 39% by weight, about 8% to about 38% by weight, about 8% to about 37% by weight, about 8% to about 36% by weight, about 8% to about 35% by weight, about 8% to about 34% by weight, about 8% to about 33% by weight, about 8% to about 32% by weight, about 8% to about 31% by weight, about 8% to about 30% by weight, about 8% to about 29% by weight, about 8% to about 28% by weight, about 8% to about 27% by weight, about 8% to about 26% by weight, about 8% to about 25% by weight, about 8% to about 24% by weight, about 8% to about 23% by weight, about 8% to about 22% by weight, about 8% to about 21% by weight, about 8% to about 20% by weight, about 8% to about 19% by weight, about 8% to about 18% by weight, about 8% to about 17% by weight, about 8% to about 16% by weight, about 8% to about 15% by weight, about 8% to about 14% by weight, about 8% to about 13% by weight, about 8% to about 12% by weight, about 8% to about 11% by weight, about 8% to about 10% by weight, about 8% to about 9% by weight, about 9% to about 50% by weight, about 9% to about 49% by weight, about 9% to about 48% by weight, about 9% to about 47% by weight, about 9% to about 46% by weight, about 9% to about 45% by weight, about 9% to about 44% by weight, about 9% to about 43% by weight, about 9% to about 42% by weight, about 9% to about 41% by weight, about 9% to about 40% by weight, about 9% to about 39% by weight, about 9% to about 38% by weight, about 9% to about 37% by weight, about 9% to about 36% by weight, about 9% to about 35% by weight, about 9% to about 34% by weight, about 9% to about 33% by weight, about 9% to about 32% by weight, about 9% to about 31% by weight, about 9% to about 30% by weight, about 9% to about 29% by weight, about 9% to about 28% by weight, about 9% to about 27% by weight, about 9% to about 26% by weight, about 9% to about 25% by weight, about 9% to about 24% by weight, about 9% to about 23% by weight, about 9% to about 22% by weight, about 9% to about 21% by weight, about 9% to about 20% by weight, about 9% to about 19% by weight, about 9% to about 18% by weight, about 9% to about 17% by weight, about 9% to about 16% by weight, about 9% to about 15% by weight, about 9% to about 14% by weight, about 9% to about 13% by weight, about 9% to about 12% by weight, about 9% to about 11% by weight, about 9% to about 10% by weight, about 10% to about 50% by weight, about 10% to about 49% by weight, about 10% to about 48% by weight, about 10% to about 47% by weight, about 10% to about 46% by weight, about 10% to about 45% by weight, about 10% to about 44% by weight, about 10% to about 43% by weight, about 10% to about 42% by weight, about 10% to about 41% by weight, about 10% to about 40% by weight, about 10% to about 39% by weight, about 10% to about 38% by weight, about 10% to about 37% by weight, about 10% to about 36% by weight, about 10% to about 35% by weight, about 10% to about 34% by weight, about 10% to about 33% by weight, about 10% to about 32% by weight, about 10% to about 31% by weight, about 10% to about 30% by weight, about 10% to about 29% by weight, about 10% to about 28% by weight, about 10% to about 27% by weight, about 10% to about 26% by weight, about 10% to about 25% by weight, about 10% to about 24% by weight, about 10% to about 23% by weight, about 10% to about 22% by weight, about 10% to about 21% by weight, about 10% to about 20% by weight, about 10% to about 19% by weight, about 10% to about 18% by weight, about 10% to about 17% by weight, about 10% to about 16% by weight, about 10% to about 15% by weight, about 10% to about 14% by weight, about 10% to about 13% by weight, about 10% to about 12% by weight, about 10% to about 11% by weight, about 11% to about 50% by weight, about 11% to about 49% by weight, about 11% to about 48% by weight, about 11% to about 47% by weight, about 11% to about 46% by weight, about 11% to about 45% by weight, about 11% to about 44% by weight, about 11% to about 43% by weight, about 11% to about 42% by weight, about 11% to about 41% by weight, about 11% to about 40% by weight, about 11% to about 39% by weight, about 11% to about 38% by weight, about 11% to about 37% by weight, about 11% to about 36% by weight, about 11% to about 35% by weight, about 11% to about 34% by weight, about 11% to about 33% by weight, about 11% to about 32% by weight, about 11% to about 31% by weight, about 11% to about 30% by weight, about 11% to about 29% by weight, about 11% to about 28% by weight, about 11% to about 27% by weight, about 11% to about 26% by weight, about 11% to about 25% by weight, about 11% to about 24% by weight, about 11% to about 23% by weight, about 11% to about 22% by weight, about 11% to about 21% by weight, about 11% to about 20% by weight, about 11% to about 19% by weight, about 11% to about 18% by weight, about 11% to about 17% by weight, about 11% to about 16% by weight, about 11% to about 15% by weight, about 11% to about 14% by weight, about 11% to about 13% by weight, about 11% to about 12% by weight, about 12% to about 50% by weight, about 12% to about 49% by weight, about 12% to about 48% by weight, about 12% to about 47% by weight, about 12% to about 46% by weight, about 12% to about 45% by weight, about 12% to about 44% by weight, about 12% to about 43% by weight, about 12% to about 42% by weight, about 12% to about 41% by weight, about 12% to about 40% by weight, about 12% to about 39% by weight, about 12% to about 38% by weight, about 12% to about 37% by weight, about 12% to about 36% by weight, about 12% to about 35% by weight, about 12% to about 34% by weight, about 12% to about 33% by weight, about 12% to about 32% by weight, about 12% to about 31% by weight, about 12% to about 30% by weight, about 12% to about 29% by weight, about 12% to about 28% by weight, about 12% to about 27% by weight, about 12% to about 26% by weight, about 12% to about 25% by weight, about 12% to about 24% by weight, about 12% to about 23% by weight, about 12% to about 22% by weight, about 12% to about 21% by weight, about 12% to about 20% by weight, about 12% to about 19% by weight, about 12% to about 18% by weight, about 12% to about 17% by weight, about 12% to about 16% by weight, about 12% to about 15% by weight, about 12% to about 14% by weight, about 12% to about 13% by weight, about 13% to about 50% by weight, about 13% to about 49% by weight, about 13% to about 48% by weight, about 13% to about 47% by weight, about 13% to about 46% by weight, about 13% to about 45% by weight, about 13% to about 44% by weight, about 13% to about 43% by weight, about 13% to about 42% by weight, about 13% to about 41% by weight, about 13% to about 40% by weight, about 13% to about 39% by weight, about 13% to about 38% by weight, about 13% to about 37% by weight, about 13% to about 36% by weight, about 13% to about 35% by weight, about 13% to about 34% by weight, about 13% to about 33% by weight, about 13% to about 32% by weight, about 13% to about 31% by weight, about 13% to about 30% by weight, about 13% to about 29% by weight, about 13% to about 28% by weight, about 13% to about 27% by weight, about 13% to about 26% by weight, about 13% to about 25% by weight, about 13% to about 24% by weight, about 13% to about 23% by weight, about 13% to about 22% by weight, about 13% to about 21% by weight, about 13% to about 20% by weight, about 13% to about 19% by weight, about 13% to about 18% by weight, about 13% to about 17% by weight, about 13% to about 16% by weight, about 13% to about 15% by weight, about 13% to about 14% by weight, about 14% to about 50% by weight, about 14% to about 49% by weight, about 14% to about 48% by weight, about 14% to about 47% by weight, about 14% to about 46% by weight, about 14% to about 45% by weight, about 14% to about 44% by weight, about 14% to about 43% by weight, about 14% to about 42% by weight, about 14% to about 41% by weight, about 14% to about 40% by weight, about 14% to about 39% by weight, about 14% to about 38% by weight, about 14% to about 37% by weight, about 14% to about 36% by weight, about 14% to about 35% by weight, about 14% to about 34% by weight, about 14% to about 33% by weight, about 14% to about 32% by weight, about 14% to about 31% by weight, about 14% to about 30% by weight, about 14% to about 29% by weight, about 14% to about 28% by weight, about 14% to about 27% by weight, about 14% to about 26% by weight, about 14% to about 25% by weight, about 14% to about 24% by weight, about 14% to about 23% by weight, about 14% to about 22% by weight, about 14% to about 21% by weight, about 14% to about 20% by weight, about 14% to about 19% by weight, about 14% to about 18% by weight, about 14% to about 17% by weight, about 14% to about 16% by weight, about 14% to about 15% by weight, about 15% to about 50% by weight, about 15% to about 49% by weight, about 15% to about 48% by weight, about 15% to about 47% by weight, about 15% to about 46% by weight, about 15% to about 45% by weight, about 15% to about 44% by weight, about 15% to about 43% by weight, about 15% to about 42% by weight, about 15% to about 41% by weight, about 15% to about 40% by weight, about 15% to about 39% by weight, about 15% to about 38% by weight, about 15% to about 37% by weight, about 15% to about 36% by weight, about 15% to about 35% by weight, about 15% to about 34% by weight, about 15% to about 33% by weight, about 15% to about 32% by weight, about 15% to about 31% by weight, about 15% to about 30% by weight, about 15% to about 29% by weight, about 15% to about 28% by weight, about 15% to about 27% by weight, about 15% to about 26% by weight, about 15% to about 25% by weight, about 15% to about 24% by weight, about 15% to about 23% by weight, about 15% to about 22% by weight, about 15% to about 21% by weight, about 15% to about 20% by weight, about 15% to about 19% by weight, about 15% to about 18% by weight, about 15% to about 17% by weight, about 15% to about 16% by weight, about 16% to about 50% by weight, about 16% to about 49% by weight, about 16% to about 48% by weight, about 16% to about 47% by weight, about 16% to about 46% by weight, about 16% to about 45% by weight, about 16% to about 44% by weight, about 16% to about 43% by weight, about 16% to about 42% by weight, about 16% to about 41% by weight, about 16% to about 40% by weight, about 16% to about 39% by weight, about 16% to about 38% by weight, about 16% to about 37% by weight, about 16% to about 36% by weight, about 16% to about 35% by weight, about 16% to about 34% by weight, about 16% to about 33% by weight, about 16% to about 32% by weight, about 16% to about 31% by weight, about 16% to about 30% by weight, about 16% to about 29% by weight, about 16% to about 28% by weight, about 16% to about 27% by weight, about 16% to about 26% by weight, about 16% to about 25% by weight, about 16% to about 24% by weight, about 16% to about 23% by weight, about 16% to about 22% by weight, about 16% to about 21% by weight, about 16% to about 20% by weight, about 16% to about 19% by weight, about 16% to about 18% by weight, about 16% to about 17% by weight, about 17% to about 50% by weight, about 17% to about 49% by weight, about 17% to about 48% by weight, about 17% to about 47% by weight, about 17% to about 46% by weight, about 17% to about 45% by weight, about 17% to about 44% by weight, about 17% to about 43% by weight, about 17% to about 42% by weight, about 17% to about 41% by weight, about 17% to about 40% by weight, about 17% to about 39% by weight, about 17% to about 38% by weight, about 17% to about 37% by weight, about 17% to about 36% by weight, about 17% to about 35% by weight, about 17% to about 34% by weight, about 17% to about 33% by weight, about 17% to about 32% by weight, about 17% to about 31% by weight, about 17% to about 30% by weight, about 17% to about 29% by weight, about 17% to about 28% by weight, about 17% to about 27% by weight, about 17% to about 26% by weight, about 17% to about 25% by weight, about 17% to about 24% by weight, about 17% to about 23% by weight, about 17% to about 22% by weight, about 17% to about 21% by weight, about 17% to about 20% by weight, about 17% to about 19% by weight, about 17% to about 18% by weight, about 18% to about 50% by weight, about 18% to about 49% by weight, about 18% to about 48% by weight, about 18% to about 47% by weight, about 18% to about 46% by weight, about 18% to about 45% by weight, about 18% to about 44% by weight, about 18% to about 43% by weight, about 18% to about 42% by weight, about 18% to about 41% by weight, about 18% to about 40% by weight, about 18% to about 39% by weight, about 18% to about 38% by weight, about 18% to about 37% by weight, about 18% to about 36% by weight, about 18% to about 35% by weight, about 18% to about 34% by weight, about 18% to about 33% by weight, about 18% to about 32% by weight, about 18% to about 31% by weight, about 18% to about 30% by weight, about 18% to about 29% by weight, about 18% to about 28% by weight, about 18% to about 27% by weight, about 18% to about 26% by weight, about 18% to about 25% by weight, about 18% to about 24% by weight, about 18% to about 23% by weight, about 18% to about 22% by weight, about 18% to about 21% by weight, about 18% to about 20% by weight, about 18% to about 19% by weight, about 19% to about 50% by weight, about 19% to about 49% by weight, about 19% to about 48% by weight, about 19% to about 47% by weight, about 19% to about 46% by weight, about 19% to about 45% by weight, about 19% to about 44% by weight, about 19% to about 43% by weight, about 19% to about 42% by weight, about 19% to about 41% by weight, about 19% to about 40% by weight, about 19% to about 39% by weight, about 19% to about 38% by weight, about 19% to about 37% by weight, about 19% to about 36% by weight, about 19% to about 35% by weight, about 19% to about 34% by weight, about 19% to about 33% by weight, about 19% to about 32% by weight, about 19% to about 31% by weight, about 19% to about 30% by weight, about 19% to about 29% by weight, about 19% to about 28% by weight, about 19% to about 27% by weight, about 19% to about 26% by weight, about 19% to about 25% by weight, about 19% to about 24% by weight, about 19% to about 23% by weight, about 19% to about 22% by weight, about 19% to about 21% by weight, about 19% to about 20% by weight, about 20% to about 50% by weight, about 20% to about 49% by weight, about 20% to about 48% by weight, about 20% to about 47% by weight, about 20% to about 46% by weight, about 20% to about 45% by weight, about 20% to about 44% by weight, about 20% to about 43% by weight, about 20% to about 42% by weight, about 20% to about 41% by weight, about 20% to about 40% by weight, about 20% to about 39% by weight, about 20% to about 38% by weight, about 20% to about 37% by weight, about 20% to about 36% by weight, about 20% to about 35% by weight, about 20% to about 34% by weight, about 20% to about 33% by weight, about 20% to about 32% by weight, about 20% to about 31% by weight, about 20% to about 30% by weight, about 20% to about 29% by weight, about 20% to about 28% by weight, about 20% to about 27% by weight, about 20% to about 26% by weight, about 20% to about 25% by weight, about 20% to about 24% by weight, about 20% to about 23% by weight, about 20% to about 22% by weight, about 20% to about 21% by weight, about 21% to about 50% by weight, about 21% to about 49% by weight, about 21% to about 48% by weight, about 21% to about 47% by weight, about 21% to about 46% by weight, about 21% to about 45% by weight, about 21% to about 44% by weight, about 21% to about 43% by weight, about 21% to about 42% by weight, about 21% to about 41% by weight, about 21% to about 40% by weight, about 21% to about 39% by weight, about 21% to about 38% by weight, about 21% to about 37% by weight, about 21% to about 36% by weight, about 21% to about 35% by weight, about 21% to about 34% by weight, about 21% to about 33% by weight, about 21% to about 32% by weight, about 21% to about 31% by weight, about 21% to about 30% by weight, about 21% to about 29% by weight, about 21% to about 28% by weight, about 21% to about 27% by weight, about 21% to about 26% by weight, about 21% to about 25% by weight, about 21% to about 24% by weight, about 21% to about 23% by weight, about 21% to about 22% by weight, about 22% to about 50% by weight, about 22% to about 49% by weight, about 22% to about 48% by weight, about 22% to about 47% by weight, about 22% to about 46% by weight, about 22% to about 45% by weight, about 22% to about 44% by weight, about 22% to about 43% by weight, about 22% to about 42% by weight, about 22% to about 41% by weight, about 22% to about 40% by weight, about 22% to about 39% by weight, about 22% to about 38% by weight, about 22% to about 37% by weight, about 22% to about 36% by weight, about 22% to about 35% by weight, about 22% to about 34% by weight, about 22% to about 33% by weight, about 22% to about 32% by weight, about 22% to about 31% by weight, about 22% to about 30% by weight, about 22% to about 29% by weight, about 22% to about 28% by weight, about 22% to about 27% by weight, about 22% to about 26% by weight, about 22% to about 25% by weight, about 22% to about 24% by weight, about 22% to about 23% by weight, about 23% to about 50% by weight, about 23% to about 49% by weight, about 23% to about 48% by weight, about 23% to about 47% by weight, about 23% to about 46% by weight, about 23% to about 45% by weight, about 23% to about 44% by weight, about 23% to about 43% by weight, about 23% to about 42% by weight, about 23% to about 41% by weight, about 23% to about 40% by weight, about 23% to about 39% by weight, about 23% to about 38% by weight, about 23% to about 37% by weight, about 23% to about 36% by weight, about 23% to about 35% by weight, about 23% to about 34% by weight, about 23% to about 33% by weight, about 23% to about 32% by weight, about 23% to about 31% by weight, about 23% to about 30% by weight, about 23% to about 29% by weight, about 23% to about 28% by weight, about 23% to about 27% by weight, about 23% to about 26% by weight, about 23% to about 25% by weight, about 23% to about 24% by weight, about 24% to about 50% by weight, about 24% to about 49% by weight, about 24% to about 48% by weight, about 24% to about 47% by weight, about 24% to about 46% by weight, about 24% to about 45% by weight, about 24% to about 44% by weight, about 24% to about 43% by weight, about 24% to about 42% by weight, about 24% to about 41% by weight, about 24% to about 40% by weight, about 24% to about 39% by weight, about 24% to about 38% by weight, about 24% to about 37% by weight, about 24% to about 36% by weight, about 24% to about 35% by weight, about 24% to about 34% by weight, about 24% to about 33% by weight, about 24% to about 32% by weight, about 24% to about 31% by weight, about 24% to about 30% by weight, about 24% to about 29% by weight, about 24% to about 28% by weight, about 24% to about 27% by weight, about 24% to about 26% by weight, about 24% to about 25% by weight, about 25% to about 50% by weight, about 25% to about 49% by weight, about 25% to about 48% by weight, about 25% to about 47% by weight, about 25% to about 46% by weight, about 25% to about 45% by weight, about 25% to about 44% by weight, about 25% to about 43% by weight, about 25% to about 42% by weight, about 25% to about 41% by weight, about 25% to about 40% by weight, about 25% to about 39% by weight, about 25% to about 38% by weight, about 25% to about 37% by weight, about 25% to about 36% by weight, about 25% to about 35% by weight, about 25% to about 34% by weight, about 25% to about 33% by weight, about 25% to about 32% by weight, about 25% to about 31% by weight, about 25% to about 30% by weight, about 25% to about 29% by weight, about 25% to about 28% by weight, about 25% to about 27% by weight, about 25% to about 26% by weight, about 26% to about 50% by weight, about 26% to about 49% by weight, about 26% to about 48% by weight, about 26% to about 47% by weight, about 26% to about 46% by weight, about 26% to about 45% by weight, about 26% to about 44% by weight, about 26% to about 43% by weight, about 26% to about 42% by weight, about 26% to about 41% by weight, about 26% to about 40% by weight, about 26% to about 39% by weight, about 26% to about 38% by weight, about 26% to about 37% by weight, about 26% to about 36% by weight, about 26% to about 35% by weight, about 26% to about 34% by weight, about 26% to about 33% by weight, about 26% to about 32% by weight, about 26% to about 31% by weight, about 26% to about 30% by weight, about 26% to about 29% by weight, about 26% to about 28% by weight, about 26% to about 27% by weight, about 27% to about 50% by weight, about 27% to about 49% by weight, about 27% to about 48% by weight, about 27% to about 47% by weight, about 27% to about 46% by weight, about 27% to about 45% by weight, about 27% to about 44% by weight, about 27% to about 43% by weight, about 27% to about 42% by weight, about 27% to about 41% by weight, about 27% to about 40% by weight, about 27% to about 39% by weight, about 27% to about 38% by weight, about 27% to about 37% by weight, about 27% to about 36% by weight, about 27% to about 35% by weight, about 27% to about 34% by weight, about 27% to about 33% by weight, about 27% to about 32% by weight, about 27% to about 31% by weight, about 27% to about 30% by weight, about 27% to about 29% by weight, about 27% to about 28% by weight, about 28% to about 50% by weight, about 28% to about 49% by weight, about 28% to about 48% by weight, about 28% to about 47% by weight, about 28% to about 46% by weight, about 28% to about 45% by weight, about 28% to about 44% by weight, about 28% to about 43% by weight, about 28% to about 42% by weight, about 28% to about 41% by weight, about 28% to about 40% by weight, about 28% to about 39% by weight, about 28% to about 38% by weight, about 28% to about 37% by weight, about 28% to about 36% by weight, about 28% to about 35% by weight, about 28% to about 34% by weight, about 28% to about 33% by weight, about 28% to about 32% by weight, about 28% to about 31% by weight, about 28% to about 30% by weight, about 28% to about 29% by weight, about 29% to about 50% by weight, about 29% to about 49% by weight, about 29% to about 48% by weight, about 29% to about 47% by weight, about 29% to about 46% by weight, about 29% to about 45% by weight, about 29% to about 44% by weight, about 29% to about 43% by weight, about 29% to about 42% by weight, about 29% to about 41% by weight, about 29% to about 40% by weight, about 29% to about 39% by weight, about 29% to about 38% by weight, about 29% to about 37% by weight, about 29% to about 36% by weight, about 29% to about 35% by weight, about 29% to about 34% by weight, about 29% to about 33% by weight, about 29% to about 32% by weight, about 29% to about 31% by weight, about 29% to about 30% by weight, about 30% to about 50% by weight, about 30% to about 49% by weight, about 30% to about 48% by weight, about 30% to about 47% by weight, about 30% to about 46% by weight, about 30% to about 45% by weight, about 30% to about 44% by weight, about 30% to about 43% by weight, about 30% to about 42% by weight, about 30% to about 41% by weight, about 30% to about 40% by weight, about 30% to about 39% by weight, about 30% to about 38% by weight, about 30% to about 37% by weight, about 30% to about 36% by weight, about 30% to about 35% by weight, about 30% to about 34% by weight, about 30% to about 33% by weight, about 30% to about 32% by weight, about 30% to about 31% by weight, about 31% to about 50% by weight, about 31% to about 49% by weight, about 31% to about 48% by weight, about 31% to about 47% by weight, about 31% to about 46% by weight, about 31% to about 45% by weight, about 31% to about 44% by weight, about 31% to about 43% by weight, about 31% to about 42% by weight, about 31% to about 41% by weight, about 31% to about 40% by weight, about 31% to about 39% by weight, about 31% to about 38% by weight, about 31% to about 37% by weight, about 31% to about 36% by weight, about 31% to about 35% by weight, about 31% to about 34% by weight, about 31% to about 33% by weight, about 31% to about 32% by weight, about 32% to about 50% by weight, about 32% to about 49% by weight, about 32% to about 48% by weight, about 32% to about 47% by weight, about 32% to about 46% by weight, about 32% to about 45% by weight, about 32% to about 44% by weight, about 32% to about 43% by weight, about 32% to about 42% by weight, about 32% to about 41% by weight, about 32% to about 40% by weight, about 32% to about 39% by weight, about 32% to about 38% by weight, about 32% to about 37% by weight, about 32% to about 36% by weight, about 32% to about 35% by weight, about 32% to about 34% by weight, about 32% to about 33% by weight, about 33% to about 50% by weight, about 33% to about 49% by weight, about 33% to about 48% by weight, about 33% to about 47% by weight, about 33% to about 46% by weight, about 33% to about 45% by weight, about 33% to about 44% by weight, about 33% to about 43% by weight, about 33% to about 42% by weight, about 33% to about 41% by weight, about 33% to about 40% by weight, about 33% to about 39% by weight, about 33% to about 38% by weight, about 33% to about 37% by weight, about 33% to about 36% by weight, about 33% to about 35% by weight, about 33% to about 34% by weight, about 34% to about 50% by weight, about 34% to about 49% by weight, about 34% to about 48% by weight, about 34% to about 47% by weight, about 34% to about 46% by weight, about 34% to about 45% by weight, about 34% to about 44% by weight, about 34% to about 43% by weight, about 34% to about 42% by weight, about 34% to about 41% by weight, about 34% to about 40% by weight, about 34% to about 39% by weight, about 34% to about 38% by weight, about 34% to about 37% by weight, about 34% to about 36% by weight, about 34% to about 35% by weight, about 35% to about 50% by weight, about 35% to about 49% by weight, about 35% to about 48% by weight, about 35% to about 47% by weight, about 35% to about 46% by weight, about 35% to about 45% by weight, about 35% to about 44% by weight, about 35% to about 43% by weight, about 35% to about 42% by weight, about 35% to about 41% by weight, about 35% to about 40% by weight, about 35% to about 39% by weight, about 35% to about 38% by weight, about 35% to about 37% by weight, about 35% to about 36% by weight, about 36% to about 50% by weight, about 36% to about 49% by weight, about 36% to about 48% by weight, about 36% to about 47% by weight, about 36% to about 46% by weight, about 36% to about 45% by weight, about 36% to about 44% by weight, about 36% to about 43% by weight, about 36% to about 42% by weight, about 36% to about 41% by weight, about 36% to about 40% by weight, about 36% to about 39% by weight, about 36% to about 38% by weight, about 36% to about 37% by weight, about 37% to about 50% by weight, about 37% to about 49% by weight, about 37% to about 48% by weight, about 37% to about 47% by weight, about 37% to about 46% by weight, about 37% to about 45% by weight, about 37% to about 44% by weight, about 37% to about 43% by weight, about 37% to about 42% by weight, about 37% to about 41% by weight, about 37% to about 40% by weight, about 37% to about 39% by weight, about 37% to about 38% by weight, about 38% to about 50% by weight, about 38% to about 49% by weight, about 38% to about 48% by weight, about 38% to about 47% by weight, about 38% to about 46% by weight, about 38% to about 45% by weight, about 38% to about 44% by weight, about 38% to about 43% by weight, about 38% to about 42% by weight, about 38% to about 41% by weight, about 38% to about 40% by weight, about 38% to about 39% by weight, about 39% to about 50% by weight, about 39% to about 49% by weight, about 39% to about 48% by weight, about 39% to about 47% by weight, about 39% to about 46% by weight, about 39% to about 45% by weight, about 39% to about 44% by weight, about 39% to about 43% by weight, about 39% to about 42% by weight, about 39% to about 41% by weight, about 39% to about 40% by weight, about 40% to about 50% by weight, about 40% to about 49% by weight, about 40% to about 48% by weight, about 40% to about 47% by weight, about 40% to about 46% by weight, about 40% to about 45% by weight, about 40% to about 44% by weight, about 40% to about 43% by weight, about 40% to about 42% by weight, about 40% to about 41% by weight, about 41% to about 50% by weight, about 41% to about 49% by weight, about 41% to about 48% by weight, about 41% to about 47% by weight, about 41% to about 46% by weight, about 41% to about 45% by weight, about 41% to about 44% by weight, about 41% to about 43% by weight, about 41% to about 42% by weight, about 42% to about 50% by weight, about 42% to about 49% by weight, about 42% to about 48% by weight, about 42% to about 47% by weight, about 42% to about 46% by weight, about 42% to about 45% by weight, about 42% to about 44% by weight, about 42% to about 43% by weight, about 43% to about 50% by weight, about 43% to about 49% by weight, about 43% to about 48% by weight, about 43% to about 47% by weight, about 43% to about 46% by weight, about 43% to about 45% by weight, about 43% to about 44% by weight, about 44% to about 50% by weight, about 44% to about 49% by weight, about 44% to about 48% by weight, about 44% to about 47% by weight, about 44% to about 46% by weight, about 44% to about 45% by weight, about 45% to about 50% by weight, about 45% to about 49% by weight, about 45% to about 48% by weight, about 45% to about 47% by weight, about 45% to about 46% by weight, about 46% to about 50% by weight, about 46% to about 49% by weight, about 46% to about 48% by weight, about 46% to about 47% by weight, about 47% to about 50% by weight, about 47% to about 49% by weight, about 47% to about 48% by weight, about 48% to about 50% by weight, about 48% to about 49% by weight, or about 49% to about 50% by weight. In certain embodiments, the oil is present in about 5% by weight, about 5.5% by weight, about 6% by weight, about 6.5% by weight, about 7% by weight, about 7.5% by weight, about 8% by weight, about 8.5% by weight, about 9% by weight, about 9.5% by weight, about 10% by weight, about 10.5% by weight, about 11% by weight, about 11.5% by weight, about 12% by weight, about 12.5% by weight, about 13% by weight, about 13.5% by weight, about 14% by weight, about 14.5% by weight, about 15% by weight, about 15.5% by weight, about 16% by weight, about 16.5% by weight, about 17% by weight, about 17.5% by weight, about 18% by weight, about 18.5% by weight, about 19% by weight, about 19.5% by weight, about 20% by weight, about 20.5% by weight, about 21% by weight, about 21.5% by weight, about 22% by weight, about 22.5% by weight, about 23% by weight, about 23.5% by weight, about 24% by weight, about 24.5% by weight, about 25% by weight, about 25.5% by weight, about 26% by weight, about 26.5% by weight, about 27% by weight, about 27.5% by weight, about 28% by weight, about 28.5% by weight, about 29% by weight, about 29.5% by weight, about 30% by weight, about 30.5% by weight, about 31% by weight, about 31.5% by weight, about 32% by weight, about 32.5% by weight, about 33% by weight, about 33.5% by weight, about 34% by weight, about 34.5% by weight, about 35% by weight, about 35.5% by weight, about 36% by weight, about 36.5% by weight, about 37% by weight, about 37.5% by weight, about 38% by weight, about 38.5% by weight, about 39% by weight, about 39.5% by weight, about 40% by weight, about 40.5% by weight, about 41% by weight, about 41.5% by weight, about 42% by weight, about 42.5% by weight, about 43% by weight, about 43.5% by weight, about 44% by weight, about 44.5% by weight, about 45% by weight, about 45.5% by weight, about 46% by weight, about 46.5% by weight, about 47% by weight, about 47.5% by weight, about 48% by weight, about 48.5% by weight, about 49% by weight, about 49.5% by weight, or about 50% by weight.

In certain embodiments, the coupling solvent is present in a range of about 0.1% to about 10% by weight, about 0.1% to about 9.5% by weight, about 0.1% to about 9% by weight, about 0.1% to about 8.5% by weight, about 0.1% to about 8% by weight, about 0.1% to about 7.5% by weight, about 0.1% to about 7% by weight, about 0.1% to about 6.5% by weight, about 0.1% to about 6% by weight, about 0.1% to about 5.5% by weight, about 0.1% to about 5% by weight, about 0.1% to about 4.5% by weight, about 0.1% to about 4% by weight, about 0.1% to about 3.5% by weight, about 0.1% to about 3% by weight, about 0.1% to about 2.5% by weight, about 0.1% to about 2% by weight, about 0.1% to about 1.5% by weight, about 0.1% to about 1% by weight, about 0.1% to about 0.75% by weight, about 0.1% to about 0.5% by weight, about 0.1% to about 0.25% by weight, about 0.25% to about 10% by weight, about 0.25% to about 9.5% by weight, about 0.25% to about 9% by weight, about 0.25% to about 8.5% by weight, about 0.25% to about 8% by weight, about 0.25% to about 7.5% by weight, about 0.25% to about 7% by weight, about 0.25% to about 6.5% by weight, about 0.25% to about 6% by weight, about 0.25% to about 5.5% by weight, about 0.25% to about 5% by weight, about 0.25% to about 4.5% by weight, about 0.25% to about 4% by weight, about 0.25% to about 3.5% by weight, about 0.25% to about 3% by weight, about 0.25% to about 2.5% by weight, about 0.25% to about 2% by weight, about 0.25% to about 1.5% by weight, about 0.25% to about 1% by weight, about 0.25% to about 0.75% by weight, about 0.25% to about 0.5% by weight, about 0.5% to about 10% by weight, about 0.5% to about 9.5% by weight, about 0.5% to about 9% by weight, about 0.5% to about 8.5% by weight, about 0.5% to about 8% by weight, about 0.5 to about 7.5% by weight, about 0.5% to about 7% by weight, about 0.5% to about 6.5% by weight, about 0.5% to about 6% by weight, about 0.5% to about 5.5% by weight, about 0.5% to about 5% by weight, about 0.5% to about 4.5% by weight, about 0.5% to about 4% by weight, about 0.5% to about 3.5% by weight, about 0.5% to about 3% by weight, about 0.5% to about 2.5% by weight, about 0.5% to about 2% by weight, about 0.5% to about 1.5% by weight, about 0.5% to about 1% by weight, about 0.75% to about 10% by weight, about 0.75% to about 9.5% by weight, about 0.75% to about 9% by weight, about 0.75% to about 8.5% by weight, about 0.75% to about 8% by weight, about 0.75 to about 7.5% by weight, about 0.75% to about 7% by weight, about 0.75% to about 6.5% by weight, about 0.75% to about 6% by weight, about 0.75% to about 5.5% by weight, about 0.75% to about 5% by weight, about 0.75% to about 4.5% by weight, about 0.75% to about 4% by weight, about 0.75% to about 3.75% by weight, about 0.75% to about 3% by weight, about 0.75% to about 2.5% by weight, about 0.75% to about 2% by weight, about 0.75% to about 1.5% by weight, about 0.75% to about 1% by weight, about 1% to about 10% by weight, about 1% to about 9.5% by weight, about 1% to about 9% by weight, about 1% to about 8.5% by weight, about 1% to about 8% by weight, about 1% to about 7.5% by weight, about 1% to about 7% by weight, about 1% to about 6.5% by weight, about 1% to about 6% by weight, about 1% to about 5.5% by weight, about 1% to about 5% by weight, about 1% to about 4.5% by weight, about 1% to about 4% by weight, about 1% to about 3.5% by weight, about 1% to about 3% by weight, about 1% to about 2.5% by weight, about 1% to about 2% by weight, about 1% to about 1.5% by weight, about 1.5% to about 10% by weight, about 1.5% to about 9.5% by weight, about 1.5% to about 9% by weight, about 1.5% to about 8.5% by weight, about 1.5% to about 8% by weight, about 1.5 to about 7.5% by weight, about 1.5% to about 7% by weight, about 1.5% to about 6.5% by weight, about 1.5% to about 6% by weight, about 1.5% to about 5.5% by weight, about 1.5% to about 5% by weight, about 1.5% to about 4.5% by weight, about 1.5% to about 4% by weight, about 1.5% to about 3.5% by weight, about 1.5% to about 3% by weight, about 1.5% to about 2.5% by weight, about 1.5% to about 2% by weight, about 2% to about 10% by weight, about 2% to about 9.5% by weight, about 2% to about 9% by weight, about 2% to about 8.5% by weight, about 2% to about 8% by weight, about 2% to about 7.5% by weight, about 2% to about 7% by weight, about 2% to about 6.5% by weight, about 2% to about 6% by weight, about 2% to about 5.5% by weight, about 2% to about 5% by weight, about 2% to about 4.5% by weight, about 2% to about 4% by weight, about 2% to about 3.5% by weight, about 2% to about 3% by weight, about 2% to about 2.5% by weight, about 2.5% to about 10% by weight, about 2.5% to about 9.5% by weight, about 2.5% to about 9% by weight, about 2.5% to about 8.5% by weight, about 2.5% to about 8% by weight, about 2.5 to about 7.5% by weight, about 2.5% to about 7% by weight, about 2.5% to about 6.5% by weight, about 2.5% to about 6% by weight, about 2.5% to about 5.5% by weight, about 2.5% to about 5% by weight, about 2.5% to about 4.5% by weight, about 2.5% to about 4% by weight, about 2.5% to about 3.5% by weight, about 2.5% to about 3% by weight, about 3% to about 10% by weight, about 3% to about 9.5% by weight, about 3% to about 9% by weight, about 3% to about 8.5% by weight, about 3% to about 8% by weight, about 3% to about 7.5% by weight, about 3% to about 8% by weight, about 3% to about 7% by weight, about 3% to about 6.5% by weight, about 3% to about 6% by weight, about 3% to about 5.5% by weight, about 3% to about 5% by weight, about 3% to about 4.5% by weight, about 3% to about 4% by weight, about 3% to about 3.5% by weight, about 3.5% to about 10% by weight, about 3.5% to about 9.5% by weight, about 3.5% to about 9% by weight, about 3.5% to about 8.5% by weight, about 3.5% to about 8% by weight, about 3.5% to about 7.5% by weight, about 3.5% to about 7% by weight, about 3.5% to about 6.5% by weight, about 3.5% to about 6% by weight, about 3.5% to about 5.5% by weight, about 3.5% to about 5% by weight, about 3.5% to about 4.5% by weight, about 3.5% to about 4% by weight, about 4% to about 10% by weight, about 4% to about 9.5% by weight, about 4% to about 9% by weight, about 4% to about 8.5% by weight, about 4% to about 8% by weight, about 4% to about 7.5% by weight, about 4% to about 7% by weight, about 4% to about 6.5% by weight, about 4% to about 6% by weight, about 4% to about 5.5% by weight, about 4% to about 5% by weight, about 4% to about 4.5% by weight, about 4.5% to about 10% by weight, about 4.5% to about 9.5% by weight, about 4.5% to about 9% by weight, about 4.5% to about 8.5% by weight, about 4.5% to about 8% by weight, about 4.5% to about 7.5% by weight, about 4.5% to about 7% by weight, about 4.5% to about 6.5% by weight, about 4.5% to about 6% by weight, about 4.5% to about 5.5% by weight, about 4.5% to about 5% by weight, about 5% to about 10% by weight, about 5% to about 9.5% by weight, about 5% to about 9% by weight, about 5% to about 8.5% by weight, about 5% to about 8% by weight, about 5% to about 7.5% by weight, about 5% to about 7% by weight, about 5% to about 6.5% by weight, about 5% to about 6% by weight, about 5% to about 5.5% by weight, about 5.5% to about 10% by weight, about 5.5% to about 9.5% by weight, about 5.5% to about 9% by weight, about 5.5% to about 8.5% by weight, about 5.5% to about 8% by weight, about 5.5% to about 7.5% by weight, about 5.5% to about 7% by weight, about 5.5% to about 6.5% by weight, about 5.5% to about 6% by weight, about 6% to about 10% by weight, about 6% to about 9.5% by weight, about 6% to about 9% by weight, about 6% to about 8.5% by weight, about 6% to about 8% by weight, about 6% to about 7.5% by weight, about 6% to about 7% by weight, about 6% to about 6.5% by weight, about 6.5% to about 10% by weight, about 6.5% to about 9.5% by weight, about 6.5% to about 9% by weight, about 6.5% to about 8.5% by weight, about 6.5% to about 8% by weight, about 6.5% to about 7.5% by weight, about 6.5% to about 7% by weight, about 7% to about 10% by weight, about 7% to about 9.5% by weight, about 7% to about 9% by weight, about 7% to about 8.5% by weight, about 7% to about 8% by weight, about 7% to about 7.5% by weight, about 7.5% to about 10% by weight, about 7.5% to about 9.5% by weight, about 7.5% to about 9% by weight, about 7.5% to about 8.5% by weight, about 7.5% to about 8% by weight, about 8% to about 10% by weight, about 8% to about 9.5% by weight, about 8% to about 9% by weight, about 8% to about 8.5% by weight, about 8.5% to about 10% by weight, about 8.5% to about 9.5% by weight, about 8.5% to about 9% by weight, about 9% to about 10% by weight, about 9% to about 9.5% by weight, or about 9.5% to about 10% by weight. In certain embodiments, the coupling solvent is present in about 0.1% by weight, about 0.25% by weight, about 0.5% by weight, about 0.75% by weight, about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 7% by weight, about 7.5% by weight, about 8% by weight, about 8.5% by weight, about 9% by weight, about 9.5% by weight, or about 10% by weight.

In certain embodiments, a second emulsifier is present in a range of about 1% to about 10% by weight, about 1% to about 9.5% by weight, about 1% to about 9% by weight, about 1% to about 8.5% by weight, about 1% to about 8% by weight, about 1% to about 7.5% by weight, about 1% to about 7% by weight, about 1% to about 6.5% by weight, about 1% to about 6% by weight, about 1% to about 5.5% by weight, about 1% to about 5% by weight, about 1% to about 4.5% by weight, about 1% to about 4% by weight, about 1% to about 3.5% by weight, about 1% to about 3% by weight, about 1% to about 2.5% by weight, about 1% to about 2% by weight, about 1% to about 1.5% by weight, about 1.5% to about 10% by weight, about 1.5% to about 9.5% by weight, about 1.5% to about 9% by weight, about 1.5% to about 8.5% by weight, about 1.5% to about 8% by weight, about 1.5 to about 7.5% by weight, about 1.5% to about 7% by weight, about 1.5% to about 6.5% by weight, about 1.5% to about 6% by weight, about 1.5% to about 5.5% by weight, about 1.5% to about 5% by weight, about 1.5% to about 4.5% by weight, about 1.5% to about 4% by weight, about 1.5% to about 3.5% by weight, about 1.5% to about 3% by weight, about 1.5% to about 2.5% by weight, about 1.5% to about 2% by weight, about 2% to about 10% by weight, about 2% to about 9.5% by weight, about 2% to about 9% by weight, about 2% to about 8.5% by weight, about 2% to about 8% by weight, about 2% to about 7.5% by weight, about 2% to about 7% by weight, about 2% to about 6.5% by weight, about 2% to about 6% by weight, about 2% to about 5.5% by weight, about 2% to about 5% by weight, about 2% to about 4.5% by weight, about 2% to about 4% by weight, about 2% to about 3.5% by weight, about 2% to about 3% by weight, about 2% to about 2.5% by weight, about 2.5% to about 10% by weight, about 2.5% to about 9.5% by weight, about 2.5% to about 9% by weight, about 2.5% to about 8.5% by weight, about 2.5% to about 8% by weight, about 2.5 to about 7.5% by weight, about 2.5% to about 7% by weight, about 2.5% to about 6.5% by weight, about 2.5% to about 6% by weight, about 2.5% to about 5.5% by weight, about 2.5% to about 5% by weight, about 2.5% to about 4.5% by weight, about 2.5% to about 4% by weight, about 2.5% to about 3.5% by weight, about 2.5% to about 3% by weight, about 3% to about 10% by weight, about 3% to about 9.5% by weight, about 3% to about 9% by weight, about 3% to about 8.5% by weight, about 3% to about 8% by weight, about 3% to about 7.5% by weight, about 3% to about 8% by weight, about 3% to about 7% by weight, about 3% to about 6.5% by weight, about 3% to about 6% by weight, about 3% to about 5.5% by weight, about 3% to about 5% by weight, about 3% to about 4.5% by weight, about 3% to about 4% by weight, about 3% to about 3.5% by weight, about 3.5% to about 10% by weight, about 3.5% to about 9.5% by weight, about 3.5% to about 9% by weight, about 3.5% to about 8.5% by weight, about 3.5% to about 8% by weight, about 3.5% to about 7.5% by weight, about 3.5% to about 7% by weight, about 3.5% to about 6.5% by weight, about 3.5% to about 6% by weight, about 3.5% to about 5.5% by weight, about 3.5% to about 5% by weight, about 3.5% to about 4.5% by weight, about 3.5% to about 4% by weight, about 4% to about 10% by weight, about 4% to about 9.5% by weight, about 4% to about 9% by weight, about 4% to about 8.5% by weight, about 4% to about 8% by weight, about 4% to about 7.5% by weight, about 4% to about 7% by weight, about 4% to about 6.5% by weight, about 4% to about 6% by weight, about 4% to about 5.5% by weight, about 4% to about 5% by weight, about 4% to about 4.5% by weight, about 4.5% to about 10% by weight, about 4.5% to about 9.5% by weight, about 4.5% to about 9% by weight, about 4.5% to about 8.5% by weight, about 4.5% to about 8% by weight, about 4.5% to about 7.5% by weight, about 4.5% to about 7% by weight, about 4.5% to about 6.5% by weight, about 4.5% to about 6% by weight, about 4.5% to about 5.5% by weight, about 4.5% to about 5% by weight, about 5% to about 10% by weight, about 5% to about 9.5% by weight, about 5% to about 9% by weight, about 5% to about 8.5% by weight, about 5% to about 8% by weight, about 5% to about 7.5% by weight, about 5% to about 7% by weight, about 5% to about 6.5% by weight, about 5% to about 6% by weight, about 5% to about 5.5% by weight, about 5.5% to about 10% by weight, about 5.5% to about 9.5% by weight, about 5.5% to about 9% by weight, about 5.5% to about 8.5% by weight, about 5.5% to about 8% by weight, about 5.5% to about 7.5% by weight, about 5.5% to about 7% by weight, about 5.5% to about 6.5% by weight, about 5.5% to about 6% by weight, about 6% to about 10% by weight, about 6% to about 9.5% by weight, about 6% to about 9% by weight, about 6% to about 8.5% by weight, about 6% to about 8% by weight, about 6% to about 7.5% by weight, about 6% to about 7% by weight, about 6% to about 6.5% by weight, about 6.5% to about 10% by weight, about 6.5% to about 9.5% by weight, about 6.5% to about 9% by weight, about 6.5% to about 8.5% by weight, about 6.5% to about 8% by weight, about 6.5% to about 7.5% by weight, about 6.5% to about 7% by weight, about 7% to about 10% by weight, about 7% to about 9.5% by weight, about 7% to about 9% by weight, about 7% to about 8.5% by weight, about 7% to about 8% by weight, about 7% to about 7.5% by weight, about 7.5% to about 10% by weight, about 7.5% to about 9.5% by weight, about 7.5% to about 9% by weight, about 7.5% to about 8.5% by weight, about 7.5% to about 8% by weight, about 8% to about 10% by weight, about 8% to about 9.5% by weight, about 8% to about 9% by weight, about 8% to about 8.5% by weight, about 8.5% to about 10% by weight, about 8.5% to about 9.5% by weight, about 8.5% to about 9% by weight, about 9% to about 10% by weight, about 9% to about 9.5% by weight, or about 9.5% to about 10% by weight. In certain embodiments, the second emulsifier is present in about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 7% by weight, about 7.5% by weight, about 8% by weight, about 8.5% by weight, about 9% by weight, about 9.5% by weight, or about 10% by weight.

In certain embodiments, the biocide is present in a range of about 0.1% to about 10% by weight, about 0.1% to about 9.5% by weight, about 0.1% to about 9% by weight, about 0.1% to about 8.5% by weight, about 0.1% to about 8% by weight, about 0.1% to about 7.5% by weight, about 0.1% to about 7% by weight, about 0.1% to about 6.5% by weight, about 0.1% to about 6% by weight, about 0.1% to about 5.5% by weight, about 0.1% to about 5% by weight, about 0.1% to about 4.5% by weight, about 0.1% to about 4% by weight, about 0.1% to about 3.5% by weight, about 0.1% to about 3% by weight, about 0.1% to about 2.5% by weight, about 0.1% to about 2% by weight, about 0.1% to about 1.5% by weight, about 0.1% to about 1% by weight, about 0.1% to about 0.75% by weight, about 0.1% to about 0.5% by weight, about 0.1% to about 0.25% by weight, about 0.25% to about 10% by weight, about 0.25% to about 9.5% by weight, about 0.25% to about 9% by weight, about 0.25% to about 8.5% by weight, about 0.25% to about 8% by weight, about 0.25% to about 7.5% by weight, about 0.25% to about 7% by weight, about 0.25% to about 6.5% by weight, about 0.25% to about 6% by weight, about 0.25% to about 5.5% by weight, about 0.25% to about 5% by weight, about 0.25% to about 4.5% by weight, about 0.25% to about 4% by weight, about 0.25% to about 3.5% by weight, about 0.25% to about 3% by weight, about 0.25% to about 2.5% by weight, about 0.25% to about 2% by weight, about 0.25% to about 1.5% by weight, about 0.25% to about 1% by weight, about 0.25% to about 0.75% by weight, about 0.25% to about 0.5% by weight, about 0.5% to about 10% by weight, about 0.5% to about 9.5% by weight, about 0.5% to about 9% by weight, about 0.5% to about 8.5% by weight, about 0.5% to about 8% by weight, about 0.5 to about 7.5% by weight, about 0.5% to about 7% by weight, about 0.5% to about 6.5% by weight, about 0.5% to about 6% by weight, about 0.5% to about 5.5% by weight, about 0.5% to about 5% by weight, about 0.5% to about 4.5% by weight, about 0.5% to about 4% by weight, about 0.5% to about 3.5% by weight, about 0.5% to about 3% by weight, about 0.5% to about 2.5% by weight, about 0.5% to about 2% by weight, about 0.5% to about 1.5% by weight, about 0.5% to about 1% by weight, about 0.75% to about 10% by weight, about 0.75% to about 9.5% by weight, about 0.75% to about 9% by weight, about 0.75% to about 8.5% by weight, about 0.75% to about 8% by weight, about 0.75 to about 7.5% by weight, about 0.75% to about 7% by weight, about 0.75% to about 6.5% by weight, about 0.75% to about 6% by weight, about 0.75% to about 5.5% by weight, about 0.75% to about 5% by weight, about 0.75% to about 4.5% by weight, about 0.75% to about 4% by weight, about 0.75% to about 3.75% by weight, about 0.75% to about 3% by weight, about 0.75% to about 2.5% by weight, about 0.75% to about 2% by weight, about 0.75% to about 1.5% by weight, about 0.75% to about 1% by weight, about 1% to about 10% by weight, about 1% to about 9.5% by weight, about 1% to about 9% by weight, about 1% to about 8.5% by weight, about 1% to about 8% by weight, about 1% to about 7.5% by weight, about 1% to about 7% by weight, about 1% to about 6.5% by weight, about 1% to about 6% by weight, about 1% to about 5.5% by weight, about 1% to about 5% by weight, about 1% to about 4.5% by weight, about 1% to about 4% by weight, about 1% to about 3.5% by weight, about 1% to about 3% by weight, about 1% to about 2.5% by weight, about 1% to about 2% by weight, about 1% to about 1.5% by weight, about 1.5% to about 10% by weight, about 1.5% to about 9.5% by weight, about 1.5% to about 9% by weight, about 1.5% to about 8.5% by weight, about 1.5% to about 8% by weight, about 1.5 to about 7.5% by weight, about 1.5% to about 7% by weight, about 1.5% to about 6.5% by weight, about 1.5% to about 6% by weight, about 1.5% to about 5.5% by weight, about 1.5% to about 5% by weight, about 1.5% to about 4.5% by weight, about 1.5% to about 4% by weight, about 1.5% to about 3.5% by weight, about 1.5% to about 3% by weight, about 1.5% to about 2.5% by weight, about 1.5% to about 2% by weight, about 2% to about 10% by weight, about 2% to about 9.5% by weight, about 2% to about 9% by weight, about 2% to about 8.5% by weight, about 2% to about 8% by weight, about 2% to about 7.5% by weight, about 2% to about 7% by weight, about 2% to about 6.5% by weight, about 2% to about 6% by weight, about 2% to about 5.5% by weight, about 2% to about 5% by weight, about 2% to about 4.5% by weight, about 2% to about 4% by weight, about 2% to about 3.5% by weight, about 2% to about 3% by weight, about 2% to about 2.5% by weight, about 2.5% to about 10% by weight, about 2.5% to about 9.5% by weight, about 2.5% to about 9% by weight, about 2.5% to about 8.5% by weight, about 2.5% to about 8% by weight, about 2.5 to about 7.5% by weight, about 2.5% to about 7% by weight, about 2.5% to about 6.5% by weight, about 2.5% to about 6% by weight, about 2.5% to about 5.5% by weight, about 2.5% to about 5% by weight, about 2.5% to about 4.5% by weight, about 2.5% to about 4% by weight, about 2.5% to about 3.5% by weight, about 2.5% to about 3% by weight, about 3% to about 10% by weight, about 3% to about 9.5% by weight, about 3% to about 9% by weight, about 3% to about 8.5% by weight, about 3% to about 8% by weight, about 3% to about 7.5% by weight, about 3% to about 8% by weight, about 3% to about 7% by weight, about 3% to about 6.5% by weight, about 3% to about 6% by weight, about 3% to about 5.5% by weight, about 3% to about 5% by weight, about 3% to about 4.5% by weight, about 3% to about 4% by weight, about 3% to about 3.5% by weight, about 3.5% to about 10% by weight, about 3.5% to about 9.5% by weight, about 3.5% to about 9% by weight, about 3.5% to about 8.5% by weight, about 3.5% to about 8% by weight, about 3.5% to about 7.5% by weight, about 3.5% to about 7% by weight, about 3.5% to about 6.5% by weight, about 3.5% to about 6% by weight, about 3.5% to about 5.5% by weight, about 3.5% to about 5% by weight, about 3.5% to about 4.5% by weight, about 3.5% to about 4% by weight, about 4% to about 10% by weight, about 4% to about 9.5% by weight, about 4% to about 9% by weight, about 4% to about 8.5% by weight, about 4% to about 8% by weight, about 4% to about 7.5% by weight, about 4% to about 7% by weight, about 4% to about 6.5% by weight, about 4% to about 6% by weight, about 4% to about 5.5% by weight, about 4% to about 5% by weight, about 4% to about 4.5% by weight, about 4.5% to about 10% by weight, about 4.5% to about 9.5% by weight, about 4.5% to about 9% by weight, about 4.5% to about 8.5% by weight, about 4.5% to about 8% by weight, about 4.5% to about 7.5% by weight, about 4.5% to about 7% by weight, about 4.5% to about 6.5% by weight, about 4.5% to about 6% by weight, about 4.5% to about 5.5% by weight, about 4.5% to about 5% by weight, about 5% to about 10% by weight, about 5% to about 9.5% by weight, about 5% to about 9% by weight, about 5% to about 8.5% by weight, about 5% to about 8% by weight, about 5% to about 7.5% by weight, about 5% to about 7% by weight, about 5% to about 6.5% by weight, about 5% to about 6% by weight, about 5% to about 5.5% by weight, about 5.5% to about 10% by weight, about 5.5% to about 9.5% by weight, about 5.5% to about 9% by weight, about 5.5% to about 8.5% by weight, about 5.5% to about 8% by weight, about 5.5% to about 7.5% by weight, about 5.5% to about 7% by weight, about 5.5% to about 6.5% by weight, about 5.5% to about 6% by weight, about 6% to about 10% by weight, about 6% to about 9.5% by weight, about 6% to about 9% by weight, about 6% to about 8.5% by weight, about 6% to about 8% by weight, about 6% to about 7.5% by weight, about 6% to about 7% by weight, about 6% to about 6.5% by weight, about 6.5% to about 10% by weight, about 6.5% to about 9.5% by weight, about 6.5% to about 9% by weight, about 6.5% to about 8.5% by weight, about 6.5% to about 8% by weight, about 6.5% to about 7.5% by weight, about 6.5% to about 7% by weight, about 7% to about 10% by weight, about 7% to about 9.5% by weight, about 7% to about 9% by weight, about 7% to about 8.5% by weight, about 7% to about 8% by weight, about 7% to about 7.5% by weight, about 7.5% to about 10% by weight, about 7.5% to about 9.5% by weight, about 7.5% to about 9% by weight, about 7.5% to about 8.5% by weight, about 7.5% to about 8% by weight, about 8% to about 10% by weight, about 8% to about 9.5% by weight, about 8% to about 9% by weight, about 8% to about 8.5% by weight, about 8.5% to about 10% by weight, about 8.5% to about 9.5% by weight, about 8.5% to about 9% by weight, about 9% to about 10% by weight, about 9% to about 9.5% by weight, or about 9.5% to about 10% by weight. In certain embodiments, the biocide is present in about 0.1% by weight, about 0.25% by weight, about 0.5% by weight, about 0.75% by weight, about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 7% by weight, about 7.5% by weight, about 8% by weight, about 8.5% by weight, about 9% by weight, about 9.5% by weight, or about 10% by weight.

In certain embodiments, the fungicide is present in a range of about 0.1% to about 10% by weight, about 0.1% to about 9.5% by weight, about 0.1% to about 9% by weight, about 0.1% to about 8.5% by weight, about 0.1% to about 8% by weight, about 0.1% to about 7.5% by weight, about 0.1% to about 7% by weight, about 0.1% to about 6.5% by weight, about 0.1% to about 6% by weight, about 0.1% to about 5.5% by weight, about 0.1% to about 5% by weight, about 0.1% to about 4.5% by weight, about 0.1% to about 4% by weight, about 0.1% to about 3.5% by weight, about 0.1% to about 3% by weight, about 0.1% to about 2.5% by weight, about 0.1% to about 2% by weight, about 0.1% to about 1.5% by weight, about 0.1% to about 1% by weight, about 0.1% to about 0.75% by weight, about 0.1% to about 0.5% by weight, about 0.1% to about 0.25% by weight, about 0.25% to about 10% by weight, about 0.25% to about 9.5% by weight, about 0.25% to about 9% by weight, about 0.25% to about 8.5% by weight, about 0.25% to about 8% by weight, about 0.25% to about 7.5% by weight, about 0.25% to about 7% by weight, about 0.25% to about 6.5% by weight, about 0.25% to about 6% by weight, about 0.25% to about 5.5% by weight, about 0.25% to about 5% by weight, about 0.25% to about 4.5% by weight, about 0.25% to about 4% by weight, about 0.25% to about 3.5% by weight, about 0.25% to about 3% by weight, about 0.25% to about 2.5% by weight, about 0.25% to about 2% by weight, about 0.25% to about 1.5% by weight, about 0.25% to about 1% by weight, about 0.25% to about 0.75% by weight, about 0.25% to about 0.5% by weight, about 0.5% to about 10% by weight, about 0.5% to about 9.5% by weight, about 0.5% to about 9% by weight, about 0.5% to about 8.5% by weight, about 0.5% to about 8% by weight, about 0.5 to about 7.5% by weight, about 0.5% to about 7% by weight, about 0.5% to about 6.5% by weight, about 0.5% to about 6% by weight, about 0.5% to about 5.5% by weight, about 0.5% to about 5% by weight, about 0.5% to about 4.5% by weight, about 0.5% to about 4% by weight, about 0.5% to about 3.5% by weight, about 0.5% to about 3% by weight, about 0.5% to about 2.5% by weight, about 0.5% to about 2% by weight, about 0.5% to about 1.5% by weight, about 0.5% to about 1% by weight, about 0.75% to about 10% by weight, about 0.75% to about 9.5% by weight, about 0.75% to about 9% by weight, about 0.75% to about 8.5% by weight, about 0.75% to about 8% by weight, about 0.75 to about 7.5% by weight, about 0.75% to about 7% by weight, about 0.75% to about 6.5% by weight, about 0.75% to about 6% by weight, about 0.75% to about 5.5% by weight, about 0.75% to about 5% by weight, about 0.75% to about 4.5% by weight, about 0.75% to about 4% by weight, about 0.75% to about 3.75% by weight, about 0.75% to about 3% by weight, about 0.75% to about 2.5% by weight, about 0.75% to about 2% by weight, about 0.75% to about 1.5% by weight, about 0.75% to about 1% by weight, about 1% to about 10% by weight, about 1% to about 9.5% by weight, about 1% to about 9% by weight, about 1% to about 8.5% by weight, about 1% to about 8% by weight, about 1% to about 7.5% by weight, about 1% to about 7% by weight, about 1% to about 6.5% by weight, about 1% to about 6% by weight, about 1% to about 5.5% by weight, about 1% to about 5% by weight, about 1% to about 4.5% by weight, about 1% to about 4% by weight, about 1% to about 3.5% by weight, about 1% to about 3% by weight, about 1% to about 2.5% by weight, about 1% to about 2% by weight, about 1% to about 1.5% by weight, about 1.5% to about 10% by weight, about 1.5% to about 9.5% by weight, about 1.5% to about 9% by weight, about 1.5% to about 8.5% by weight, about 1.5% to about 8% by weight, about 1.5 to about 7.5% by weight, about 1.5% to about 7% by weight, about 1.5% to about 6.5% by weight, about 1.5% to about 6% by weight, about 1.5% to about 5.5% by weight, about 1.5% to about 5% by weight, about 1.5% to about 4.5% by weight, about 1.5% to about 4% by weight, about 1.5% to about 3.5% by weight, about 1.5% to about 3% by weight, about 1.5% to about 2.5% by weight, about 1.5% to about 2% by weight, about 2% to about 10% by weight, about 2% to about 9.5% by weight, about 2% to about 9% by weight, about 2% to about 8.5% by weight, about 2% to about 8% by weight, about 2% to about 7.5% by weight, about 2% to about 7% by weight, about 2% to about 6.5% by weight, about 2% to about 6% by weight, about 2% to about 5.5% by weight, about 2% to about 5% by weight, about 2% to about 4.5% by weight, about 2% to about 4% by weight, about 2% to about 3.5% by weight, about 2% to about 3% by weight, about 2% to about 2.5% by weight, about 2.5% to about 10% by weight, about 2.5% to about 9.5% by weight, about 2.5% to about 9% by weight, about 2.5% to about 8.5% by weight, about 2.5% to about 8% by weight, about 2.5 to about 7.5% by weight, about 2.5% to about 7% by weight, about 2.5% to about 6.5% by weight, about 2.5% to about 6% by weight, about 2.5% to about 5.5% by weight, about 2.5% to about 5% by weight, about 2.5% to about 4.5% by weight, about 2.5% to about 4% by weight, about 2.5% to about 3.5% by weight, about 2.5% to about 3% by weight, about 3% to about 10% by weight, about 3% to about 9.5% by weight, about 3% to about 9% by weight, about 3% to about 8.5% by weight, about 3% to about 8% by weight, about 3% to about 7.5% by weight, about 3% to about 8% by weight, about 3% to about 7% by weight, about 3% to about 6.5% by weight, about 3% to about 6% by weight, about 3% to about 5.5% by weight, about 3% to about 5% by weight, about 3% to about 4.5% by weight, about 3% to about 4% by weight, about 3% to about 3.5% by weight, about 3.5% to about 10% by weight, about 3.5% to about 9.5% by weight, about 3.5% to about 9% by weight, about 3.5% to about 8.5% by weight, about 3.5% to about 8% by weight, about 3.5% to about 7.5% by weight, about 3.5% to about 7% by weight, about 3.5% to about 6.5% by weight, about 3.5% to about 6% by weight, about 3.5% to about 5.5% by weight, about 3.5% to about 5% by weight, about 3.5% to about 4.5% by weight, about 3.5% to about 4% by weight, about 4% to about 10% by weight, about 4% to about 9.5% by weight, about 4% to about 9% by weight, about 4% to about 8.5% by weight, about 4% to about 8% by weight, about 4% to about 7.5% by weight, about 4% to about 7% by weight, about 4% to about 6.5% by weight, about 4% to about 6% by weight, about 4% to about 5.5% by weight, about 4% to about 5% by weight, about 4% to about 4.5% by weight, about 4.5% to about 10% by weight, about 4.5% to about 9.5% by weight, about 4.5% to about 9% by weight, about 4.5% to about 8.5% by weight, about 4.5% to about 8% by weight, about 4.5% to about 7.5% by weight, about 4.5% to about 7% by weight, about 4.5% to about 6.5% by weight, about 4.5% to about 6% by weight, about 4.5% to about 5.5% by weight, about 4.5% to about 5% by weight, about 5% to about 10% by weight, about 5% to about 9.5% by weight, about 5% to about 9% by weight, about 5% to about 8.5% by weight, about 5% to about 8% by weight, about 5% to about 7.5% by weight, about 5% to about 7% by weight, about 5% to about 6.5% by weight, about 5% to about 6% by weight, about 5% to about 5.5% by weight, about 5.5% to about 10% by weight, about 5.5% to about 9.5% by weight, about 5.5% to about 9% by weight, about 5.5% to about 8.5% by weight, about 5.5% to about 8% by weight, about 5.5% to about 7.5% by weight, about 5.5% to about 7% by weight, about 5.5% to about 6.5% by weight, about 5.5% to about 6% by weight, about 6% to about 10% by weight, about 6% to about 9.5% by weight, about 6% to about 9% by weight, about 6% to about 8.5% by weight, about 6% to about 8% by weight, about 6% to about 7.5% by weight, about 6% to about 7% by weight, about 6% to about 6.5% by weight, about 6.5% to about 10% by weight, about 6.5% to about 9.5% by weight, about 6.5% to about 9% by weight, about 6.5% to about 8.5% by weight, about 6.5% to about 8% by weight, about 6.5% to about 7.5% by weight, about 6.5% to about 7% by weight, about 7% to about 10% by weight, about 7% to about 9.5% by weight, about 7% to about 9% by weight, about 7% to about 8.5% by weight, about 7% to about 8% by weight, about 7% to about 7.5% by weight, about 7.5% to about 10% by weight, about 7.5% to about 9.5% by weight, about 7.5% to about 9% by weight, about 7.5% to about 8.5% by weight, about 7.5% to about 8% by weight, about 8% to about 10% by weight, about 8% to about 9.5% by weight, about 8% to about 9% by weight, about 8% to about 8.5% by weight, about 8.5% to about 10% by weight, about 8.5% to about 9.5% by weight, about 8.5% to about 9% by weight, about 9% to about 10% by weight, about 9% to about 9.5% by weight, or about 9.5% to about 10% by weight. In certain embodiments, the fungicide is present in about 0.1% by weight, about 0.25% by weight, about 0.5% by weight, about 0.75% by weight, about 1% by weight, about 1.5% by weight, about 2% by weight, about 2.5% by weight, about 3% by weight, about 3.5% by weight, about 4% by weight, about 4.5% by weight, about 5% by weight, about 5.5% by weight, about 6% by weight, about 7% by weight, about 7.5% by weight, about 8% by weight, about 8.5% by weight, about 9% by weight, about 9.5% by weight, or about 10% by weight.

Additional objects and advantages of the present invention will be appreciated by one of ordinary skill in the art in light of the current description and examples of the preferred embodiments, and are expressly included within the scope of the present invention.

Examples

Examining Partial Esters of DIACID 1550 with 2-Ethylhexanol or Dodecanol as Lubricating Corrosion Inhibitors.

Evaluations were conducted for surface rust prevention, lubricity, hard water tolerance, and foaming properties for partial esters of DIACID 1550 neutralized with either TEA or potassium hydroxide. The following observations were made: (1) potassium and TEA salts of the partial esters are significantly more stable in hard water than the corresponding DIACID 1550 salts; (2) potassium and TEA salts of the partial esters have notably reduced foaming compared to the corresponding DIACID 1550 salts; (3) potassium salts of both the partial esters are better corrosion inhibitors than the potassium salt of DIACID 1550 and the DIACID M-T67; (4) potassium salts of both the partial esters are equivalent boundary lubricants to DIACID M-T67; and (5) TEA salts of the two partial esters are better boundary lubricants than DIACID M-T67.

Partial esters of DIACID 1550, DIACID 1525, and DIACID 1550 XLM with 2-ethylhexanol or dodecanol were synthesized with hypophosphorous acid as a catalyst. Aliquots of the partial esters were neutralized with (1:1) potassium hydroxide as the 41% active aqueous solution or neat (1:1) with TEA 99. The neat TEA salts were clear and flowable. The aqueous 41% active potassium solution of the 2-ethylhexanol partial ester of DIACID 1550 was clear, but the other partial esters were opaque and unstable.

The DIACID 1550 partial ester potassium and TEA salts were diluted to various levels between 0.5% to 10% with 300 ppm hard water. The hard water solutions were examined for short and long term stability; 1% solutions were examined using the Falex Pin and V-Block Lubricity Testing Apparatus (ASTM D2670), 1-5% solutions were examined by the Cast Iron Chip Corrosion Test (ASTM D4627-86), and 0.5%, 2%, and 5% solutions were examined for hard water tolerance, relative foaming tendencies, and clarity. The data is shown in Table 1 and Table 2.

TABLE 1

|  | DIACID 1525 ½ Ester 2-Ethylhexyl | DIACID 1550 ½ Ester 2-Ethylhexyl | DIACID 1550 ½ Ester Dodecyl | DIACID 1550 XLM ½ Ester 2-Ethylhexyl | DIACID 1550 $K^+$ Salt | DIACID M-T67 |
|---|---|---|---|---|---|---|
| TEA Salt (neat) | 1, W | 1, W | 1, W | 1, W | 1, W | 1, W |
| $K^+$ Salt (41%/$H_2O$) | 2, Z | 1, W | 2, Z | 2, Z | 1, W | 1, W |
| TEA Salt |  |  |  |  |  |  |
| 0.5% (300 ppm HW) |  | 1, Y | 1, Y, VLS |  |  | 2, Z, LS |
| 1% (300 ppm HW) |  | 1, Y | 1, Y |  |  |  |
| 2% (300 ppm HW) |  | 1, X | 1, Y |  |  |  |
| 5% (300 ppm HW) |  | 1, X | 1, Y |  |  |  |
| 10% (300 ppm HW) |  | 1, X | 1, Y |  |  | 1, W |
| $K^+$ Salt |  |  |  |  |  |  |
| 0.5% (300 ppm HW) |  | 1, X | 1, Y |  | 2, Z, LS |  |
| 1% (300 ppm HW) |  | 1, X | 1, Y |  |  |  |
| 2% (300 ppm HW) |  | 1, X | 1, Y |  |  |  |
| 5% (300 ppm HW) |  | 1, X | 1, Z |  |  |  |
| 10% (300 ppm HW) | 2, Z | 1, X | 1, Z | 2, Z | 1, W |  |
| Iron Chip CI Test |  |  |  |  |  |  |
| TEA Salt |  |  |  |  |  |  |
| 0.5% (300 ppm HW) |  | D | D |  |  | D |
| 1% (300 ppm HW) |  | C | D |  |  | B |
| 2% (300 ppm HW) |  | C | D |  |  | B |
| 5% (300 ppm HW) |  | B | C |  |  | B+ |
| 10% (300 ppm HW) |  | B+ | B |  |  | A |
| $K^+$ Salt |  |  |  |  |  |  |
| 0.5% (300 ppm HW) |  | D | D |  | D |  |
| 1% (300 ppm HW) |  | D | D |  | C |  |
| 2% (300 ppm HW) |  | C | C |  | C |  |
| 5% (300 ppm HW) |  | A | A |  | B |  |
| 10% (300 ppm HW) |  | A | A |  | A |  |

Key:
1 Stable
2 Unstable after 1 hour
3 Unstable after 1 day
4 Precipitate
VLS Very light scum
LS Light scum
MS Medium scum
HS Heavy scum
W clear
X blue-white haze
Y White haze
Z Opaque
A No rust
B Up to 20% rust spots
C Up to 50% rust spots
D Greater than 50% rust spots

TABLE 2

| | DIACID 1525 ½ Ester 2-Ethylhexyl | DIACID 1550 ½ Ester 2-Ethylhexyl | DIACID 1550 ½ Ester Dodecyl | DIACID 1550 XLM ½ Ester 2-Ethylhexyl | DIACID 1550 K+ Salt | DIACID M-T67 |
|---|---|---|---|---|---|---|
| Lubricity Falex P&V Boundary (700 psi) | | Number of Teeth (lower is better) | | | | |
| TEA Salt 1% (300 ppm HW) | | 19 | 17 | | | * |
| K+ Salt 1% (300 ppm HW) | | 36 | 38 | | * | 38 |
| Ramp (psi vs. torque) TEA Salt 1% (300 ppm HW) | | Torque (pounds-inches) | | | 163 | |
| 500 psi | | 16 | 18 | | | |
| 750 psi | | 23 | 24 | | | |
| 1000 psi | | 26 | 26 | | | |
| 1250 psi | | 27 | 30 | | | |
| 1500 psi | | 29 | 32 | | | |
| 1750 psi | | 32 | 36 | | | |
| 2000 psi | | 36 | 43 | | | |
| 2250 psi | | 47 | 46 | | | |
| 2500 psi | | 51 | 52 | | | |
| 2750 psi | | 53 | 55 | | | |
| 3000 psi | | 55 | 56 | | | |
| 3250 psi | | 61 | 59 | | | |
| K+ Salt 1% (300 ppm HW) | | | | | | |
| 500 psi | | 16 | 13 | | | |
| 750 psi | | 24 | 21 | | | |
| 1000 psi | | 28 | 25 | | | |
| 1250 psi | | 31 | 29 | | | |
| 1500 psi | | 35 | 32 | | | |
| 1750 psi | | 38 | 36 | | | |
| 2000 psi | | 41 | 39 | | | |
| 2250 psi | | 43 | 41 | | | |
| 2500 psi | | 45 | 44 | | | |
| 2750 psi | | 48 | 47 | | | |
| 3000 psi | | 49 | 49 | | | |
| 3250 psi | | 52 | 52 | | | |
| 3500 psi | | 54 | 58 | | | |
| 3750 psi | | 57 | | | | |

The potassium and TEA salts of the partial esters of 2-ethylhexanol and dodecanol are significantly more stable in hard water than the corresponding DIACID 1550 salts. The 2-ethylhexanol partial ester salts are more stable than the dodecanol partial ester salts. The dodecanol partial ester potassium salt is not as stable as a 41% active solution in deionized water; lower concentration solutions, however, are stable in 300 ppm hard water.

The potassium salts of both the 2-ethylhexanol and dodecanol partial esters of DIACID 1550 are better corrosion inhibitors and boundary lubricants than the potassium salt of DIACID 1550. Furthermore, both the 2-ethylhexanol and dodecanol partial esters of DIACID 1550 perform better than DIACID M-T67 (67% DIACID 1550 1:2 TEA salt, 8% TEA, and 25% water). The TEA salts of the DIACID 1550 partial esters are better boundary lubricants than DIACID M-T67, but slightly worse corrosion inhibitors. This is likely due to the excess TEA in the DIACID M-T67.

The potassium salt solutions at 2% and 5% demonstrated stability for over 2 months and have a blue-white haze that keeps them from being completely clear. The potassium salts of the DIACID 1550 partial esters completely prevent rust at a lower concentration that the DIACID M-T67 which has 8% excess TEA, but is only 75% active. The salts of the DIACID 1550 partial esters foam significantly less than the corresponding DIACID 1550 salts as the same concentrations, particularly in hard water.

Examining DIACID 1550 Partial Esters of 2-Ethylhexanol or Dodecanol in Generic Semi-Synthetic Metalworking Fluid Formulation. An investigation was conducted to observe the performance of the partial esters in a generic semi-synthetic metalworking fluid formulation. DIACID 1550, DIACID 1550 2-Ethyl-1-hexanol partial ester, and the DIACID 1550 1-Dodecanol partial ester were examined in the formulation. After roughly optimizing the formulation for each product, stabilities of both the concentrates and their 1% active concentration dilutions (in 300 ppm hard water) were observed over a period of at least 10 days. The general formulation of the semi-synthetic metalworking fluid was:

| Component | Weight % |
|---|---|
| Golden Bear 100 SUS Oil | 15.0 |
| ACTRAMIDE 202 | 15.0 |
| ACTRABASE 264 | 5.0 |
| DIACID 1550 or partial ester | 6.1 |
| Butyl CARBITOL ™ | 3.9 |
| KOH, 45% | Q.S. to 100% |
| | q.s. to pH = 8.6-10.5 |

The following general observations were made: (1) in properly balanced formulations, the DIACID 1550 partial ester salts performed noticeably better than the corresponding DIACID 1550; (2) generally, the partial ester salts performed significantly better in hard water; (3) optimization of the level of neutralizing agent and the coupling agent is important; and (4) the HLB of the system can be adjusted to enhance the lubricating and corrosion inhibiting effects of the DIACID 1550 partial esters.

Modifications were made to the formulation in order to examine two couplers (DOWANOL™ TPM (tripropylene glycol methyl ether) and Butyl CARBITOL™ (diethylene glycol monobutyl ether)), examine different amounts of neutralizing ("buffering") agents, the effect of pH, and adjust the HLB. The concentrates were formulated with deionized water and subsequent 1% active concentration dilutions were made with 300 ppm hard water. The concentrates and 1% dilutions were observed for at least 10 days. The inherent foam properties of the DIACID partial esters were determined with the Ross-Miles Foam Test procedure. American Society of Testing and Materials Annual Book of ASTM Standards, Volume 15.04 (1992), Standard D1173 "Standard Test Method for Foaming Properties for Surface-Active Agents", pp 108-109. The clarity, stability, layering, scumming, and relative foam were documented. The results can be found in Table 3 and Table 4.

TABLE 3

Semi-Synthetic Metalworking Fluid

| | 7833-53B | 7833-53E | 7833-54A | 7833-54C | 7833-54E |
|---|---|---|---|---|---|
| Component | | | | | |
| Golden Bear 100 | 15.08 | 15.05 | 15.16 | 14.73 | 14.72 |
| ACTRAMIDE 202 | 15.09 | 15.01 | 15.15 | 14.72 | 14.68 |
| ACTRABASE 264 | 5.11 | 4.98 | 5.22 | 5.07 | 4.87 |
| DIACID 1550 | | | | | |
| 1550 2-ethyl-1-hexanol ½ Ester | 6.10 | 6.06 | 6.10 | 8.93 | 5.93 |
| 1550 dodecanol ½ Ester | | | | | |
| DOWANOL ™ TPM | 1.61 | 1.68 | 1.60 | 4.38 | 3.82 |
| DI Water | 53.28 | 55.26 | 53.61 | 52.10 | 54.06 |
| KOH, 45% | 3.73 | 1.96 | 1.85 | 1.80 | 1.92 |
| Ethox TMO14A | | | | 1.31 | 1.27 |
| Appearance | | | | | |
| Concentrate | | | | | |
| PH (approx . . . )* | | | | | |
| Initial | 2, 6 | 2, 6 | 2, 4 | 1, 2 | 1, 2 |
| 6 Day | 7 | 2, 6 | 2, 5 | 2, 3 | 2, 3 |
| 15 Day | | 2, 6 | 2, 5 | 2, 3 | 2, 3 |
| 1% in 300 ppm HW | | | | | |
| PH (approx . . . )* | | | | | |
| Initial | 6, B/C | 5, C | 5, C | 1, 2, B/C | 2, 3, B/C |
| 1 Hour | | | | 2, 3 | |
| 6 Day | 6, 7, 9 | 2, 6 | 2, 6 | 2, 3 | 2, 3 |
| 15 Day | 7, 0 | 6, 9 | 6, 8 | 2, 3 | 2, 3 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top

TABLE 4

Semi-Synthetic Metalworking Fluid

| Component | 7833-55E | 7833-55G | 7833-56B | 7833-56D | 7833-57A | 7833-57C | 7833-57E |
|---|---|---|---|---|---|---|---|
| Golden Bear 100 | 15.06 | 14.43 | 15.34 | 14.91 | 14.81 | 15.10 | 14.89 |
| ACTRAMIDE 202 | 15.02 | 14.39 | 15.75 | 14.97 | 14.87 | 15.06 | 14.96 |
| ACTRABASE 264 | 5.09 | 4.88 | 5.32 | 5.09 | 5.20 | 5.12 | 5.02 |
| DIACID 1550 | 6.04 | 5.79 | | | | | 6.08 |
| 1550 2-ethyl-1-hexanol ½ Ester | | | | | | 6.09 | |
| 1550 dodecanol ½ Ester | | | 6.43 | 6.08 | 6.17 | | |
| DOWANOL ™ TPM | 1.61 | 5.73 | 6.18 | | | | |

TABLE 4-continued

Semi-Synthetic Metalworking Fluid

| Component | 7833-55E | 7833-55G | 7833-56B | 7833-56D | 7833-57A | 7833-57C | 7833-57E |
|---|---|---|---|---|---|---|---|
| DI Water | 54.67 | 50.47 | 48.38 | 51.36 | 52.82 | 52.51 | 50.58 |
| KOH, 45% | 4.50 | 4.31 | 2.60 | 2.21 | 2.27 | 2.20 | 4.61 |
| Butyl CARBITOL ™ | | | | 5.38 | 3.85 | 3.93 | |

Appearance

Concentrate

| PH (approx..)* | | | | | | | |
|---|---|---|---|---|---|---|---|
| Initial | 6, D | 6, D | 1, 2 | 1, 2 | 1, 2 | 1, 2 | 6 |
| 1 Hour | 7 | 7 | | | | | 7 |
| 1 Day | | | 1, 2 | 1, 2 | | | |
| 5 Day | | | | | 1, 2 | 1, 2 | |
| 6 Day | | | 1, 2 | 1, 2 | | | |
| 15 Day | | | 1, 2 | 1, 2 | 1, 2 | 1, 2 | |

1% in 300 ppm HW

| PH (approx..)* | | | | | | | |
|---|---|---|---|---|---|---|---|
| Initial | 6, C | 6, C | 5, C | 2, 3, B/C | 2, 3, B/C | 2, 3, B/C | 6, B/C |
| 1 Hour | | | | | | | 2, 6, 8 |
| 1 Day | | | 5, 8 | 2, 3 | | | |
| 3 Day | 6, 7, 0 | 6, 7 | | | | | |
| 5 Day | | | | | 2, 4, 9 | 2, 4, 8 | 6, 0 |
| 6 Day | 6, 7, 0 | 6, 7, 0 | 5, 9 | 2, 4, 8 | | | |
| 15 Day | | | | 4, 0 | | | |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top The five formulations in Table 3 were used as range finders for the DIACID 1550 2-Ethyl-1-hexanol partial ester potassium salt. A 1.5 fold excess of neutralizing agent was tried with a lower level of DOWANOL™ TPM coupling solvent in 53B. This was similar practice to excess TEA formulations. The initial appearance of the concentrate was white opaque, but stable. This was marginal so other options were tried. The potassium hydroxide excess was reduced to one third in 53E. The appearance of the concentrate was still white opaque and stable. A non-ionic tall oil fatty acid ethoxylate (Ethox TM014A) was added as a co-emulsifier and hydrophobic/lipophilic balance (HLB) modifier in 54A. A significant improvement to a stable, near clear solution with a light white haze was obtained. In 54C, additional DOWANOL™ TPM coupling solvent was added to the levels used in 54A. The result was a clear, stable concentrate. In 54E, the Ethox TM014A was left out and a lower level of DOWANOL™ TPM was used. The same clear, stable concentrate was obtained. Dilutions with 300 ppm hard water were performed. Initial results for the hard water dilutions gave better results as they progressed from 53B to 54C and 54E. Initially, 54C was clear, but within the first hour developed a very light white haze. Initially, 54E had a very light white haze. Upon aging 6 days, 54C and 54E remained stable with a very light haze for both the concentrate and hard water dilution. As for the other concentrates, 53B layered, 53E was white opaque, but 54A was stable with a white haze. Their hard water dilutions were poorer in performance. The hard water dilution of 53B was white opaque, layered, and had a light scum. The hard water dilutions of 53E and 54A were stable and white opaque.

In Table 4, DIACID 1550 and the two DIACID 1550 partial esters were compared as potassium salts. DIACID 1550 was examined at a low and a high DOWANOL™ TPM level in 55E and 55G. DIACID 1550 performed poorly in the concentrate, layering in the first hour. In 56B, the DIACID1550 1-Dodecanol partial ester was examined at a high DOWANOL™ TPM level and it produced a clear, stable concentrate. The coupling solvent was changed to Butyl CARBITOL™ (diethylene glycol monobutyl ether) because it was specified in the original generic formulation. In 56D and 57A, the DIACID 1550 1-Dodecanol partial ester salts with high and medium levels of Butyl CARBITOL™ were examined with very good results in the concentrates observed (clear and stable). Based on these results in the concentrates, the medium level of Butyl CARBITOL™ was used with DIACID 1550 and the DIACID 1550 2-Ethyl-1-hexanol partial ester (57E and 57C respectively). The DIACID 1550 2-Ethyl-1-hexanol partial ester concentrate (57C) was clear and stable. But the DIACID 1550 concentrate (57E) was white opaque and layered within the first hour. When the 300 ppm hard water dilutions were performed, the DIACID 1550 based concentrates performed poorly.

The DIACID 1550 1-Dodecanol partial ester performed better with Butyl CARBITOL™ coupling solvent when placed in 300 ppm hard water, but as concentrates the Butyl CARBITOL™ and DOWANOL™ TPM based formulations were comparable. The DIACID 1550 2-Ethyl-1-hexanol and 1-Dodecanol partial esters performed very well as concentrates and hard water dilutions with Butyl CARBITOL™ as the coupling solvent in the formulation. It appears that the DIACID 1550 2-Ethyl-1-hexanol partial ester performs slightly better with DOWANOL™ TPM as the coupling solvent. DIACID 1550 1-Dodecanol partial ester, DIACID 1550 2-ethyl-1-hexanol partial ester, and DIACID 1550 were compared under similar formulations in 57 A-E and the partial esters were far better.

Examining DIACID 1550 2-Ethylhexanol Partial Esters Performance in Generic Synthetic Metalworking Fluid Formulations. DIACID 1550, DIACID M-T67, and the DIACID 1550 2-Ethylhexanol partial ester were examined a generic synthetic metalworking fluid formulations. After roughly optimizing the formulation, stabilities of both the concentrates and their 1% active concentration dilutions (in 300 ppm hard water) were observed over a period of at least 10 days. The inherent foam properties were determined with the Ross-Miles Foam Test procedure, as cited above. The following observations were made: (1) in an optimized system, the DIACID 1550 2-Ethylhexanol partial ester significantly outperforms DIACID 1550 in a hard water dilution; (2) pH is important, particularly in a KOH neutralized system; and (3) adjustment of the system HLB is critical for the DIACID 1550 2-Ethylhexanol partial ester.

The partial ester of DIACID 1550 with 2-Ethyl-1-hexanol was formulated into a generic synthetic metalworking fluid. DIACID 1550 was formulated for comparison. The general formulation of the generic synthetic metal working fluid is:

| Component | Weight % |
|---|---|
| EMPHOS TS-230 (EP Lubricant) | 4.1 |
| EM-550 | 10.1 |
| Boundary Lubricant/Corrosion Inhibitor (DIACID 1550 or DIACID 1550 partial ester) | 8.1 |
| Nonionic Surfactant (HLB adjustment) | up to 5% |
| Water, DI | Q.S. to 100% |
| KOH, 45% or TEA | q.s. to pH = 8-10 |

Modifications were made to the formulation in order to examine a coupler (Butyl CARBITOL™), examine different amounts of neutralizing ("buffering") agents, the effect of pH, and adjust the HLB The concentrates were formulated with deionized water and subsequent 1% active concentration dilutions were made with 300 ppm hard water. The concentrates and 1% dilutions were observed for at least 10 days. The clarity, stability, layering, scumming, and relative foam were documented. The results for the synthetic formulation are in Tables 5, 6, and 7.

TABLE 5

DIACID 1550 2-Ethyl-1-hexanol partial ester potassium salt

| Component | 7833-43B | 7833-43D | 7833-44A | 7833-44B | 7833-44D | 7833-44E | 7833-45A | 7833-45C |
|---|---|---|---|---|---|---|---|---|
| DI Water | 82.94 | 82.38 | 82.08 | 81.34 | 80.94 | 81.87 | 80.29 | 88.58 |
| KOH, 45% | 2.71 | 2.51 | 3.95 | 3.56 | 4.02 | 4.02 | 4.11 | 2.15 |
| DIACID M-T67 | | | | | | | | |
| DIACID 2-Ethyl-hexanol Partial ester | 10.13 | 10.04 | 9.95 | 10.05 | 9.87 | 10.07 | 10.02 | 9.27 |
| Emphos TS-230 | 4.21 | 4.06 | 4.01 | 4.01 | 3.99 | 4.04 | 4.02 | |
| Ethox TMO14A | | 1.02 | | 1.04 | 1.00 | | 1.56 | |
| Appearance | | | | | | | | |
| Concentrate | | | | | | | | |
| PH (approx..)* | pH = 7 | pH = 6.5 | pH = 12 | pH = 8.5 | pH = 13 | pH = 12 | pH = 12 | pH = 10 |
| Initial | 5, 2, C | 5, 2, C | 3, 2 | 1, 2 | 1, 2 | 1, 2 | 1, 2 | 1, 2, A |
| 1 Hour | | | | | | 5, 2 | | |
| 1 Day | 6, 2 | | 3, X | 1, 2 | 1, X | 5, X | 1, X | 1, 2 |
| 15 Day | | | | 1, 2 | | | | 3, 2 |
| 1% in 300 ppm HW | | | | | | | | |
| PH (approx..)* | pH = 5 | pH = 5 | | pH = 7.5 | pH = 8.5 | pH = 7.5 | pH = 7.5 | pH = 6.5 |
| Initial | 3, 2, A | 3, 2, A | | 1, 2, B | 1, 2, B | 4, 2 | 1, 2, B | 3, 2, A |
| 1 Hour | | | | | | | 3, 2 | |
| 1 Day | 4, X | | | 5, 2 | 5, 2, 8 | 6, 2, 8 | 5, 2, 8 | 4, 2 |
| 2 Day | | 4, 0 | | | | | | |
| 15 Day | | | | 5, 2, 8 | | | 5, 2 | 4, X |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top The formulations in Table 5 were used as range finders for the DIACID 1550 2-Ethyl-1-hexanol partial ester potassium salt. The EM-550 emulsifier package was left out in order to examine the effect of pH changes on the partial ester salt in the presence of the Emphos TS-230 phosphate ester. Concentrate pH ranges were from 6.5 to 13. A tall oil fatty acid ethoxylate (Ethox TMO14A) was added to selected samples for HLB adjustment. The best initial stability for the concentrates occurred above pH 8. Extended stability for pH13 was poor and pH 12 appeared to be a borderline. Addition of the Ethox TMO14A to the formulation appeared to improve the stability of the hard water dilutions. Formulation 45C does not contain the emulsifier or phosphate ester, and the resulting foam rating demonstrates that the formulation foam is not from the 2-Ethyl-1-hexanol partial ester alone.

The formulations in Table 6 were used to compare DIACID 1550 2-Ethyl-1-hexanol partial ester and DIACID 1550 in a potassium neutralized system. All formulation ingredients were present and in some cases a coupling solvent and/or nonionic surfactant was added in an attempt to optimize the 2-Ethyl-1-hexanol partial ester concentrate formulation stability. The high pH 2-Ethyl-1-hexanol partial ester formulation concentrate (59A) performed very poorly, but the hardwater dilution performed moderately well. The DIACID 1550 formulation concentrate (59C) performed very well, but the hardwater dilution performed poorly. Reduction in pH and addition of the above mentioned stabilizing additives provided significantly enhanced performance in the 2-Ethyl-1-hexanol partial ester based concentrates (59E, 60A, and 60B). All three formulations performed very well as hardwater dilutions.

TABLE 6

Comparison of DIACID 1550 2-ethyl-1-hexanol partial ester and DAICID 1550 in a potassium neutralized system

| Component | 7833-59A | 7833-59C | 7833-59E | 7833-60A | 7833-60B | 7833-60C |
|---|---|---|---|---|---|---|
| DI Water | 71.04 | 68.35 | 65.70 | 65.97 | 70.65 | 63.19 |
| KOH, 45% | 6.63 | 8.94 | 6.14 | 5.13 | 3.73 | 4.71 |
| DIACID 1550 | | 8.07 | | | | |
| DIACID 2-Ethyl-hexanol Partial ester | 8.01 | | 7.41 | 9.83 | 8.21 | 11.57 |
| EM-550 | 10.18 | 10.36 | 9.41 | 9.89 | 10.05 | 9.48 |
| Emphos TS-230 | 4.14 | 4.28 | 3.83 | 4.10 | 4.18 | 3.86 |
| Ethox TMO14A | | | | | 3.18 | 3.28 |
| Butyl CARBITOL ™ | | | 3.20 | | | |
| Tergitol NP-7 | | | 4.31 | | | |
| Tergitol NP-9 | | | | 5.08 | | |
| Concentrate | | | | | | |
| PH (approx..)* | pH = >13 | pH = 12 | pH = 11 | pH = 9.5 | pH = 8 | pH = 13 |
| Initial | 1, 2, C | 1, 2, D | 1, 2, C | 1, 2, D | 1, 2, C | 1, 2, D |
| 1 Hour | 5, 2 | 1, 2 | 1, 2 | 1, 2 | 1, 2 | 1, 2 |
| 1 Day | 7, X | 1, 2 | 1, 2 | | | |
| 3 Day | | | | 1, 2 | 1, 2 | 1, 2 |
| 4 Day | 7, X | 1, 2 | 7, X | 1, 2 | 1, 2 | 1, 2 |
| 15 Day | 7, X | 1, 2 | 7, X | 1, 2 | 1, 2 | 1, 2 |
| 1% in 300 ppm HW | | | | | | |
| PH (approx..)* | pH = 5 | pH = 5 | | pH = 7.5 | pH = 8.5 | pH = 7.5 |
| Initial | 1, 2, B | 3, 2, D | 1, 2, C | 1, 2, D | 1, 2, C | |
| 1 Hour | 1, 2 | 4, 2 | 1, 2 | 1, 2 | 1, 2 | |
| 1 Day | 1, 2 | 4, 8 | 1, 2 | | | |
| 3 Day | | | | 1, 2 | 1, 2 | |
| 4 Day | 3, 2 | 4, 8 | 1, 2 | 1, 2 | 1, 2 | |
| 5 Day | 3.2 | 4, 8 | 1, 2 | | | |
| 15 Day | 3, 2 | 4, 8 | 1, 2 | 1, 2 | 1, 2 | |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top

TABLE 7

| Component | 7833-58A | 7833-58C | 7833-58E | 7833-58G |
|---|---|---|---|---|
| DI Water | 70.49 | 70.31 | 70.34 | 61.40 |
| TEA, 99% | 5.11 | 8.66 | 9.37 | 7.56 |
| DIACID M-T67 | 10.16 | | | |
| DIACID 1550 | | | 6.06 | |
| DIACID 2-Ethylhexanol Partial ester | | 6.76 | | 5.90 |
| EM-550 | 10.20 | 10.14 | 10.14 | 8.86 |
| Emphos TS-230 | 4.04 | 4.13 | 4.10 | 3.61 |
| Butyl CARBITOL ™ | | | | 2.99 |
| Tergitol NP-7 | | | | 5.48 |
| Tergitol NP-9 | | | | 4.20 |
| Concentrate | | | | |
| PH (approx . . . )* | pH = >13 | pH = 12 | pH = 11 | pH = 9.5 |
| Initial | 1, 2, D | 5, C | 1, 2, D | 1, 2, D |
| 1 Hour | | | | 1, 2 |
| 2 Day | 1, 2 | 7, X | 1, 2 | |
| 3 Day | | | | 1, 2 |
| 4 Day | | | | 1, 2 |
| 5 Day | 1, 2 | 7, X | 1, 2 | |
| 15 Day | 1, 2 | 7, X | 1, 2 | 1, 2 |
| 1% in 300 ppm HW | | | | |
| PH (approx . . . )* | pH = 5 | pH = 5 | | pH = 7.5 |
| Initial | 1, 2, D | 6, C | 1, 2, D | 1, 2, D |
| 1 Hour | | | 4, 2 | 1, 2 |
| 2 Day | 5, 2 | 5, 0 | 5, 8 | |
| 3 Day | | | | 1, 2 |
| 5 Day | 5, 2 | 5, 0 | 5, 9 | |
| 15 Day | 5, 2 | 5, 0 | 5, 9 | 1, 2 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top The formulations in Table 7 examine the system with triethanolamine (TEA) as the neutralizing agent. Each formulation contains approximately 6% TEA in excess of the amount needed to neutralize the DIACID 1550 or DIACID 1550 2-Ethyl-1-hexanol partial ester. Formulation 58A has pre-made DIACID M-T67, while 58E contains DIACID 1550 neutralized in situ. It should be noted that 58A (DIACID M-T67) and 58E (DIACID 1550) performed differently. Modification of the HLB and/or addition of a coupling solvent were previously demonstrated to dramatically improve the performance of the partial ester formulations. This was illustrated again in when comparing 58C (2-Ethyl-1-hexanol) with 58G.

Examining DIACID 1550 Partial Ester of 2-Ethyl-1-hexanol or 1-Dodecanol in Generic Metalworking Fluid Formulations. An investigation was conducted to observe the performance of the 2-Ethyl-1-hexanol and 1-Dodecanol DIACID 1550 partial esters in generic synthetic and semi-synthetic metalworking fluid formulations. DIACID 1550, DIACID 1550 2-Ethyl-1-hexanol partial esters, and DIACID 1550 1-Dodecanol partial esters were examined in the formulations. Several additives were used to adjust the HLB, or the solvency, of the formulations to determine the best overall stability. After adjusting the formulations, stabilities of both the concentrates and their 1% active concentration dilutions (in 300 ppm hard water) were observed over a period of at least 10 days. The inherent foam properties of the neutralized partial esters were determined with the Ross-Miles Foam Test procedure, as cited above.

The following observations were made: (1) in the optimized TEA based semi-synthetic system, the DIACID 1550 2-Ethyl-1-hexanol partial esters and DIACID 1-Dodecanol partial esters significantly outperformed DIACID 1550 in the concentrate and the hard water dilutions; (2) in the TEA based synthetic system, the unmodified formulation gave poor results; (3) TEA based synthetic system was difficult to stabilize, but IGEPAL CO-530 an octylphenol ethoxylate (HLB=10.8) worked well, yielding significant improvement with the partial esters; (4) a blend of IGEPAL CO-530 with OCD-480 (a PEG-400 diester of L-5) with HLB=10.2, worked well, yielding significant improvement with the partial esters; (5) in the potassium hydroxide (KOH) based synthetic system in which the HLB was balanced, the partial esters were far superior to DIACID 1550; (6) the alcohol ethoxylates (linear or alkylphenol) with HLB values of 10.5-12.5 did well with regard to stabilizing the partial ester based potassium hydroxide formulations; (7) the blends of OCD-480 (a PEG-400 diester of L-5) and alcohol ethoxylates (linear or alkylphenol) with resulting HLB values of 10.5 to 11.5 did well with regard to stabilizing the partial ester potassium hydroxide based formulations; (8) the Tall Oil Fatty Acid ethoxylate with a HLB value of 13.7 did well with regard to stabilizing the partial ester potassium hydroxide based formulations; (9) the DIACID 1550 12 mole ethoxylate with a HLB value of 12.0 did the best overall with regard to stabilizing the partial ester potassium hydroxide based formulations; (10) system adjustments did not improve the DIACID 1550 performance anywhere near as well as the improvement obtained in the performance of the DIACID 1550 partial esters; and (11) adjustment of the system HLB enhanced the stability of the concentrates and the hard water dilution.

Semi-Synthetic Formulations. The partial esters of DIACID 1550 with 2-Ethyl-1-hexanol or 1-Dodecanol were formulated into a TEA based generic semi-synthetic metalworking fluid. DIACID1550 was formulated for comparison. The general formulation is shown in Table 8. The concentrates were formulated with deionized water, and subsequently 1% active concentration dilutions were made with 300 ppm hard water. The concentrates and dilutions were observed for at least 10 days. Results for the TEA based semi-synthetic metalworking fluid formulation, including clarity, stability, layering, scumming and relative foam can be found in Tables 9.

TABLE 8

TEA Based Semi-Synthetic Metalworking Fluid Concentrate Formulation.

| Component | Weight % |
|---|---|
| Golden Bear 100 SUS Oil | 15.0 |
| ACTRAMIDE 202 | 15.0 |
| ACTRABASE 264 | 5.0 |
| DIACID 1550 or partial ester | 6.2 |
| Butyl CARBITOL ™ | 3.9 |
| TEA 99% 1:1 Equivalents* and 5% excess | |
| Water, DI | Q.S. to 100% |

*based on Acid number of DIACID 1550 or partial ester

TABLE 9

TEA Based Semi-Synthetic Metalworking Formulation

| | 7833-62A | 7833-62B | 7833-62C |
|---|---|---|---|
| Component | | | |
| Golden Bear 100 | 15.13 | 15.07 | 14.93 |
| ACTRAMIDE 202 | 15.03 | 15.12 | 15.11 |
| ACTRABASE 264 | 5.18 | 5.06 | 5.02 |
| DIACID 1550 | 6.44 | | |
| DIACID1550 2-ethyl-1-hexanol ½ Ester | | 6.17 | |
| DIACID1550 dodecanol ½ Ester | | | 6.04 |
| TEA, 99% | 9.76 | 6.96 | 6.85 |
| DI Water | 44.40 | 47.61 | 47.67 |
| Butyl CARBITOL ™ | 4.05 | 4.00 | 4.02 |
| *Appearance* | | | |
| Concentrate | | | |
| Initial | 6 | 1, 2 | 1, 2 |
| 1 Hour | 7 | | |
| 1 Day | 7 | 1, 2 | 1, 2 |
| 2 Day | | 1, 2 | 1, 2 |
| 6 Day | | 1, 2 | 1, 2 |
| 15 Day | | 1, 2 | 1, 2 |
| 1% in 300 ppm HW | | | |
| Initial | 6, B | 3, 2, C | 3, 2, C/D |
| 1 Hour | 6, 0 | | |
| 1 Day | 6, 0 | 4, 2 | 4, 2 |
| 2 Day | 6, 0 | 4, 2 | 4, 2 |
| 6 Day | 6, 0 | 4, 2 | 4, 2 |
| 15 Day | 6, 0 | 5, 9/0 | 5, 0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Items 62A, 62B, and 62C are the results for DIACID 1550, the 1550 2-Ethyl-1-hexanol partial ester, and the DIACID 1550 1-Dodecanol partial ester, respectively. DIACID 1550 performs poorly in the concentrate and the hard water dilution. The DIACID 1550 2-Ethyl-1-hexanol and 1-Dodecanol partial esters performed very well in the concentrate and good in the hard water dilutions.

TEA Based Synthetic Formulation. The partial esters of DIACID 1550 with either 2-Ethyl-1-hexanol or 1-Dodecanol were formulated into a generic synthetic metalworking fluid. DIACID 1550 was formulated for comparison. The general formulation is shown in Table 10. Modifications were made to the formulation in order to examine a coupler (Butyl CARBITOL™), and adjust the HLB The concentrates were formulated with deionized water, and subsequently 1% active concentration dilutions were made with 300 ppm hard water. The concentrates and dilutions were observed for at least 10 days. The clarity, stability, layering, scumming, and relative foam were documented. The results for the TEA based synthetic metalworking fluid formulation can be found in Tables 11-14.

TABLE 10

TEA Based Synthetic Metalworking Fluid Concentrate Formulation

| Component | Weight % |
|---|---|
| EMPHOS TS-230 (EP Lubricant) | 4.1 |
| EM-550 | 10.1 |
| Boundary Lubricant/Corrosion Inhibitor (DIACID 1550 or partial ester) | 8.1 |
| Nonionic Surfactant (HLB adjustment) | up to 5.0 |
| TEA 99% 1:1 equivalent ration (based on Acid number of DIACID 1550 or partial ester) | |
| TEA 99% 1:1 Equivalents* and 5% excess | 5.0 |
| Water, DI | Q.S. to 100% |

TABLE 11

Unmodified Synthetic Metalworking Formulation with TEA

| | 7833-63A | 7833-63B | 7833-63C |
|---|---|---|---|
| Component | | | |
| DI Water | 66.61 | 70.27 | 70.46 |
| TEA, 99% | 10.84 | 7.33 | 7.08 |
| DIACID 1550 | 8.11 | | |
| 1550 2-ethyl-1-hexanol ½ Ester | | 8.14 | |
| 1550 dodecanol ½ Ester | | | 8.13 |
| EM-550 | 10.26 | 10.10 | 10.15 |
| EMPHOS TS-230 | 4.17 | 4.15 | 4.18 |
| *Appearance* | | | |
| Concentrate | | | |
| Initial | 1, 2, D+ | 6, B | 6, B |
| 1 Hour | 1, 2 | 7 | 7 |
| 1 Day | 1, 2 | 7 | 7 |
| 15 Day | 1, 2 | 7 | 7 |
| 1% in 300 ppm HW | | | |
| Initial | 3, C/D | 5, B | 5, C |
| 1 Hour | 3, 8 | 5, 9 | 5, 9 |
| 1 Day | 3, 9 | 6, 0 | 6, 0 |
| 15 Day | 5, 9 | 6, 0 | 6, 0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top The results for the unmodified base formulation are found in Table 11. Items 63A, 63B, and 63C are the results for DIACID 1550, the 1550 2-Ethyl-1-hexanol half ester, and the 1550 1-Dodecanol partial ester, respectively. DIACID 1550 performed well in the concentrate, but poorly in the hard water dilution. The DIACID 1550 2-Ethyl-1-hexanol partial ester, and 1-Dodecanol partial ester performed very poorly in the concentrate and the hard water dilutions.

TABLE 12

Synthetic Metalworking Formulation with TEA and Butyl CARBITOL™ Modifications

| | 7833-64A1 | 7833-64B | 7833-64C |
|---|---|---|---|
| Component | | | |
| DI Water | 56.43 | 60.53 | 60.75 |
| TEA, 99% | 9.55 | 6.42 | 6.12 |
| DIACID 1550 | 7.43 | | |
| 1550 2-ethyl-1-hexanol ½ Ester | | 7.07 | |
| 1550 dodecanol ½ Ester | | | 7.06 |
| EM-550 | 8.95 | 8.74 | 8.74 |
| EMPHOS TS-230 | 3.65 | 3.59 | 3.63 |
| Butyl CARBITOL™ | 14.00 | 13.65 | 13.69 |
| Appearance | | | |
| Concentrate | | | |
| Initial | 1, 2, D+ | 6, B | 6, B/C |
| 1 Hour | | 7 | 7 |
| 1 Day | 1, 2 | 7 | 7 |
| 4 Day | 1, 2 | 7 | 7 |
| 6 Day | 1, 2 | | |
| 15 Day | 1, 2 | | |
| 1% in 300 ppm HW | | | |
| Initial | 3, D | | |
| 1 Hour | 4, 9 | | |
| 1 Day | 3, 9 | | |
| 4 Day | 4, 9 | | |
| 6 Day | 5, 9/0 | | |
| 15 Day | 5, 9/0 | | |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Table 12 contains the results for modifications with Butyl CARBITOL™, which had performed well in stabilizing the semi-synthetic formulation. Excessive amounts of Butyl CARBITOL™ were unable to improve the performance of the TEA based synthetic formulation.

TABLE 13

Synthetic Metalworking Formulation with TEA and ETHOX TMO14A or TERGITOL™ NP-9 Modification

| | 7833-65A | 7833-66A |
|---|---|---|
| Component | | |
| DI Water | 63.61 | 63.67 |
| TEA, 99% | 10.85 | 10.85 |
| DIACID 1550 | 8.15 | 8.13 |
| EM-550 | 10.13 | 10.16 |
| EMPHOS TS-230 | 4.18 | 4.13 |
| Ethox TMO14A | 3.07 | |
| Tergitol NP-9 | | 3.06 |
| Concentrate | | |
| Initial | 1, 2, D | 1, 2, D |
| 1 Day | 1, 2 | 1, 2 |
| 4 Day | 1, 2 | 1, 2 |
| 6 Day | 1, 2 | 1, 2 |
| 15 Day | 1, 2 | 1, 2 |
| 1% in 300 ppm HW | | |
| Initial | 1, 2, D+ | 1, 2, D |
| 1 Hour | 3, 9 | |
| 1 Day | 3, 9 | 1, 2 |
| 4 Day | 4, 9/0 | 4, 8 |
| 6 Day | 5, 9/0 | 5, 8 |
| 15 Day | 5, 9/0 | 5, 8 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Table 13 contains the results for the modifications of the DIACID 1550 TEA based synthetic formulation with Ethox TM014A (14 mole ethoxylate of tall oil fatty acid, TOFA) or TERGITOL NP-9 (a 9 mole ethoxylate of nonylphenol). The unmodified DIACID 1550 TEA based synthetic formulation had a stable concentrate. Therefore, improvement was not detected in the concentrate. However, the TERGITOL NP-9 improved the hard water dilution stability from less than 1 hour up to greater than 1 day, but less than 4 days. The Ethox TMO14A did not improve the performance of the DIACID 1550 TEA based synthetic formulation with regard to hard water dilution stability.

TABLE 14

HLB Optimization of Synthetic Metalworking Formulation with TEA

| Component | 7833-67A | 7833-67B | 7833-67C | 7833-67D | 7833-67E | 7833-67F | 7833-68C |
|---|---|---|---|---|---|---|---|
| DI Water | 65.03 | 65.06 | 64.84 | 65.01 | 64.77 | 64.94 | 64.45 |
| TEA, 99% | 7.28 | 7.30 | 7.22 | 7.28 | 7.56 | 7.36 | 7.22 |
| 1550 2-ethyl-1-hexanol ½ Ester | 8.11 | 8.18 | 8.16 | 8.18 | 8.04 | 8.10 | 8.18 |
| EM-550 | 10.21 | 10.17 | 10.10 | 10.15 | 10.32 | 10.32 | 10.03 |
| EMPHOS TS-230 | 4.32 | 4.14 | 4.27 | 4.17 | 4.19 | 4.28 | 4.22 |
| Tergitol NP-4 | 5.04 | | | | | 3.04 | |
| Tergitol NP-7 | | | | | 5.11 | 1.52 | |
| IGEPAL CO-430 | | | | | | | 2.96 |
| IGEPAL CO-530 | | 5.15 | | 3.86 | | | 2.95 |
| OCD-480 | | | 5.41 | 1.36 | | 0.54 | |
| Appearance | | | | | | | |
| Concentrate | | | | | | | |
| Initial | 4, 2 | 1, 2 | 4, 2 | 4, 2 | 3, 2 | 1, 2 | 1, 2, C/D |
| 1 Hour | | | 6, 2 | | | | |
| 1 Day | 4, 2 | 1, 2 | 6, 2 | 4, 2 | 3, 2 | 1, 2 | 1, 2 |
| 3 Day | 4, 2 | 1, 2 | 6, 2 | 4, 2 | 3, 2 | 1, 2 | 1, 2 |
| 6 Day | | 1, 2 | | 4, 2 | | 1, 2 | 1, 2 |
| 15 Day | | 1, 2 | | 7* | | 1, 2 | 1, 2 |
| 1% in 300 ppm HW | | | | | | | |
| Initial | | 1, 2, C/D | | 1, 2, D | | 1, 2, C/D | 1, 2, C |
| 1 Day | | 4, 2 | | 4, 2 | | 4/5, 2 | 4/5, 2 |
| 4 Day | | 4, 2 | | 4, 2 | | 4/5, 2 | 4/5, 2 |
| 6 Day | | 4, 2 | | 4, 2 | | 4/5, 2 | 4/5, 2 |
| 15 Day | | 4, 2 | | 4, 9 | | 4/5, 2 | 4/5, 2 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top In Table 14, alkylphenol ethoxylates and OCD-480, which is a TOFA polyethylene glycol diester (TOFA-PEG), are used to optimize the HLB of the DIACID 1550 2-ethyl-1-hexanol partial ester TEA based synthetic formulation. Additive combinations with HLB of 9.5 to 11 perform well in the concentrate and the hard water dilutions.

Potassium Hydroxide Based Synthetic Formulation. The partial esters of DIACID 1550 with either 2-Ethyl-1-hexanol or 1-Dodecanol were formulated into a generic synthetic metalworking fluid. DIACID 1550 was formulated for comparison. The general formulation is shown in Table 15. Modifications were made to the formulation in order to examine a coupler (e.g. Butyl CARBITOL™), and adjust the HLB. The concentrates were formulated with deionized water, and subsequently 1% active concentration dilutions were made with 300 ppm hard water. The concentrates and dilutions were observed for at least 10 days. The clarity, stability, layering, scumming, and relative foam were documented. Results for the potassium hydroxide based synthetic formulation can be found in Tables 16-20.

TABLE 15

Potassium Hydroxide Based Synthetic Metalworking Fluid Concentrate Formulation.

| Component | Weight % |
|---|---|
| EMPHOS TS-230 (EP Lubricant) | 4.1 |
| EM-550 | 10.1 |
| Boundary Lubricant/Corrosion Inhibitor (DIACID 1550 or partial ester) | 8.1 |
| Nonionic Surfactant (HLB adjustment) | up to 5.0 |
| Potassium Hydroxide, 45% | q.s. to pH = 8-10 |
| Water, DI | Q.S. to 100% |

TABLE 16

Synthetic Metalworking Formulation with Potassium Hydroxide

| Component | 7833-72C | 7833-72B | 7833-72A | 7833-71C | 7833-71B | 7833-71A |
|---|---|---|---|---|---|---|
| DI Water | 70.57 | 69.54 | 64.29 | 73.38 | 73.41 | 67.52 |
| KOH, 45% | 3.47 | 3.83 | 9.74 | 3.62 | 3.96 | 9.76 |
| DIACID 1550 | | | 8.19 | | | 8.06 |
| 1550 2-ethyl-1-hexanol ½ Ester | | 8.52 | | | 8.14 | |
| 1550 dodecanol ½ Ester | 8.39 | | | 8.11 | | |
| EM-550 | 10.06 | 10.42 | 10.13 | 10.54 | 10.26 | 10.46 |
| EMPHOS TS-230 | 4.07 | 4.18 | 4.18 | 4.35 | 4.23 | 4.20 |
| Ethox TMO14A | 3.43 | 3.52 | 3.47 | | | |
| Appearance | | | | | | |
| Concentrate | | | | | | |
| Initial | 1, 2, C | 1, 2, C | 1, 2, D | 4, 2, C | 4, 2, C | 1, 2, D |
| 1 Hour | | | | 5, 2 | 5, 2 | |
| 1 Day | 1, 2 | 1, 2 | 1, 2 | 7 | 7 | 1, 2 |
| 2 Day | 1, 2 | 1, 2 | 1, 2 | | | |
| 3 Day | 4, 2 | 1, 2 | 1, 2 | | | 1, 2 |
| 6 Day | 7, X | 1, 2 | 1, 2 | | | 1, 2 |
| 15 Day | | 1, 2 | 1, 2 | | | 1, 2 |
| 1% in 300 ppm HW | | | | | | |
| Initial | 1, 2, B/C | 1, 2, B/C | 4, D, 8 | 4, 2, A | 4, 2, A | 3, D, 8 |
| 1 Hour | | | | 4, 2 | 4, 2 | 3, 9 |
| 1 Day | 1, 2 | 1, 2 | 3, 0 | 4, 0 | 5, 0 | 3, 0 |
| 2 Day | 1, 2 | 1, 2 | 4, 0 | 4, 0 | 5, 0 | 4, 0 |
| 3 Day | 1, 2 | 1, 2 | 4, 0 | 4, 0 | 5, 0 | 4, 0 |
| 6 Day | 1, 2 | 1, 2 | 4, 0 | 4, 0 | 5, 0 | 4, 0 |
| 15 Day | 1, 2 | 1, 2 | 4, 0 | 4, 0 | 5, 0 | 4, 0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top The results for the unmodified potassium hydroxide based synthetic formulation are found in Table 16, along with the results for the formulation modified with ETHOX TMO14A. Items 71A, 71B, and 71C are the results for DIACID 1550, the DIACID 1550 2-Ethyl-1-hexanol partial ester, and the DIACID 1550 1-Dodecanol partial ester, respectively. DIACID 1550 performed well in the concentrate, but poorly in the hard water dilution. Items 72A, 72B, and 72C are the results for the Ethox TM014A modified formulation with DIACID 1550, the DIACID 1550 2-Ethyl-1-hexanol partial ester, and the DIACID 1550 1-Dodecanol partial ester, respectively. DIACID 1550 performed well in the concentrate. However, the DIACID 1550 2-Ethyl-1-hexanol partial ester performed very well in the concentrate and the hard water dilution. The DIACID 1550 1-Dodecanol partial ester performed significantly better in the concentrate and very well in the hard water dilution.

TABLE 17

Synthetic Metalworking Formulation with Potassium Hydroxide

| | 7833-73C | 7833-73B | 7833-73A |
|---|---|---|---|
| Component | | | |
| DI Water | 70.19 | 69.70 | 63.68 |
| KOH, 45% | 3.56 | 3.83 | 9.81 |
| DIACID 1550 | | | 8.58 |
| 1550 2-ethyl-1-hexanol ½ Ester | | 8.35 | |
| 1550 dodecanol ½ Ester | 8.39 | | |
| EM-550 | 10.15 | 10.15 | 10.11 |
| EMPHOS TS-230 | 4.18 | 4.19 | 4.29 |
| Butyl CARBITOL ™ | 3.54 | 3.77 | 3.53 |

TABLE 17-continued

Synthetic Metalworking Formulation with Potassium Hydroxide

|  | 7833-73C | 7833-73B | 7833-73A |
|---|---|---|---|
| Appearance | | | |
| Concentrate | | | |
| Initial | 6, C | 6, C | 1, 2, D+ |
| 1 Day | 7.00 | 7.00 | 1, 2 |
| 2 Day | | | 1, 2 |
| 3 Day | | | 1, 2 |
| 6 Day | | | 1, 2 |
| 15 Day | | | 1, 2 |
| 1% in 300 ppm HW | | | |
| Initial | 4, A | 4, A | 3, D+, 9 |
| 1 Day | 4, 0 | 4, 0 | 4, 0 |
| 2 Day | 4, 0 | 4, 0 | 4, 0 |
| 3 Day | 4, 0 | 4, 0 | 4, 0 |
| 6 Day | 4, 0 | 4, 0 | 4, 0 |
| 15 Day | 4, 0 | 4, 0 | 4, 0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Table 17 contains the results for the potassium hydroxide based synthetic formulation modified with Butyl CARBITOL™. There was no improvement of performance with Butyl CARBITOL™. As noted previously with the TEA based synthetic formulation, Butyl CARBITOL™ does not improve the performance of the synthetic formulation but readily improves the performance of the semi-synthetic formulation where it acts as an emulsifying solvent.

TABLE 18

Synthetic Metalworking Formulation with Potassium Hydroxide.

| | 7833-74E | 7833-74D | 7833-74C | 7833-74B | 7833-74A |
|---|---|---|---|---|---|
| Component | | | | | |
| DI Water | 69.81 | 69.95 | 69.94 | 70.02 | 69.98 |
| KOH, 45% | 3.83 | 3.86 | 3.83 | 3.86 | 3.85 |
| 1550 2-ethyl-1-hexanol ½ Ester | 8.17 | 8.25 | 8.28 | 8.18 | 8.22 |
| EM-550 | 10.14 | 10.16 | 10.11 | 10.19 | 10.26 |
| EMPHOS TS-230 | 4.23 | 4.25 | 4.36 | 4.21 | 4.22 |
| IGEPAL CO-630 | | | 3.48 | | |
| NEODOL 91-6 | | | | 3.54 | |
| NEODOL 91-8 | | | | | 3.48 |
| OCD-383 | 1.85 | | | | |
| OCD-384 | 1.97 | 3.53 | | | |

TABLE 18-continued

Synthetic Metalworking Formulation with Potassium Hydroxide.

| | 7833-74E | 7833-74D | 7833-74C | 7833-74B | 7833-74A |
|---|---|---|---|---|---|
| Appearance | | | | | |
| Concentrate | | | | | |
| Initial | 1, 2, C | 3, 2, C | 1, 2, C | 1, 2, D+ | 1, 2, D+ |
| 1 Hour | 3, 2 | 5, 2 | | | 3, 2 |
| 2 Hours | | | | | 4, 2 |
| 1 Day | 5, 7 | 5, 7 | 1, 2 | 1, 2 | 5, 7 |
| 2 Day | | | 1, 2 | 1, 2 | |
| 6 Day | | | 1, 2 | 1, 2 | |
| 15 Day | | | 1, 2 | 1, 2 | |
| 1% in 300 ppm HW | | | | | |
| Initial | 3, 2, B/C | 3, 2, B | 1, 2, C | 1, 2, D | 1, 2, D |
| 1 Day | 3, 9/0 | 3, 9/0 | 1, 2 | 1, 2 | 1, 9 |
| 6 Day | 3, 9/0 | 3, 9/0 | 1, 2 | 1, 2 | 1, 9/0 |
| 15 Day | 3, 9/0 | 3, 9/0 | 1, 2 | 1, 2 | 1, 9/0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top

TABLE 19

Synthetic Metalworking Formulation with Potassium Hydroxide

| | 7833-75E | 7833-75D | 7833-75C | 7833-75B | 7833-75A |
|---|---|---|---|---|---|
| Component | | | | | |
| DI Water | 70.29 | 70.15 | 70.26 | 70.19 | 70.13 |
| KOH, 45% | 3.85 | 3.85 | 3.85 | 3.83 | 3.86 |
| 1550 2-ethyl-1-hexanol ½ Ester | 8.12 | 8.15 | 8.11 | 8.15 | 8.19 |
| EM-550 | 10.11 | 10.18 | 10.09 | 10.16 | 10.07 |
| EMPHOS TS-230 | 4.13 | 4.17 | 4.14 | 4.16 | 4.21 |
| Tergitol NP-7 | | 3.49 | | | |
| IGEPAL CO-530 | | | | 3.51 | |
| TRITON X-114 | | | 3.55 | | |
| NEODOL 23-5 | | | | | 3.54 |
| OCD-383 | 3.51 | | | | |
| Appearance | | | | | |
| Concentrate | | | | | |
| Initial | 1, 2, C | 1, 2, D | 1, 2, D | 1, 2, C | 1, 2, D |
| 1 Day | 1, 2 | 1, 2 | 1, 2 | 1, 2 | 1, 2 |
| 5 Day | 1, 2 | 1, 2 | 1, 2 | 1, 2 | 1, 2 |
| 6 Day | 1, 2 | 1, 2 | 1, 2 | 1, 2 | 1, 2 |
| 15 Day | 1, 2 | 1, 2 | 1, 2 | 1, 2 | 1, 2 |
| 1% in 300 ppm HW | | | | | |
| Initial | 1, 2, B+ | 1, 2, C | 1, 2, D | 1, 2, C/D | 1, 2, D |
| 1 Day | 1, 2 | 1, 2 | 1, 2 | 1, 2 | 1, 2 |

TABLE 19-continued

Synthetic Metalworking Formulation with Potassium Hydroxide

|  | 7833-75E | 7833-75D | 7833-75C | 7833-75B | 7833-75A |
|---|---|---|---|---|---|
| 6 Day | 1, 2 | 1, 2 | 1, 2 | 1, 2 | 1, 2 |
| 15 Day | 1, 2 | 1, 2 | 1, 2 | 1, 2 | 1, 2 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top The results reported in Table 18 and Table 19 represent the examination of the 2-Ethyl-1-hexanol partial ester in the potassium hydroxide based synthetic formulation modified with HLB adjusting additives of various chemistries. The additives consist of alkylphenol ethoxylates, linear alcohol ethoxylates, and Ingevity DIACID 1550 ethoxylates. The additives with HLB values between 10.5 and 12.5 worked best. But IGEPAL CO-630 (alkylphenol ethoxylate with HLB of 13.0; and in particular, nonyl phenol ethoxylate) performed very well. Another additive consisting of a blend of DIACID1550 ethoxylates (OCD-383 and OCD-384) performed poorly. It had a 12.6 calculated HLB. It should be noted here that the Ingevity DIACID 1550 ethoxylate with 12 moles EO (OCD-383) was one of the best performers and its formulation had the lowest foam.

TABLE 20

Synthetic Metalworking Formulation with KOH.

|  | 7833-76D | 7833-76C | 7833-76B | 7833-76A |
|---|---|---|---|---|
| Component |  |  |  |  |
| DI Water | 70.03 | 70.15 | 69.16 | 69.90 |
| KOH, 45% | 3.87 | 3.86 | 3.85 | 3.88 |
| 1550 2-ethyl-1-hexanol ½ Ester | 8.18 | 8.19 | 8.12 | 8.32 |
| EM-550 | 10.14 | 10.19 | 9.98 | 10.12 |
| EMPHOS TS-230 | 4.29 | 4.13 | 4.09 | 4.29 |
| IGEPAL CO-630 |  |  |  | 1.74 |
| NEODOL 91-8 |  | 1.75 | 2.40 |  |
| OCD-384 | 1.74 |  |  |  |
| OCD-480 | 1.73 | 1.74 | 2.40 | 1.75 |
| Appearance |  |  |  |  |
| Concentrate |  |  |  |  |
| Initial | 1, 2, B/C | 1, 2, D | 1, 2, D | 1, 2, C |
| 1 Day | 1, 2 | 1, 2 | 1, 2 | 1, 2 |
| 5 Day | 1, 2 | 1, 2 | 1, 2 | 1, 2 |
| 6 Day | 1, 2 | 1, 2 | 1, 2 | 1, 2 |
| 15 Day | 1, 2 | 1, 2 | 1, 2 | 1, 2 |
| 1% in 300 ppm HW |  |  |  |  |
| Initial | 1, 2, C- | 1, 2, C | 1, 2, C | 1, 2, C |
| 1 Day | 1, 2 | 1, 2 | 1, 2 | 1, 2 |
| 6 Day | 1, 2 | 1, 2 | 1, 2 | 1, 2 |
| 15 Day | 1, 2 | 1, 2 | 1, 2 | 1, 2 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Table 20 contains results of the investigation of the 2-Ethyl-1-hexanol partial ester in the potassium hydroxide based synthetic formulation modified with HLB adjusting additives consisting of OCD-480(TOFA-PEG diester) blended with either an alkylphenol ethoxylate, a linear alcohol ethoxylate, or a Ingevity DIACID 1550 ethoxylate. The additive blends had HLB values ranging from 10.7 to 11.2, and they each performed very well. The TOFA-PEG diester and the DIACID 1550 ethoxylates also demonstrate the potential to be non-petroleum, renewable resource based metalworking fluid additives.

Comparing DIACID Partial Ester of n-Pentanol with 2-Ethyl-1-hexanol and 1-Dodecanol Analogues in Semi-synthetic and Synthetic Metalworking Fluid Formulations. An investigation was conducted to observe the performance of the DIACID 1550 n-Pentanol partial ester, and compare it to 2-Ethyl-1-hexanol and 1-Dodecanol partial esters, in generic synthetic and semi-synthetic working fluid formulations. DIACID 1550 n-Pentanol partial esters were examined in the semi-synthetic and synthetic metalworking fluid formulations and compares to data for DIACID 1550, DIACID 1550 2-Ethyl-1-hexanol partial esters, and DIACID 1550 1-Dodecanol partial ester. Selected additives were used to adjust the HLB, or the solvency, of the formulations based on the overall stability determined in previous experiments. After adjusting the formulations, stabilities of both the concentrates and their 1% active concentration dilutions (in 300 ppm hard water) were observed over a period of at least 10 days.

The following observations were made: (1) in the optimized TEA based semi-synthetic system, the DIACID 1550 n-Pentanol partial esters, like the DIACID 1550 2-Ethyl-1-hexanol and 1-Dodecanol partial esters, significantly outperformed DIACID 1550 in the concentrate and the hard water dilution; (2) in the optimized potassium hydroxide based semi-synthetic system, the DIACID 1550 n-Pentanol partial esters, like the 1550 2-Ethyl-1-hexanol and 1-Dodecanol partial esters, significantly outperformed DIACID 1550 in the concentrate and the hard water dilution; (3) in the TEA based synthetic system, the unmodified formulation gave poor results in the hard water dilutions with all the partial esters and DIACID 1550; (4) DIACID 1550 gave very good stability in the TEA based and potassium hydroxide based synthetic formulation concentrate without hard water; (5) the TEA based synthetic system modified with a nonionic surfactant like IGEPAL CO-530, an octylphenol ethoxylate (HLB=10.8), gave very good stability and significant improvement with the partial esters and to a lesser degree with DIACID1550; (6) in the potassium hydroxide based unmodified synthetic formulation, all the partial esters and DIACID 1550 gave poor results in the hard water dilutions; (7) in the potassium hydroxide based synthetic system with the HLB adjusted, the DIACID 1550 partial esters were far superior to DIACID 1550; (8) system adjustments did not improve the DIACID 1550 performance anywhere near as well as the improvement obtained in the performance of the DIACID 1550 partial esters; and (9) adjustment of the system HLB enhanced the stability of the concentrates and the hard water dilutions.

The investigation of the neutralized DIACID 1550 n-Pentanol partial esters as potential lubricating corrosion inhibitors consisted of observation of the salts in 300 ppm hard water, examination of the performance in the Iron Chip Corrosion Test (ASTM D4627-86), and the examination of lubricity properties using the Falex Pin and V-Block Lubricity Testing Apparatus (ASTM D2670). The results were compared to results for the neutralized 2-Ethylhexyl and dodecanol partial esters. The inherent foam properties of the neutralized partial esters were determined with the Ross-Miles Foam Test procedure, as cited above, and compared to the results for the neutralized 2-Ethyl-1-hexanol and 1-Dodecanol DIACID partial esters.

Semi-Synthetic Formulation. The DIACID 1550 n-Pentanol partial esters were formulated into a TEA based, and a KOH based, generic semi-synthetic metalworking fluid, and compared with results for DIACID 1550, DIACID 1550 2-Ethyl-1-hexanol partial ester, and DIACID 1550 1-Dodecanol partial ester. The general formulation is included in Table 8 above and Table 21 below. The concentrates were formulated with deionized and subsequently 1% active concentration dilutions were made with 300 ppm hard water. The concentrates and dilutions were observed for at least 10 days. The clarity, stability, layering, scumming, and relative foam were documented.

TABLE 21

Potassium Hydroxide Based Semi-synthetic Metalworking Fluid Concentrate Formulation

| Component | Weight % |
| --- | --- |
| Golden Bear 100 SUS Oil | 15.0 |
| ACTRAMIDE 202 | 15.0 |
| ACTRABASE 264 | 5.0 |
| DIACID 1550 or partial ester | 6.2 |
| Butyl CARBITOL ™ | 3.9 |
| KOH, 45% | q.s. to pH = 8-10 |
| Water, DI | Q.S. to 100% |

TABLE 22

| | DIACID 1550 2-Ethylhexyl Partial Ester | DIACID 1550 Dodecyl Partial Ester | DIACID 1550 n-Pentyl Partial Ester | DIACID $K^+$ Salt | DIACID M-T67 |
| --- | --- | --- | --- | --- | --- |
| Observations | | | | | |
| TEA Salt (neat) | 1, W | 1, W | 1, W | 1, W | 1, W |
| $K^+$ Salt (41% $H_2O$) | 1, W | 2, Z | 1, W | 1, W | 1, W |
| TEA Salt | | | | | |
| 0.5% (300 ppm HW) | 1, Y | 1, Y, VLS | | | 1, Z, LS |
| 1% (300 ppm HW) | 1, Y | 1, Y | 1, Z | | |
| 2% (300 ppm HW) | 1, X | 1, Y | 1, Z | | |
| 5% (300 ppm HW) | 1, X | 1, Y | 1, Z | | |
| 10% (300 ppm HW) | 1, X | 1, Y | | | 1, W |
| $K^+$ Salt | | | | | |
| 0.5% (300 ppm HW) | 1, X | 1, Y | | 2, Z, LS | |
| 1% (300 ppm HW) | 1, X | 1, Y | 1, Y | | |
| 2% (300 ppm HW) | 1, X | 1, Y | 1, X | | |
| 5% (300 ppm HW) | 1, X | 1, Z | 1, W | | |
| 10% (300 ppm HW) | 1, X | 1, Z | | 1, W | |
| Cast Iron Chip Test | | | | | |
| TEA Salt | | | | | |
| 0.5% (300 ppm HW) | D | D | C | | D |
| 1% (300 ppm HW) | C | D | C | | B |
| 2% (300 ppm HW) | D | D | C | | B |
| 5% (300 ppm HW) | B | C | B | | B+ |
| 10% (300 ppm HW) | B+ | B | B+ | | A |
| $K^+$ Salt | | | | | |
| 0.5% (300 ppm HW) | D | D | D | | D |
| 1% (300 ppm HW) | D | D | C | | C |

TABLE 22-continued

|  | DIACID 1550 2-Ethylhexyl Partial Ester | DIACID 1550 Dodecyl Partial Ester | DIACID 1550 n-Pentyl Partial Ester | DIACID K+ Salt | DIACID M-T67 |
|---|---|---|---|---|---|
| 2% (300 ppm HW) | C | C | C | C |  |
| 5% (300 ppm HW) | A | A | B+ | B |  |
| 10% (300 ppm HW) | A | A | A | A |  |

Key:
1 Stable
2 Unstable after 1 hour
3 Unstable after 1 day
4 Precipitate
VLS Very light scum
LS Light scum
MS Medium scum
HS Heavy scum
W clear
X blue-white haze
Y White haze
Z Opaque
A No rust
B Up to 20% rust spots
C Up to 50% rust spots
D Greater than 50% rust spots The observations of dilute solutions of the DIACID 1550 partial ester salts made with 300 ppm hard water, and the results of the Iron Chip Test are reported in Table 22. The DIACID 1550 n-Pentanol partial ester performs comparably to the DIACID 1550 2-Ethyl-1-hexanol or 1-Dodecanol partial esters and DIACID 1550 with regard to hard water stability and Iron Chip Corrosion Inhibition.

TABLE 23

Falex Pin and V-Block Analysis

| Observations | DIACID 1550 2-Ethylhexyl Partial Ester | DIACID 1550 Dodecyl Partial Ester | DIACID 1550 n-Pentyl Partial Ester | DIACID K+ Salt | DIACID M-T67 |
|---|---|---|---|---|---|
| Lubricity Falex P&V Boundary (700 psi) |  | Number of Teeth (lower is better) |  |  |  |
| TEA Salt 1% (300 ppm HW) | 19 | 17 | 16 |  | 38* |
| K+ Salt 1% (300 ppm HW) | 36 | 38 | 39 | 163* |  |

*Data from the DIACID Metalworking Manual Section on Lubricity.

The Falex Pin and V-Block results are reported in Table 23. The DIACID 1550 n-Pentanol partial ester performs comparably to the DIACID 1550 2-Ethyl-1-hexanol or 1-Dodecanol partial esters. All three of the DIACID 1550 partial esters perform better than DIACID 1550 with regard to Boundary Lubrication as tested by the Falex Pin and V-Block procedure.

TABLE 24

Ross-Miles Foam Test (at 49° C.)

| Sample | Conc., % | Time = 1 min Foam Height, cm | Time = 5 min Foam Height, cm |
|---|---|---|---|
| DIACID 1550 K+ Salt (full) | 0.1 | 10.0 | 9.5 |
| DIACID 1550 Partial Ester of 2-Ethyl-1-hexanol, K+ Salt | 0.1 | 4.5 | 1.5 |
| DIACID 1550 Partial Ester of 1-Dodecanol, K+ Salt | 0.1 | 6.5 | 2.5 |
| DIACID 1550 Partial Ester of n-Pentanol, K+ Salt | 0.1 | 10.5 | 1.0 |
| DIACID 1550 TEA Salt (full) | 0.1 | 2.5 | 1.5 |
| DIACID 1550 Partial Ester of 2-Ethyl-1-hexanol, K+ Salt | 0.1 | 1.5 | 0.5 |
| DIACID 1550 Partial Ester of 1-Dodecanol, K+ Salt | 0.1 | 1.5 | 0.5 |
| DIACID 1550 Partial Ester of n-Pentanol, K+ Salt | 0.1 | 1.0 | 0.5 |
| DIACID 1550 K+ Salt (full) | 1.0 | 20.5 | 19.5 |
| DIACID 1550 Partial Ester of 2-Ethyl-1-hexanol, K+ Salt | 1.0 | 10.5 | 0.5 |
| DIACID 1550 Partial Ester of 1-Dodecanol, K+ Salt | 1.0 | 12.5 | 1.0 |
| DIACID 1550 Partial Ester of n-Pentanol, K+ Salt | 1.0 | 13.5 | 1.5 |
| DIACID 1550 TEA Salt (full) | 1.0 | 18.5 | 5.0 |
| DIACID 1550 Partial Ester of 2-Ethyl-1-hexanol, K+ Salt | 1.0 | 4.0 | 0.5 |

TABLE 24-continued

Ross-Miles Foam Test (at 49° C.)

| Sample | Conc., % | Time = 1 min Foam Height, cm | Time = 5 min Foam Height, cm |
|---|---|---|---|
| DIACID 1550 Partial Ester of 1-Dodecanol, K+ Salt | 1.0 | 2.5 | 0.5 |
| DIACID 1550 Partial Ester of n-Pentanol, K+ Salt | 1.0 | 5.0 | 0.5 |

The Ross-Miles Foam results are reported in Table 24. The DIACID 1550 n-Pentanol partial ester performs comparably to the DIACID 1550 2-Ethyl-1-hexanol or 1-Dodecanol partial esters, except that the 0.1% solution of potassium neutralized n-Pentanol partial ester appears to have initial foam heights like DIACID 1550 potassium neutralized material. However, the potassium neutralized n-Pentanol partial ester solution has a 5 minute foam stability like the other partial esters. In general, the partial esters have are improved with regard to their foaming properties (i.e., they have reduced foam production).

TABLE 25

Semi-Synthetic Metalworking Formulation with TEA

| | 81A | 81B | 7833-62A | 7833-62B | 7833-62C |
|---|---|---|---|---|---|
| Component | | | | | |
| Golden Bear 100 | 15.04 | 15.02 | 15.13 | 15.07 | 14.93 |
| ACTRAMIDE 202 | 15.15 | 15.06 | 15.03 | 15.12 | 15.11 |
| ACTRABASE 264 | 5.08 | 5.05 | 5.18 | 5.06 | 5.02 |
| DIACID 1550 | | | 6.44 | | |
| DIACID1550 2-Ethyl-1-hexanol Partial Ester | | | | 6.17 | |
| DIACID1550 dodecanol Partial Ester | | | | | 6.40 |
| DIACID1550 n-Pentanol Partial ester | 6.02 | 6.13 | | | |
| TEA, 99% | 6.88 | 6.91 | 9.76 | 6.96 | 6.85 |
| DI Water | 51.82 | 47.82 | 44.40 | 47.61 | 47.67 |
| Butyl CARBITOL ™ | | 4.02 | 4.05 | 4.00 | 4.02 |
| Appearance | | | | | |
| Concentrate | | | | | |
| Initial | 2, 4 | 1, 2 | 6 | 1, 2 | 1, 2 |
| 1 Hour | | | 7 | | |
| 1 Day | 5, 5 | 1, 2 | 7 | 1, 2 | 1, 2 |
| 2 Day | 5, 2 | 1, 2 | | 1, 2 | 1, 2 |
| 5 Day | 5, 2 | 1, 2 | | | |
| 6 Day | 6 | 1, 2 | | 1, 2 | 1, 2 |
| 15 Day | 6 | 1, 2 | | 1, 2 | 1, 2 |
| 1% in 300 ppm HW | | | | | |
| Initial | 2, 6, C | 2, 3, C | 6, B | 3, 2, C | 3, 2, C/D |
| 1 Hour | | | 6, 0 | | |
| 1 Day | 2, 6 | 2, 4 | 6, 0 | 4, 2 | 4, 2 |
| 2 Day | 2, 6 | 2, 5 | 6, 0 | 4, 2 | 4, 2 |
| 5 Day | 2, 6 | 2, 5 | | | |
| 6 Day | 6, 8 | 2, 5 | 6, 0 | 4, 2 | 4, 2 |
| 15 Day | 6, 0 | 2, 5 | 6, 0 | 5, 9/0 | 5, 0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Results for the TEA based semi-synthetic metalworking fluid formulation are shown in Table 25. As shown previously above, DIACID 1550 performs poorly in the concentrate and the hard water dilution. The DIACID 1550 2-Ethyl-1-hexanol and 1-Dodecanol partial esters performed very well in the concentrate and good in the hard water dilutions when the system was stabilized with a coupling solvent.

TABLE 26

Semi-Synthetic Metalworking Formulation with Potassium Hydroxide

| Component | 81C | 81D | 7833-54E | 7833-55E | 7833-55G | 7833-57A | 7833-57C | 7833-57E |
|---|---|---|---|---|---|---|---|---|
| Golden Bear 100 | 15.04 | 15.04 | 14.72 | 15.06 | 14.43 | 14.81 | 15.10 | 14.89 |
| ACTRAMIDE 202 | 15.10 | 15.22 | 14.68 | 15.02 | 14.39 | 14.87 | 15.06 | 14.96 |
| ACTRABASE 264 | 5.10 | 5.17 | 4.87 | 5.09 | 4.88 | 5.20 | 5.12 | 5.02 |
| DIACID 1550 | | | | 6.04 | 5.79 | | | 6.08 |
| DIACID1550 2-Ethyl-1-hexanol Partial Ester | | | 5.93 | | | | 6.09 | |
| DIACID1550 dodecanol Partial Ester | | | | | | 6.17 | | |
| DIACID1550 n-Pentanol Partial Ester | 6.20 | 6.04 | | | | | | |
| DOWANOL ™ TPM | | 4.01 | 3.82 | 1.61 | 5.73 | | | |
| DI Water | 56.50 | 52.47 | 54.06 | 52.67 | 50.47 | 52.82 | 52.51 | 50.48 |
| KOH, 45% | 2.07 | 2.05 | 1.92 | 4.50 | 4.31 | 2.27 | 2.20 | 4.61 |
| Butyl CARBITOL ™ | | | | | | 3.85 | 3.93 | 3.87 |
| Appearance | | | | | | | | |
| Concentrate | | | | | | | | |
| Initial | 5, 2 | 1, 2 | 1, 2 | 6, D | 6, D | 1, 2 | 1, 2 | 6 |
| 1 Day | 5, 2 | 1, 2 | | | | | | |
| 2 Day | 5, 2 | 1, 2 | | | | | | |

TABLE 26-continued

Semi-Synthetic Metalworking Formulation with Potassium Hydroxide

| Component | 81C | 81D | 7833-54E | 7833-55E | 7833-55G | 7833-57A | 7833-57C | 7833-57E |
|---|---|---|---|---|---|---|---|---|
| 5 Day | 5, 2 | 1, 2 | | | | 1, 2 | 1, 2 | |
| 6 Day | 6 | 1, 2 | 2, 3 | | | | | |
| 15 Day | 6 | 1, 2 | 2, 3 | | | 1, 2 | 1, 2 | |
| 1% in 300 ppm HW | | | | | | | | |
| Initial | 2, 6, B/C | 2, 3, C | 2, 3 | 6, C | 6, C | 2, 3, B/C | 2, 3, B/C | 6, B/C |
| 1 Hour | | | | | | | | 2, 6, 8 |
| 1 Day | 2, 6 | 2, 4 | | | | | | |
| 4 Day | 6, 8 | 2, 4 | | | | | | |
| 5 Day | 6, 8 | 4, X | | | | 2, 4, 9 | 2, 4, 8 | 6, 0 |
| 6 Day | 6, 8 | 4, X | 2, 3 | 6, 7, 0 | 6, 7, 0 | | | |
| 15 Day | 6, 8 | 4, X | 2, 3 | | | | | |

Apperance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Results for the potassium hydroxide based semi-synthetic metalworking fluid formulation can be found in Table 26. Once again as reported previously above, DIACID 1550 performs poorly in the concentrate and the hard water dilution, whether or not the system has been stabilized with a coupling solvent. The DIACID 1550 2-Ethyl-1-hexanol, 1-Dodecanol, and n-Pentanol partial esters performed very well in the concentrate and good in the hard water dilutions when the system was stabilized with a coupling solvent.

In both the TEA and the potassium hydroxide based systems, the DIACID 1550 partial ester performed better than DIACID 1550 even when the system does not contain a coupling solvent.

Synthetic Formulation. The DIACID 1550 n-Pentanol partial esters were formulated into a TEA based, and a KOH based, generic synthetic metalworking fluid, and compared to DIACID 1550, DIACID 1550 2-Ethyl-1-hexanol partial ester, and DIACID 1550 1-Dodecanol partial ester. The general formulation is included in Tables 10 and 15 above. The concentrates were formulated with deionized water, and subsequently 1% active concentration dilutions were made with 300 ppm hard water. The concentrates and dilutions were observed for at least 10 days. The clarity, stability, layering, scumming, and relative foam were documented.

TABLE 27

Synthetic Metalworking Formulation with TEA.

| Component | 80D | 63C | 63B | 63A | 80E | 67B |
|---|---|---|---|---|---|---|
| DI Water | 70.09 | 70.46 | 70.27 | 66.61 | 64.89 | 65.06 |
| TEA, 99% | 7.32 | 7.08 | 7.33 | 10.84 | 7.39 | 7.30 |
| DIACID 1550 | | | | 8.11 | | |
| DIACID1550 2-Ethyl-1-hexanol Partial Ester | | | 8.14 | | | 8.18 |
| DIACID1550 1-Dodecanol Partial Ester | | 8.13 | | | | |
| DIACID 1550 n-Pentanol Partial Ester | 8.20 | | | | 8.16 | |
| EM-550 | 10.21 | 10.15 | 10.10 | 10.26 | 10.35 | 10.17 |
| EMPHOS TS-230 | 4.18 | 4.18 | 4.15 | 4.17 | 4.19 | 4.14 |
| IGEPAL CO-530 | | | | | 5.02 | 5.15 |

TABLE 27-continued

Synthetic Metalworking Formulation with TEA.

| Component | 80D | 63C | 63B | 63A | 80E | 67B |
|---|---|---|---|---|---|---|
| Appearance | | | | | | |
| Concentrate | | | | | | |
| Initial | 2, 6, C | 6, B | 6, B | 1, 2, D+ | 1, 2, C | 1, 2 |
| 1 Hour | | 7 | 7 | 1, 2 | | |
| 1 Day | 7 | 7 | 7 | 1, 2 | 1, 2 | 1, 2 |
| 2 Day | | | | | 1, 2 | |
| 3 Day | | | | | 1, 2 | 1, 2 |
| 5 Day | | | | | 1, 2 | |
| 6 Day | | | | | 1, 2 | 1, 2 |
| 15 Day | | 7 | 7 | 1, 2 | 1, 2 | 1, 2 |
| 1% in 300 ppm HW | | | | | | |
| Initial | 2, 5, C/D | 5, C | 5, B | 3, C/D | 1, 2, D | 1, 2, C/D |
| 1 Hour | | 5, 9 | 5, 9 | 3, 8 | | |
| 2 Hours | 7, 0 | | | | 3, 2 | |
| 1 Day | | 6, 0 | 6, 0 | 3, 9 | 3, 2 | 4, 2 |
| 2 Day | | | | | 3, 2 | |
| 4 Day | | | | | | 4, 2 |
| 5 Day | | | | | 4, 2 | |
| 6 Day | | | | | 4, 2 | 4, 2 |
| 15 Day | | 6, 0 | 6, 0 | 5, 9 | 4, 2 | 4, 2 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top

TABLE 28

Synthetic Metalworking Formulation with TEA

| Component | 65A | 66A |
|---|---|---|
| DI Water | 63.61 | 63.67 |
| TEA, 99% | 10.85 | 10.85 |
| DIACID 1550 | 8.15 | 8.13 |
| EM-550 | 10.13 | 10.16 |
| EMPHOS TS-230 | 4.18 | 4.13 |
| Ethox TMO14A | 3.07 | |
| Tergitol NP-9 | | 3.06 |
| Appearance | | |
| Concentrate | | |
| Initial | 1, 2, D | 1, 2, D |
| 1 Day | 1, 2 | 1, 2 |
| 4 Day | 1, 2 | 1, 2 |
| 6 Day | 1, 2 | 1, 2 |
| 15 Day | 1, 2 | 1, 2 |
| 1% in 300 ppm HW | | |
| Initial | 1, 2, D+ | 1, 2, D |
| 1 Hour | 3, 9 | |
| 1 Day | 3, 9 | 1, 2 |
| 4 Day | 4, 9/0 | 4, 8 |
| 6 Day | 5, 9/0 | 5, 8 |
| 15 Day | 5, 9/0 | 5, 8 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Results for the TEA based synthetic metalworking fluid formulations can be found in Tables 27 and 28. Items 63A, 63B, 63C, and 80D are the results for DIACID 1550, the DIACID 1550 2-Ethyl-1-hexanol partial ester, the DIACID 1550 1-Dodecanol partial ester, and the DIACID 1550 n-Pentanol partial ester, respectively. In the unmodified formulation, DIACID 1550 performed well in the concentrate, but poorly in the hard water dilution. In the unmodified formulation, the DIACID 1550 2-Ethyl-1-hexanol, 1-Dodecanol, and n-Pentanol partial esters performed very poorly in the concentrate and the hard water dilutions. When the formulation is modified with nonionic surfactants to balance the HLB, the DIACID 1550 performs better in the hard water dilution. The DIACID 1550 partial esters perform significantly better in both the concentrate and the hard water dilutions when the formulation is modified with nonionic surfactants to balance the HLB

TABLE 29

Synthetic Metalworking Formulation with Potassium Hydroxide.

| Component | 80A | 71C | 71B | 71A | 80B | 80C | 75E | 75D |
|---|---|---|---|---|---|---|---|---|
| DI Water | 73.49 | 73.38 | 73.41 | 67.52 | 70.25 | 69.93 | 70.29 | 70.15 |
| KOH, 45% | 3.86 | 3.62 | 3.96 | 9.76 | 3.88 | 3.92 | 3.85 | 3.85 |
| DIACID M-T67 | | | | | | | | |
| DIACID 1550 | | | | 8.06 | | | | |
| DIACID1550 2-Ethyl-1-hexanol Partial Ester | | | 8.14 | | | | 8.12 | 8.15 |
| DIACID1550 1-Dodecanol Partial Ester | | 8.11 | | | | | | |
| DIACID 1550 n-Pentanol Partial Ester | 8.24 | | | | 8.15 | 5.23 | | |
| EM-550 | 10.27 | 10.54 | 10.26 | 10.46 | 10.15 | 10.18 | 10.11 | 10.18 |
| EMPHOS TS-230 | 4.14 | 4.35 | 4.23 | 4.20 | 4.13 | 4.31 | 4.13 | 4.17 |
| Tergitol NP-7 | | | | | | 3.44 | | 3.49 |
| OCD-383 | | | | | 3.44 | | 3.51 | |
| Appearance | | | | | | | | |
| Concentrate | | | | | | | | |
| Initial | 2, 5, C | 4, 2, C | 4, 2, C | 1, 2, D | 1, 2, C | 1, 2, C/D | 1, 2, C | 1, 2, D |
| 1 Hour | | 5, 2 | 5, 2 | | | | | |
| 1 Day | 1 | 7 | 7 | 1, 2 | 1, 2 | 1, 2 | 1, 2 | 1, 2 |
| 2 Day | | | | | 1, 2 | 1, 2 | | |
| 3 Day | | | | 1, 2 | 1, 2 | 1, 2 | | |
| 5 Day | | | | | 1, 2 | 1, 2 | 1, 2 | 1, 2 |
| 6 Day | | | | 1, 2 | 1, 2 | 1, 2 | 1, 2 | 1, 2 |
| 15 Day | | | | 1, 2 | 1, 2 | 1, 2 | 1, 2 | 1, 2 |
| 1% in 300 ppm HW | | | | | | | | |
| Initial | 2, 4, C | 4, 2, A | 4, 2, A | 3, D, 8 | 1, 2, B/C | 1, 2, C/D | 1, 2, B+ | 1, 2, C |
| 1 Hour | | 4, 2 | 4, 2 | 3, 9 | | | | |
| 2 Hours | 4, X | | | | 1, 2 | 1, 2 | | |
| 1 Day | 4, X | 4, 0 | 5, 0 | 3, 0 | 1, 2 | 1, 2 | 1, 2 | 1, 2 |
| 2 Day | 4, 9 | 4, 0 | 5, 0 | 4, 0 | 1, 2 | 1, 2 | | |
| 3 Day | | 4, 0 | 5, 0 | 4, 0 | | | | |
| 5 Day | 4, 0 | | | | 1, 2 | 1, 2 | | |
| 6 Day | | 4, 0 | 5, 0 | 4, 0 | 1, 2 | 1, 2 | 1, 2 | 1, 2 |
| 15 Day | | 4, 0 | 5, 0 | 4, 0 | 1, 2 | 1, 2 | 1, 2 | 1, 2 |

Appearance Key:

1 = clear

2 = stable

3 = very light haze

4 = light haze

5 = haze

6 = opaque, milky

7 = layers

8 = very light scum

9 = light scum

0 = scum, creamy

A = light foam

B = low foam

C = medium foam

D = high foam

X = oil droplets at the top

TABLE 30

Synthetic Metalworking Formulation with Potassium Hydroxide

| Component | 72C | 72B | 72A | 71C | 71B | 71A |
|---|---|---|---|---|---|---|
| DI Water | 70.57 | 69.54 | 64.29 | 73.38 | 73.41 | 67.52 |
| KOH, 45% | 3.47 | 3.83 | 9.74 | 3.62 | 3.96 | 9.76 |
| DIACID 1550 |  |  | 8.19 |  |  | 8.06 |
| DIACID1550 2-Ethyl-1-hexanol Partial Ester |  | 8.52 |  |  | 8.14 |  |
| DIACID1550 1-Dodecanol Partial Ester | 8.39 |  |  | 8.11 |  |  |
| EM-550 | 10.06 | 10.42 | 10.13 | 10.54 | 10.26 | 10.46 |
| EMPHOS TS-230 | 4.07 | 4.18 | 4.18 | 4.35 | 4.23 | 4.20 |
| Ethox TMO14A | 3.43 | 3.52 | 3.47 |  |  |  |

Appearance

Concentrate

| | 72C | 72B | 72A | 71C | 71B | 71A |
|---|---|---|---|---|---|---|
| Initial | 1, 2, C | 1, 2, C | 1, 2, D | 4, 2, C | 4, 2, C | 1, 2, D |
| 1 Hour |  |  |  | 5, 2 | 5, 2 |  |
| 1 Day | 1, 2 | 1, 2 | 1, 2 | 7.00 | 7.00 | 1, 2 |
| 2 Day | 1, 2 | 1, 2 | 1, 2 |  |  |  |
| 3 Day | 4, 2 | 1, 2 | 1, 2 |  |  | 1, 2 |
| 6 Day | 7, X | 1, 2 | 1, 2 |  |  | 1, 2 |
| 15 Day |  | 1, 2 | 1, 2 |  |  | 1, 2 |

1% in 300 ppm HW

| | 72C | 72B | 72A | 71C | 71B | 71A |
|---|---|---|---|---|---|---|
| Initial | 1, 2, B/C | 1, 2, B/C | 4, D, 8 | 4, 2, A | 4, 2, A | 3, D, 8 |
| 1 Hour |  |  |  | 4, 2 | 4, 2 | 3, 9 |
| 1 Day | 1, 2 | 1, 2 | 3, 0 | 4, 0 | 5, 0 | 3, 0 |
| 2 Day | 1, 2 | 1, 2 | 4, 0 | 4, 0 | 5, 0 | 4, 0 |
| 3 Day | 1, 2 | 1, 2 | 4, 0 | 4, 0 | 5, 0 | 4, 0 |
| 6 Day | 1, 2 | 1, 2 | 4, 0 | 4, 0 | 5, 0 | 4, 0 |
| 15 Day | 1, 2 | 1, 2 | 4, 0 | 4, 0 | 5, 0 | 4, 0 |

Appearance Key:
1 = clear
2 = stable
3 = very light haze
4 = light haze
5 = haze
6 = opaque, milky
7 = layers
8 = very light scum
9 = light scum
0 = scum, creamy
A = light foam
B = low foam
C = medium foam
D = high foam
X = oil droplets at the top Results for the potassium hydroxide based synthetic formulation can be found in Tables 29 and 30. They represent the examination of the partial esters in the potassium hydroxide based synthetic formulation unmodified and modified with HLB adjusting additives of three chemistries. The nonionic HLB adjusting additives were a nonylphenol 7 mole ethoxylate (TERGITOL NP-7), a Ingevity DIACID 1550 12 mole ethoxylate (OCD-383), and a tall oil fatty acid 14 mole ethoxylate (Ethox TMO14A). It should be noted here that the Ingevity DIACID 1550 ethoxylate with 12 moles EO (OCD-383) was one of the best performers in studies above and its formulation had the lowest foam.

DIACID 1550 partial esters of n-Pentanol, 2-Ethyl-1-hexanol, and 1-Dodecanol have properties that can be used in semi-semisynthetic and synthetic metalworking fluid formulations. In properly balanced systems, they provide very good results with regard to emulsion stability in hard water. This hard water stability is a significant improvement over DIACID 1550. The DIACID 1550 partial esters have enhanced lubrication and comparable corrosion inhibition properties to DIACID 1550. The partial esters give very good results in synthetic systems when nonionic surfactants are used to adjust the HLB of the formulation. In semi-synthetic systems, a coupling solvent can be used to optimize formulation stability. The partial esters appear to have significantly better flexibility when compared to DIACID 1550 in semi-synthetic formulations. These experiments demonstrate that DIACID 1550 partial esters of alcohols can be used as products for metalworking.

Comparison of the Lubricity and Hydrolytic Stability of DIACID 1550 2-Ethyl-1-hexanol Partial Ester and TOFA Ester Lubricant. DIACID 1550 2-Ethyl-1-hexanol partial ester was analyzed for lubricity, and compared to an identical formula containing an industry standard TOFA Ester Lubricant (Polartech LA 8330). The DIACID 1550 2-Ethyl-1-hexanol partial ester was further tested for hydrolytic stability, and that data was measured against a standard ester used for comparison testing. The DIACID 1550 2-Ethylhexanol formulation utilized is shown in Table 31.

TABLE 31

DIACID 1550 2-Ethylhexanol Formulation Utilized in the 4Ball Test

| Ingredient | % by Vol |
|---|---|
| Water | 57.6 (note: STL Tap ~120 ppm) |
| Amine Borate | 8 |
| Carboxylic Acid | 12 |
| Amino Alcohol | 5 |
| Test Ester | 5 |
| Neodecanoic Acid | 5 |
| Propylene Glycol | 3 |
| Passivators, Inhibitors, dye | 4.4 |
| Total | 100 |

Wear scar diameter was measure using a 4Ball instrument. The instrument was set to ramp from 0 Kg to 200 Kg of pressure over the course of 20 minutes with the apparatus revolving at a constant 600 rpms. While the pressure ramped, fluid temperature, torque, wear, and coefficient of friction were tracked. The data are graphed, and can be compared between tests. The data point that is of the most importance is the measured scar diameter at the end of the test, measured in millimeters. Other data points that bear attention are in the column "Value at Cursor," which indicate the maximum value of each parameter at 200 Kg of pressure after 20 minutes. These data points have been collated into the Table 32.

TABLE 32

4Ball Test Data for Ester Lubricants
4Ball Test Data for Ester Lubricants
(20 minute ramp to 200 Kg @ 600 rpm)

| | DIACID 1550 2-Ethylhexanol Partial Ester | LA-8330 | EL Ester |
|---|---|---|---|
| Scar diameter (mm) | 0.89 | 0.95 | 1.05 |
| Torque (kgf * m) | 0.0756 | 0.0976 | 0.0921 |
| Coefficient of Friction | 0.08 | 0.11 | 0.1 |
| Fluid Temp (F.) | 127 | 157 | 150 |

Figure 2:
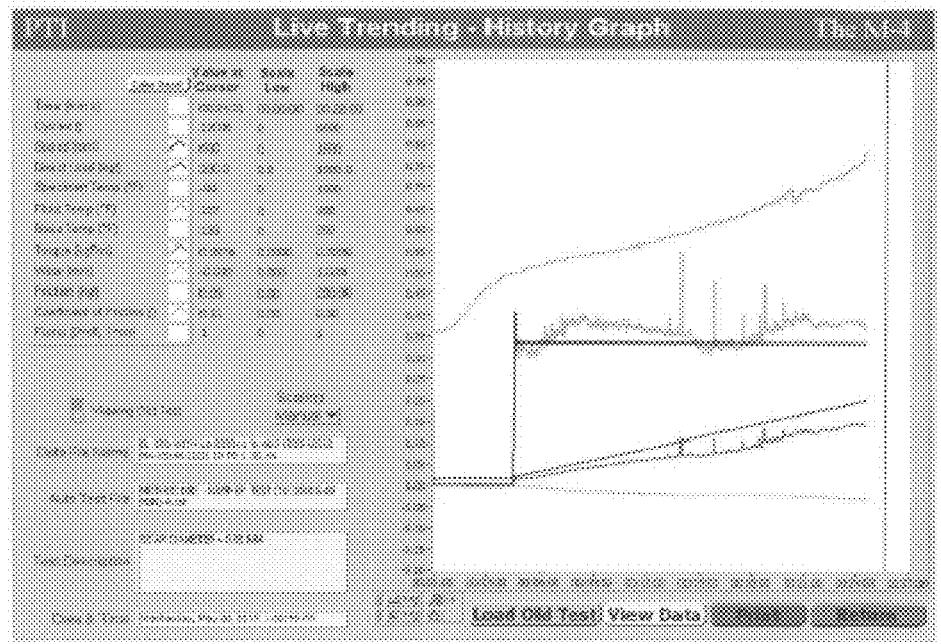
FIG. 2. Graph of Polartech LA-8330 (industry standard lubricant) 4Ball Test data.
Figure 3:
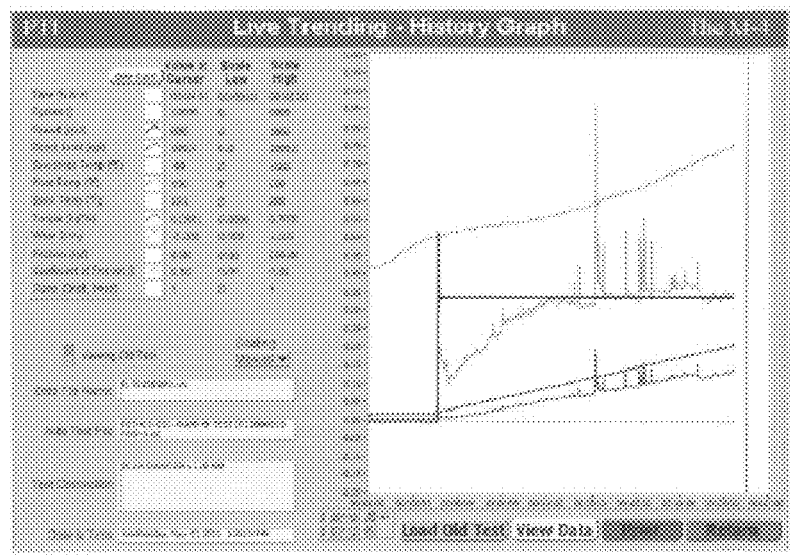
FIG. 3. Graph of a Standard Ester 4Ball Test data.
Figure 4:
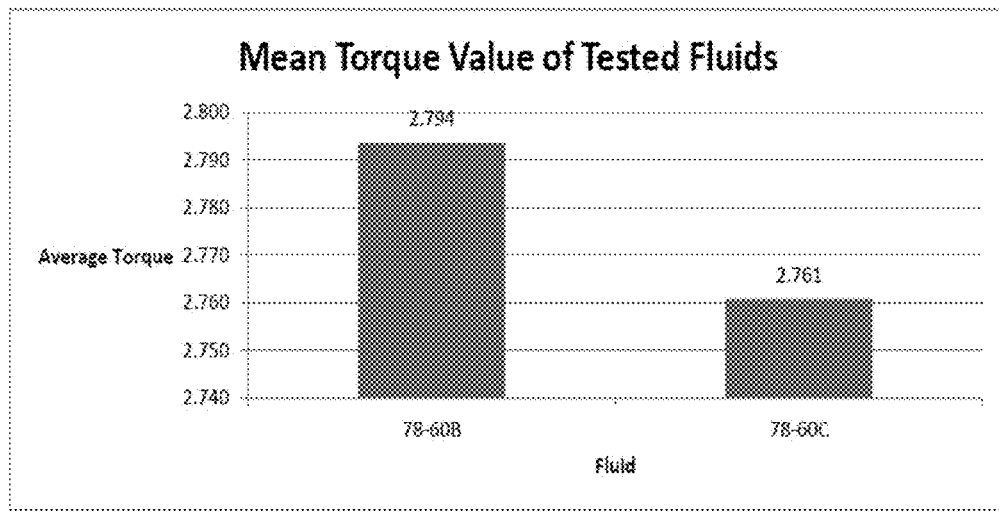
FIG. 4. Graph comparing average torque values from a Microtap in aluminum 6061 of DIACID 1550 2-Ethyl-1-hexanol (78-60B) and an Industry Standard Lubricant (78-60C).
Figure 5:
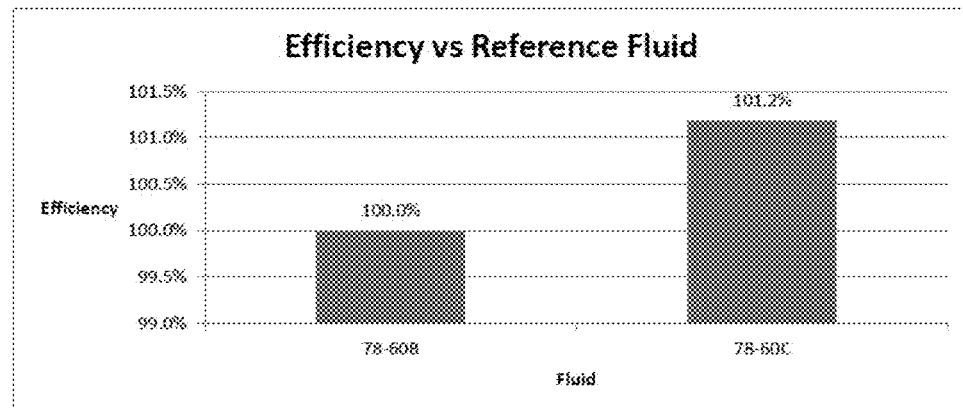
FIG. 5. Graph comparing efficiency of DIACID 1550 2-Ethyl-1-hexanol (78-60B) and an Industry Standard Lubricant (78-60C) in a Microtap test of on aluminum 6061.
Figure 6:
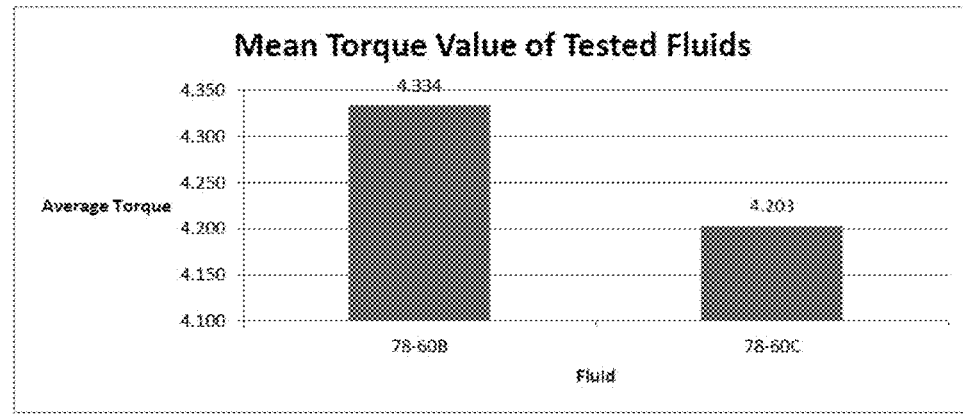
FIG. 6. Graph comparing average torque values from a Microtap in steel 6061 of DIACID 1550 2-Ethyl-1-hexanol (78-60B) and an Industry Standard Lubricant (78-60C).
Figure 7:
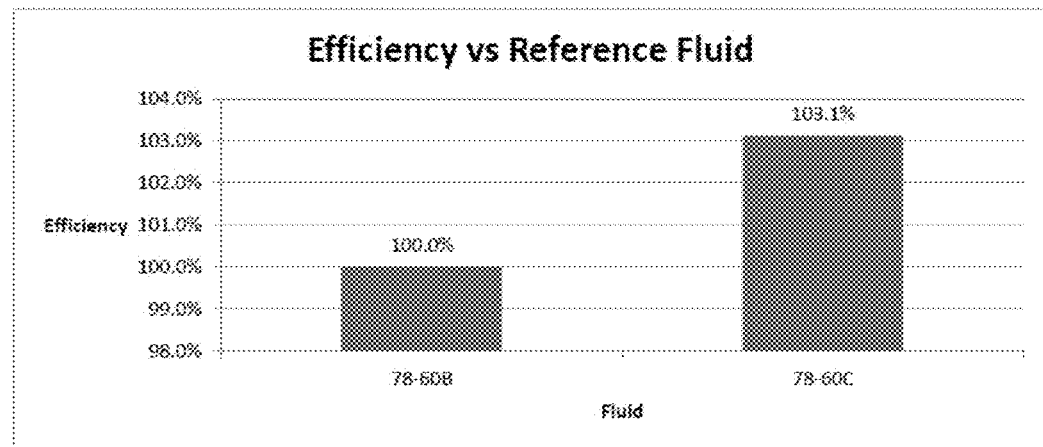
FIG. 7. Graph comparing efficiency of DIACID 1550 2-Ethyl-1-hexanol (78-60B) and an Industry Standard Lubricant (78-60C) in a Microtap test of on steel 1018.

The data of Table 32 indicate that DIACID 1550 2-Ethyl-1-hexanol partial ester is an excellent lubricant compared to the Standard TOFA Ester Lubricant (Polartech LA 8330) and the Standard Ester (EL Ester). FIGS. 1-3 are graphs of the 4Ball Test Data for DIACID 1550 2-Ethyl-1-hexanol partial ester, the Standard TOFA Ester Lubricant (Polartech LA 8330), and the Standard Ester (EL Ester), respectively.

Large esters often have low hydrolytic stability, so this parameter was tested on the DIACID 1550 2-Ethyl-1-hexanol partial ester in comparison with a standard methyl ester used for an ester benchmark. The test method was as follows:
1. Add 2000 ppm of deionized water to test ester.
2. An aliquot of the water/ester mix was sealed in 5 different sealed vials.
3. One vial was retained to test acid value before heating.
4. The vials were placed in a 180° C. oven.
5. Periodically, a vial was removed, allowed to cool, and then the Acid Value was run and the number of days in the over was recorded.
6. Over the course of two weeks all vials were tested. The 5$^{th}$ vial was tested on day 14.

An increase in the acid value indicates hydrolysis is occurring. Less increase in acid value indicates better hydrolytic stability. The data for the hydrolytic stability is shown in Table 33.

TABLE 33

Hydrolytic Stability Test for Ester Lubricants
Hydrolytic Stability Test for Ester Lubricants
(14 days in water in sealed vial at 180° C.)

| | Sample | |
|---|---|---|
| | DIACID 1550 2-Ethylhexanol Partial Ester | Methyl Ester Standard |
| Starting Acid Number | 99.12 | 0.27 |
| Final Acid Number | 110.32 | 5.44 |

The data indicates that DIACID 1550 2-ethylhexyl partial ester is relatively hydrolytically stable. Paired with the lubrication data, this information indicates that DIACID 1550 2-ethylhexyl partial ester is a very effective ester boundary lubricant for metalworking fluids.

Comparison of Lubricity Between Semi-Synthetic Metalworking Fluid with DIACID 1550 2-Ethylhexyl Partial Ester and a Lubricant Used in the Industry. DIACID 1550 2-Ethylhexyl Half Ester containing Semi-synthetic Metalworking Fluid (78-60B) and an Industry Standard Lubricant containing Semi-synthetic Metalworking Fluid (78-60C) were examined via a microtap testing and Falex pin and vee block, shake foam test, cast iron chip test, hard water stability, and emulsion stability.

Microtap testing involved a test bar of the desired alloy with pre-drilled holes through it. These holes were filled with metalworking fluid diluted to 10% in deionized water, then a tapping bit was driven into each hole. The instrument rotated the tapping bit at 500 rpm, and had a torque gauge attached. Four holes were tapped with each fluid, and the mean value of the torque was reported as the work performed by the tapping tool. Lubrication of the formulas was evaluated with 1018 Steel and 6061 Aluminum. The results are shown in Tables 34 and 35 and FIGS. 4-7. With the fluid being the only variable, the lowest mean value determines the best fluid. The mean value is the average torque over the depth of cut.

TABLE 34

Microtap Results on Aluminum
Fluid Comparison at Plateau .2 to 14 mm of 14.5 mm depth of cut

| | Fluid Results | | | Calculated Efficiency vs. | | |
|---|---|---|---|---|---|---|
| Comment | Fluid | Mean Average | Std Dev | Reference Fluid | Best Fluid | All Fluids |
| 10% | 78-60B | 2.794 | 0.822 | 100.0% | 98.8% | 99.4% |
| 10% | 78-60C | 2.761 | 0.872 | 101.2% | 100.0% | 100.6% |

** The Reference Fluid is >>> 78-60B

TABLE 35

Microtap Results on Steel 1018
Fluid Comparison at Plateau .2 to 13.7 mm of 14.0 mm depth of cut

| | Fluid Results | | | Calculated Efficiency vs. | | |
|---|---|---|---|---|---|---|
| Comment | Fluid | Mean Average | Std Dev | Reference Fluid | Best Fluid | All Fluids |
| 10% | 78-60B | 4.334 | 1.329 | 100.0% | 97.0% | 98.5% |
| 10% | 78-60C | 4.203 | 1.307 | 103.1% | 100.0% | 101.6% |

** The Reference Fluid is >>> 78-60B

Figure 8:
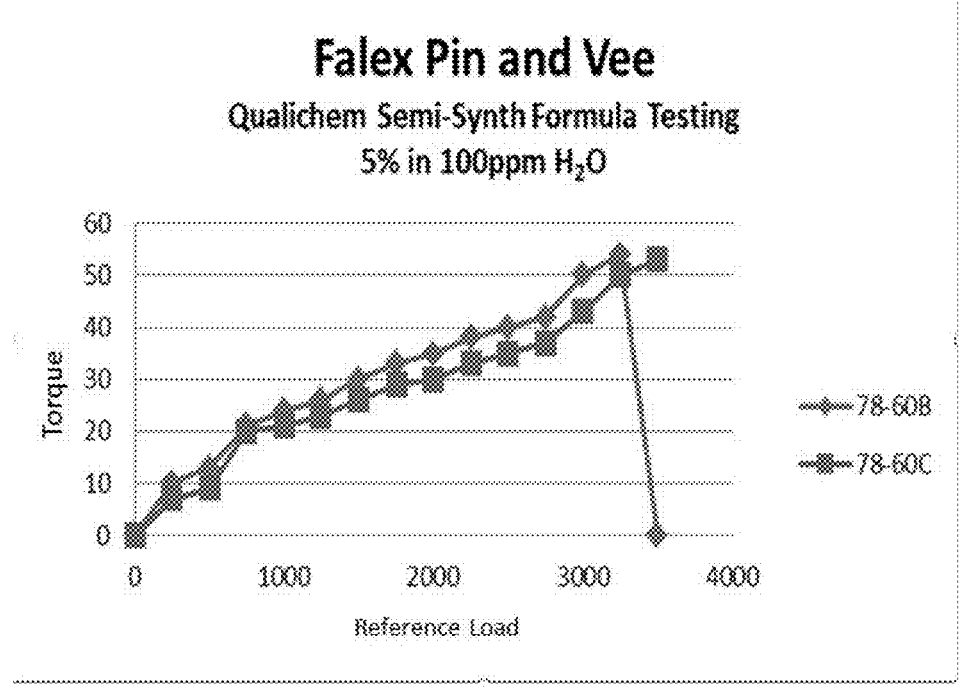
FIG. 8. Graph comparing Falex Pin and Vee results of DIACID 1550 2-Ethyl-1-hexanol (78-60B) and an Industry Standard Lubricant (78-60C).

Falex testing evaluates the lubrication of a metalworking formula. The test was run using steel or aluminum pin and vees. The test was run with steel pin and vee blocks at 5% dilution of the formulas in 100 ppm hardness water. A return to zero torque signifies a failure. As can be seen in FIG. 8, the Industry Standard Lubricant Semi-synthetic Metalworking Fluid (78-60C) failed the test, while DIACID 1550 2-Ethylhexyl Partial Ester Semi-synthetic Metalworking Fluid (78-60B) did not.

The shake foam test evaluates the foaminess of a metalworking fluid by placing 50 mL of a 5% solution in deionized water into a 100 mL stoppered graduated cylinder. The cylinder is then shaken vigorously for 10 seconds. The foam height at t=0 is measured, as is the time for the foam to dissipate to 0 mL. The data from the shake foam test is shown in Table 36.

TABLE 36

Shake Foam Test Data
Shake Foam Test Deionized Water

| | Sample | |
|---|---|---|
| | 78-60B | 78-60C |
| Foam height | 80 mL | 80 mL |
| Time to dissipate | 10 s | 14 s |

Figure 9:
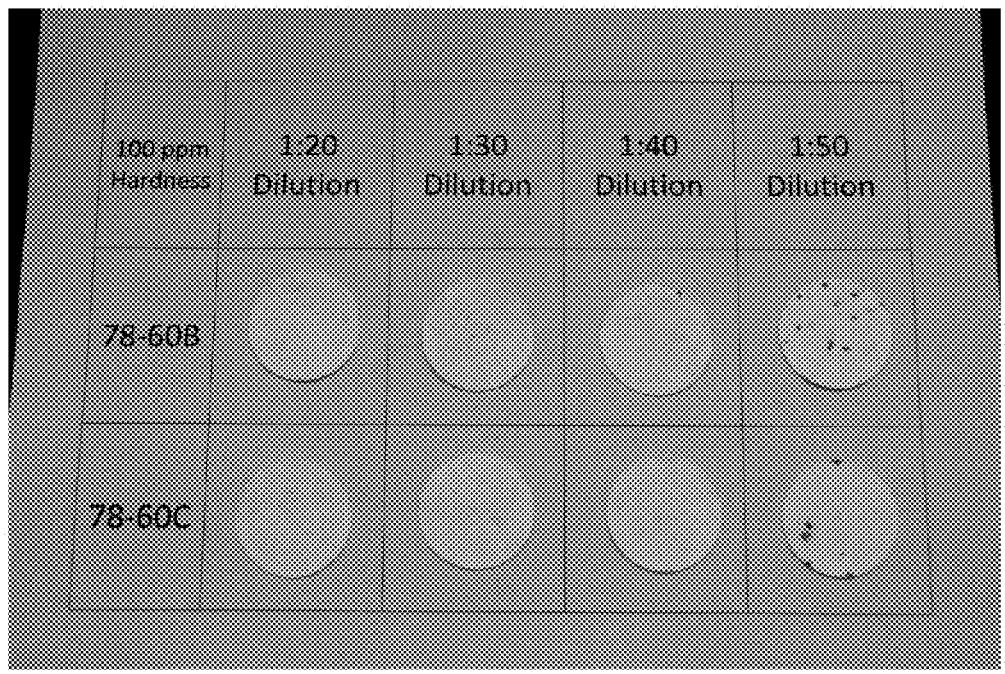
FIG. 9. Corrosion inhibition data for DIACID 1550 2-Ethyl-1-hexanol (78-60B) and an Industry Standard Lubricant (78-60C) in 100 ppm hard water.
Figure 10:
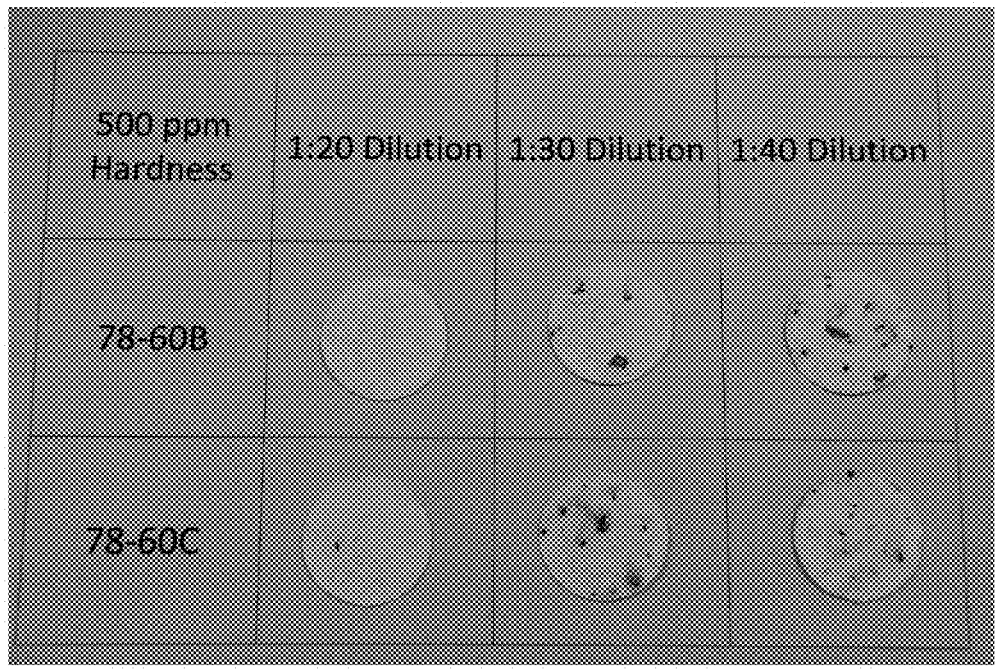
FIG. 10. Corrosion inhibition data for DIACID 1550 2-Ethyl-1-hexanol (78-60B) and an Industry Standard Lubricant (78-60C) in 500 ppm hard water.

Next, the samples were tested using the cast iron chip corrosion test. Any appearance of rust indicates a failure of the fluid to prevent corrosion. Images of the test paper are shown in FIGS. 9 and 10. The test was run at 100 ppm hardness and 500 ppm hardness water at varying dilutions of the formulas. In both tests, the DIACID 1550 2-Ethylhexyl Partial Ester Semi-synthetic Metalworking Fluid (78-60B) and the Industry Standard Lubricant Semi-synthetic Metalworking Fluid (78-60C) have comparable performance for cast iron corrosion inhibition.

Figure 11:
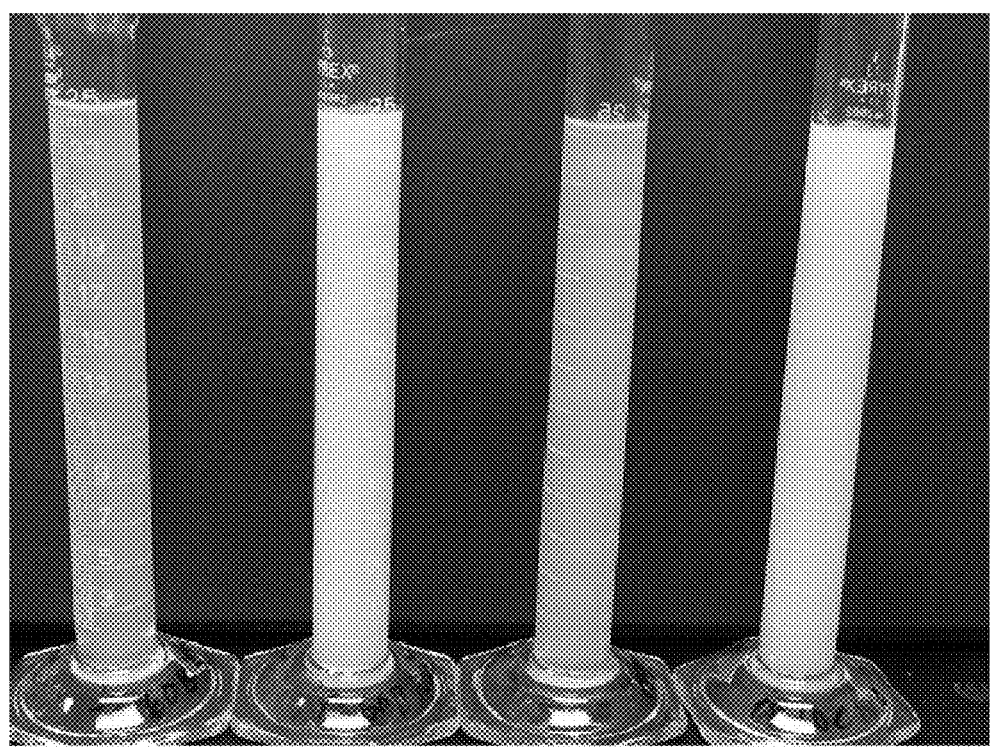
FIG. 11. Hard water tolerance data for DIACID 1550 2-Ethyl-1-hexanol (78-60B; left two cylinders) and an Industry Standard Lubricant (78-60C; right two cylinders) with the left of each diluted in 500 ppm hardness water and the right of each diluted in 1,000 ppm hardness water.
Figure 12:
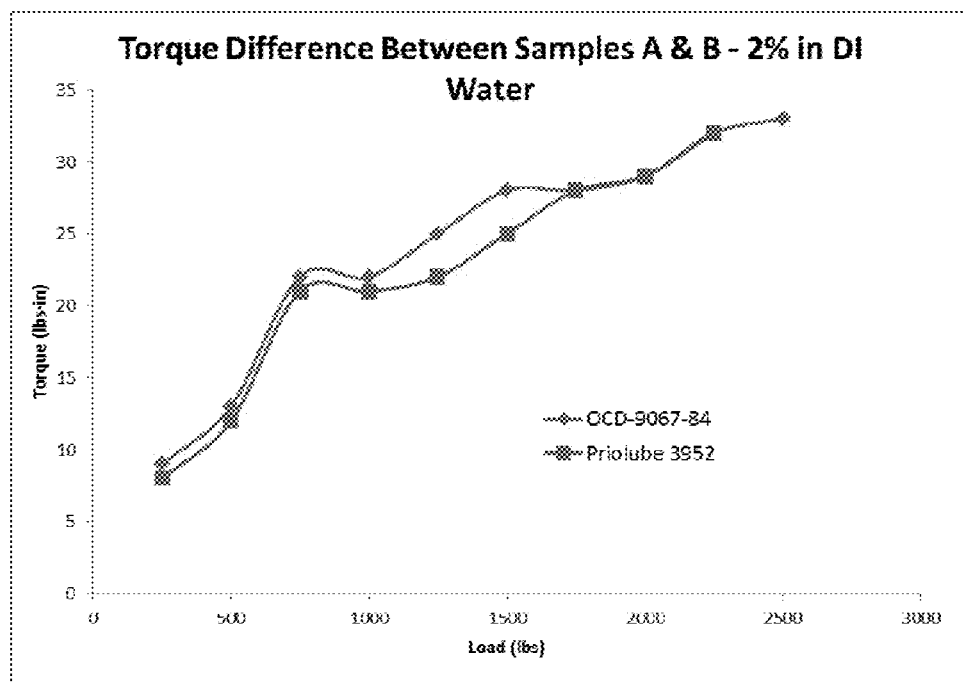
FIG. 12. Comparison of the torque during a Falex Pin Vee Block test of DIACID 1550 2-Ethyl-1-hexanol partial ester and Priolube™ 3952 containing semi-synthetic metal working fluids.
Figure 13:
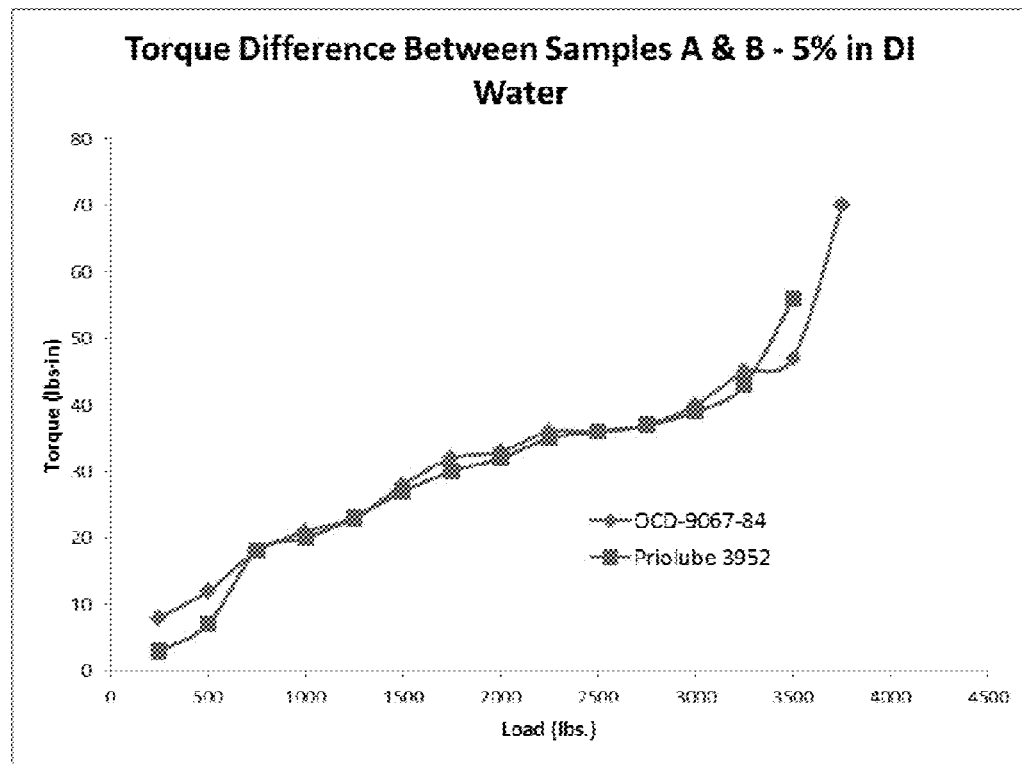
FIG. 13. Comparison of the torque during a Falex Pin Vee Block test of DIACID 1550 2-Ethyl-1-hexanol partial ester and Priolube™ 3952 containing semi-synthetic metal working fluids.
Figure 14:
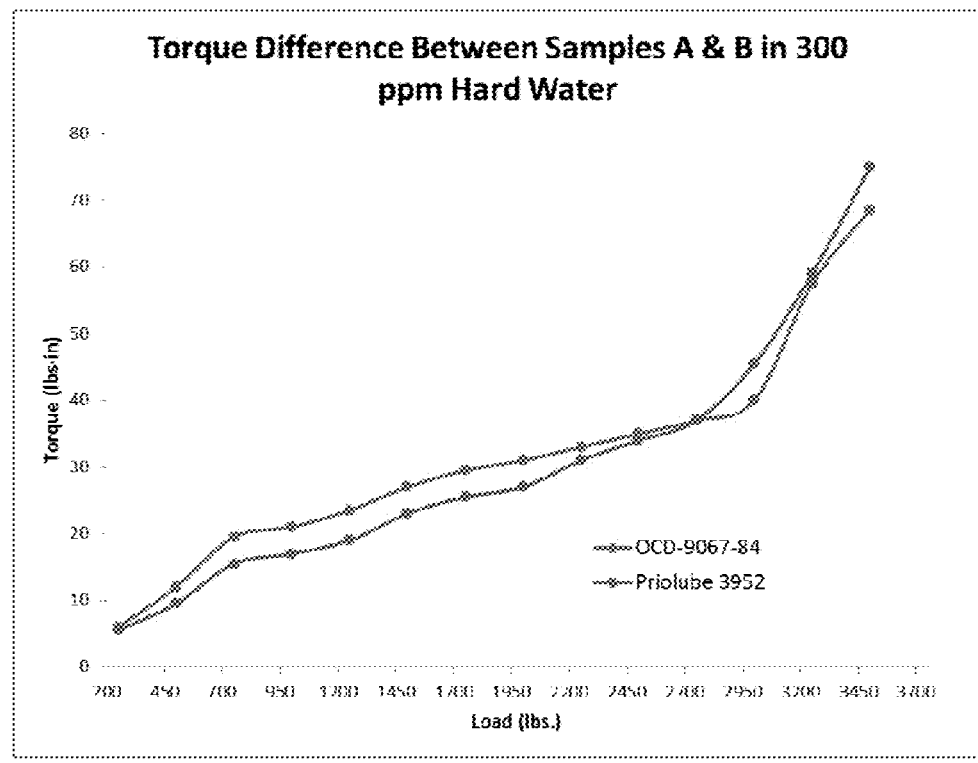
FIG. 14. Comparison of the torque during a Falex Pin Vee Block test of DIACID 1550 2-Ethyl-1-hexanol partial ester and Priolube™ 3952 containing semi-synthetic metal working fluids.
Figure 15:
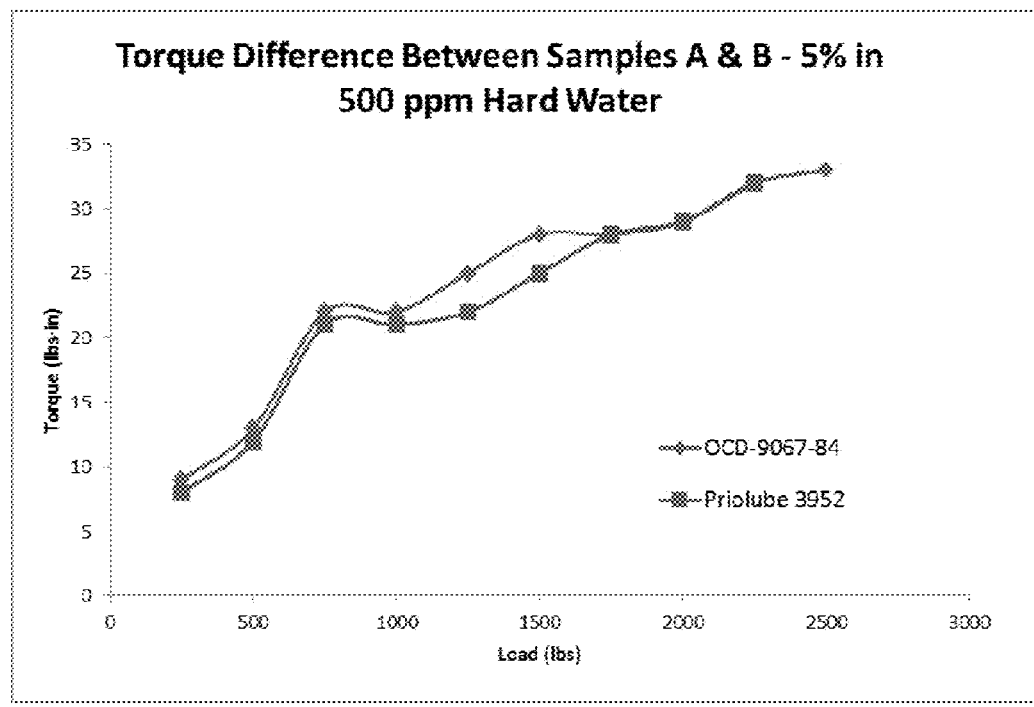
FIG. 15. Comparison of the torque during a Falex Pin Vee Block test of DIACID 1550 2-Ethyl-1-hexanol partial ester and Priolube™ 3952 containing semi-synthetic metal working fluids.

Hard water tolerance was examined with by diluting the formulas to 5% in water of varying hardness. The two samples on the left in FIG. 11 are the DIACID 1550 2-Ethylhydroxyl Semi-synthetic Metalworking Fluid formulation (78-60B) and the two on the right are the Industry Standard Lubricant Metalworking Fluid formulation (78-60C). The translucent dilutions are 500 ppm hardness water, the opaque solutions are 1000 ppm hardness water. These formulas show no variation in their degree of hard water tolerance, both are still stable emulsions at 1000 ppm hardness.

Emulsion stability was examined by heating the formulation concentrates to 120° C. for 4 hours, cooled to 0° C. for 4 hours, and then allowed to return to room temperature. At each stage these formulations were observed to be equally stable, indicating that the balance of emulsifier to oil and water is stable in both formulations. Neither formula exhibited better emulsion stability than the other.

These tests demonstrate that Industry Standard Lubricant Semi-synthetic Metalworking Fluid (78-60C) and the DIACID 1550 2-Ethylhydroxyl Semi Synthetic Metalworking Fluid (78-60B) have similar lubricating abilities. These tests indicate that the two formulas have similar characteristics with regard to corrosion protection properties, and emulsion and hard water stability. Formula Industry Standard Lubricant Semi-synthetic Metalworking Fluid (78-60C) has 3% better lubrication in the microtap torque test using steel than DIACID 1550 2-Ethylhydroxyl Semi Synthetic Metalworking Fluid (78-60B), though this difference is minor. Furthermore, there is not a statistically significant difference between these lubricants in the microtap test tapping aluminum alloy. It was observed that DIACID 1550 2-Ethylhydroxyl Semi-synthetic Metalworking Fluid (78-60B) had faster foam dissipation in the shake test than the Industry Standard Lubricant Semi-synthetic Metalworking Fluid (78-60C).

Comparison of Semi-synthetic Metalworking Fluids Containing Either DIACID 1550 2-Ethyl-1-hexanol Half Ester or Priolube™ 3952. The Semi-synthetic metalworking fluid formulations are shown in Table 37.

TABLE 37

Semi-synthetic Metalworking Fluid Formulations

| | DIACID 1550 2-Ethylhexly Partial Ester Semi-Synthetic Metalworking Fluid Formulation | Priolube 3952 ™ Semi-Synthetic Metalworking Fluid Formulation |
|---|---|---|
| Hydrocal 100 (100 SUS Naphthenic Oil) | 20.0 | 20.0 |
| Polartech ® EA ™ 646 | 7.5 | 7.5 |
| M28 (tall oil fatty acid) | 3.0 | 3.0 |
| Test Lubricant | 5.0 (DIACID 1550 2-Ethylhexyl Partial Ester) | 5.0 (Croda Priolube ™ 3952 - Self-emulsifying ester) |
| Emulsogen M-A (fatty alcohol ethoxylate) | 3.5 | |
| ANTAROX ® RA-40 (fatty alcohol ethoxylate/propoxylate) | 2.0 | 2.0 |
| DIACID 1550 | 1.0 | 1.0 |
| Polyphase FX-40 (fungicide) | 1.0 | 1.0 |
| DIGLYCOLAMINE ® | 5.0 | 5.0 |
| Triethanolamine, 85% | 5.0 | 5.0 |
| AQUALOX ™ 232 (corrosion inhibitor) | 6.0 | 6.0 |
| CORRGUARD ® EXT (bioresistant amine/coupler) | 0.75 | 0.75 |
| Deionized Water | 38.15 | 38.15 |
| CONTRAM ™ ST-1 (bactericide) | 2.0 | 2.0 |
| FOAM BAN ® HP-753 (defoamer) | 0.1 | 0.1 |

The 100 SUS naphthenic oil Hydrocal 100 was acquired from Calumet Refining (Calumet Specialty Products Partners, L.P., 2780 Waterfront Pkwy. E. Dr. Suite 200, Indianapolis, Ind. 46214, USA). The 460 molecular weight, medium molecular weight, natural sodium petroleum sulfonate Polartech® EA™ 646 was acquired from Afton® Chemical (Afton® Chemical, 500 Spring Street, Richmond, Va., 23219, USA). Tall oil fatty acid M-28 was acquired from Ingevity (Ingevity, S.C.). Fatty alcohol ethoylate emulsifier Emulsogen M-A was acquired from Clariant (Clariant SE, Rothausstrasse 61, 4132 Muttenz 1, Switzerland). Fatty alcohol/propoxylate ANTAROX® RA-40 was acquired from Solvay (Solvay, 3333 Richmond Avenue, Houston, Tex. 77098, USA) or Rhodia (Immeuble Coeur Defense, Tour A, 37eme etage, 110 esplanade Charles de Gaulle, Courbevoie, Île-de-France, France). DIACID 1550 was acquired from Ingevity (Ingevity, S.C.). Fungicide Polyphase FX-40 (IPBC-iodopropynylbutyl-carbamate) was acquired from Troy (Troy Corporation, 8 Vreeland Road, PO Box 955, Florham Park, N.J., 07932 USA). DIGLY-COLAMINE® was acquired from Huntsman (Huntsman Corporation, 10003 Woodlock Forest Dr. The Woodlands, Tex. 77380, USA). Triethanolamine (85%) was acquired from Dow™ Chemical (Dow™ Chemical, 2030 Dow Center, Midland, Mich. 48674, USA), 15% present in water. Corrosion inhibitor AQUALOX™ 232 was acquired from Lubrizol (The Lubrizol Corporation, 24900Lakeland Boulevard, Wickliffe, Ohio 44092, USA), which is based on INVISTA CORFREE® M1 and MEA/TEA. Bioresistant amine/coupler CORRGUARD® EXT was acquired from ANGUS® Chemical (ANGUS® Chemical, 1500 E Lake Cook Rd, Buffalo Grove, Ill. 60089, USA). Bactericide CONTRAM™ ST-1 (methylenebismorpholine) was acquired from Lubrizol (The Lubrizol Corporation, 24900 Lakeland Boulevard, Wickliffe, Ohio 44092, USA). Defoamer FOAM BAN® HP-753 was acquired from Münzing (MUNZING CHEMIE GmbH, Münzingstrasse 2, 74232 Abstatt, Germany).

The components found in Table 37 were added in the order in which they are found in the table. The 100 SUS naphthenic oil was added to a beaker with a magnetic stirrer. The agitator was turned on and the oil heated to a temperature slightly above room temperature (40-45° C.). In larger batches, for example in a 5 gallon drum, the 100 SUS naphthenic oil was preheated. Sodium sulfonate was warmed to about 50° C. in an oven. The hot sodium sulfonate was then added to the naphthenic oil while the agitation continued. The sodium sulfonate is quite viscous, so the heat was used to enable the sodium sulfonate to more quickly dissolve in the naphthenic oil.

The remaining ingredients were added in the order provided in Table 37 without the use of any heat and assuring uniform dispersal prior to the addition of the next ingredient. In some embodiments, the defoamer was not utilized. Examination of the formulations is shown in Table 38.

TABLE 38

| Parameter | Result |
| --- | --- |
| Appearance | Clear Amber Liquid |
| Odor | Characteristic Amine |
| pH, 5% (deionized water) | 9.35 |
| Specific Gravity, 60/60 F | 0.997 |
| Density - lbs/gallon | 8.32 |
| 5 Day Low Temperature Stability Testing (0° C. to −2° C.) | Remained Homogeneous |
| 5 Day High Temperature Stability Testing (40° C.) | Remained Homogeneous |

Comparison of the DIACID 1550 2-Ethyl-1-hexanol partial ester and the Priolube™ 3952 containing semi-synthetic metal working fluids are shown in FIGS. 12-15.

Exemplary Method of Producing DIACID 1550 2-Ethylhexanol Partial Ester. DIACID 1550 and 2-Ethylhexanol were reacted at a 2:1 mole ratio. Hypophosphourous acid was used as catalyst (0.25 wt % of Diacid). The reaction and the resultant products are shown below.

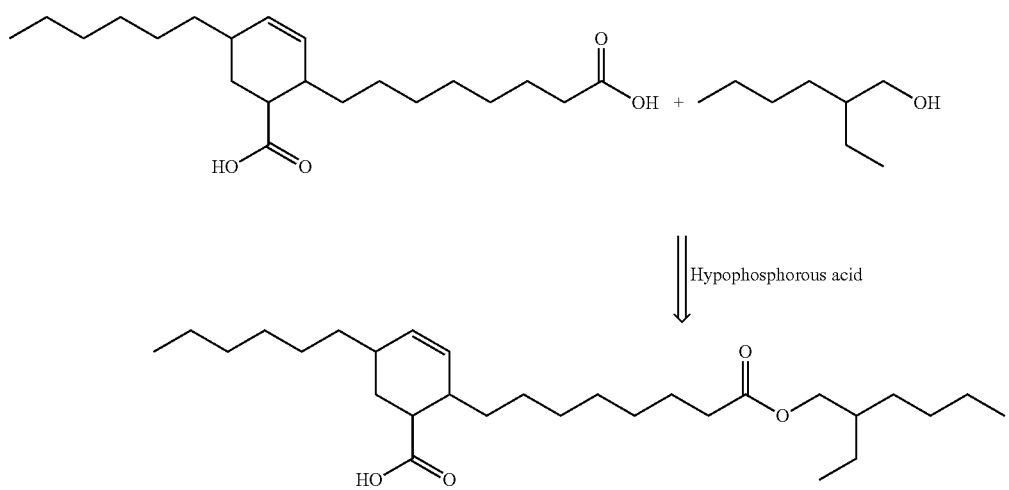

Four batches of DIACID 1550 were analyzed by non-polar GC to determine the differences of C18 monounsaturated acid percentage then used to prepare DIACID 1550 2-Ethylhexanol Partial Ester to examine the variability of the final product specifications. These results are shown in Table 39.

TABLE 39

Batch Rest Results for DIACID 1550 2-Ethylhexanol Partial Ester

| Diacid 1550 | Acid Number | C18 monounsat. % | Partial Ester AN | Partial Ester Color |
| --- | --- | --- | --- | --- |
| Old | 270.27 | 8.1 | 112.25 | 6.6 |
| Mar. 31, 2015 | 270.20 | 7.4 | 108.40 | 6.9 |
| Apr. 20, 2015 | 278.24 | 8.4 | 112.77 | 6.7 |
| May 19, 2015 | 263.41 | 4.4 | 111.4 | 6.5 |

The results demonstrate that various starting DIACID 1550 have little effects on the final partial ester products. Each of the partial esters derived from different batches of DIACID 1550 have similar acid number and color on the Gardner Color Scale (Standard Test Method for Color of Transparent Liquids (Gardner Color Scale) (ASTM D1544-04 (2010)).

As described herein, the description provides a lubricating fluid composition comprising a partial (i.e., half) ester of a compound derived from the Diels-Alder reaction of a conjugated fatty acid and an acid precursor dienophile. In any of the aspects or embodiments, the acid precursor dienophile is an acrylic acid or acrylic acid ester. In any of the aspects or embodiments, acid precursor dienophile is at least one of methacrylic acid, maleic anhydride, fumaric acid, a fumaric acid mono or diester or a combination thereof. In any of the aspects or embodiments, the conjugated fatty acid is derived from tall oil fatty acid. In any of the aspects or embodiments, the conjugated fatty acid is linoleic acid. In any of the aspects or embodiments, the compound derived from the Diels-Alder reaction of a conjugated fatty acid and acrylic acid is DIACID 1550, and the partial ester is a DIACID 1550 partial ester. In any of the aspects or embodiments, the DIACID 1550 partial ester is derived from an esterification reaction comprising an alcohol and DIACID 1550, and wherein the reaction comprises a molar excess of carboxyl moieties. In any of the described aspects or embodiments, the alcohol is selected from the group consisting of n-pentanol, 1-docecanol, 2-ethyl-1-hexanol, and combinations thereof. In any of the described aspects or embodiments, the reaction further comprises a catalyst. In any of the described aspects or embodiments, the catalyst is hypophosphourous acid.

Additionally, the description provides an aqueous metalworking composition comprising an effective amount of a lubricating compound as described herein. In any of the described aspects or embodiments, the composition comprises an effective amount of the DIACID 1550 partial ester to reduce or inhibit foaming as compared to DIACID 1550 or DIACID 1550 bis-ester alone. In any of the described aspects or embodiments, the composition comprises a semi-synthetic metalworking fluid or a full-synthetic metalworking fluid. In any of the described aspects or embodiments, the metalworking composition is a semi-synthetic metalworking fluid and further includes a coupling solvent. In any of the described aspects or embodiments, the coupling solvent is a glycol ether. In any of the described aspects or embodiments, the glycol ether is tripropylene glycol methyl ether or diethylene glycol monobutyl ether. In any of the described aspects or embodiments, the metalworking composition is a synthetic metalworking fluid and further includes a nonionic surfactant. In any of the described aspects or embodiments, the nonionic surfactant is at least one of a alkylphenol ethoxylate, a linear alcohol ethoxylate, or a DIACID 1550 ethoxylate. In any of the described aspects or embodiments, the alkylphenol ethoxylate is at least one of nonyl phenol ethoxylate and octylphenol ethoxylate. In any of the described aspects or embodiments, the linear alcohol ethoxylate is at least one of: tall oil fatty acid ethoxylate, TERGITOL™ NP-4, TERGITOL™ NP-7, and TERGITOL™ NP-9. In any of the described aspects or embodiments, the DIACID 1550 ethoxylate is at least one of: OCD-383 and OCD-384. In any of the described aspects or embodiments, the metalworking fluid comprises at least one of a biocide and a fungicide.

The description also provides a method of lubricating a metal workpiece by applying the aqueous metalworking composition as described in any of the aspects or embodiments described herein to the metal workpiece.

The description also provides a metalworking process comprising performing a metalworking operation by flushing, spraying, high pressure spraying, brushing, flowing, fluting, roll coating, immersion, or any combination thereof with the aqueous metalworking composition as described in any of the aspects or embodiments.

In certain aspects, the description provides compound having the structure:

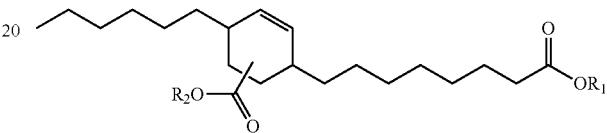

wherein $R_1$ and $R_2$ are independently selected from the group comprising H, alkyl, alkenyl, cycloalkyl, chloroalkyl, chlorocycloalkyl, polyoxyethylene, polyoxypropylene, or a mixture thereof, and wherein at least one of $R_1$ or $R_2$ but not both is H and the other is not. In any of the aspects or embodiments described herein, at least one of $R_1$ or $R_2$ but not both is at least one of alkyl, alkenyl, cycloalkyl, chloroalkyl, chlorocycloalkyl, polyoxyethylene and polyoxypropylene. In any of the aspects or embodiments described herein, the composition comprises the compound wherein at least 10 mol % of $R_1$ and $R_2$ is H. In any of the aspects or embodiments described herein, the composition comprises the compound wherein up to 90 mol % of $R_1$ and $R_2$ are at least one of alkyl, alkenyl, cycloalkyl, chloroalkyl, chlorocycloalkyl, polyoxyethylene and polyoxypropylene.

In certain embodiments, the compound has the structure:

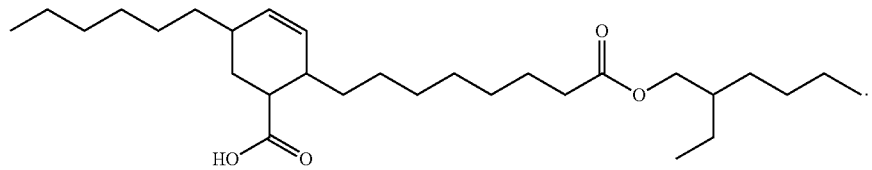 [SMILES: CCCCCCC1C=CC(CCCCCCCC(=O)OCC(CC)CCCC)C(C(=O)O)C1]

As would be understood by those of skill in the art, certain quantities, amounts, and measurements are subject to theoretical and/or practical limitations in precision, which are inherent to some of the instruments and/or methods. Therefore, unless otherwise indicated, it is contemplated that claimed amounts encompass a reasonable amount of variation.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. A lubricating composition comprising a partial or half-ester of DIACID 1550 according to the structure:

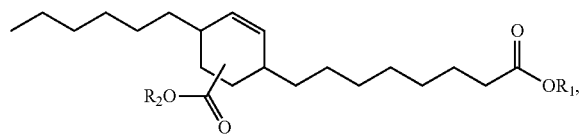

wherein the partial ester is derived from an esterification reaction at $R_1$ or $R_2$ with an alcohol selected from the group consisting of n-pentanol, 1-docecanol, 2-ethyl-1-hexanol, and combinations thereof, and wherein at least one of $R_1$ or $R_2$ but not both is H.

2. The lubricating composition of claim 1, wherein the composition comprises an effective amount of the DIACID 1550 partial ester to reduce or inhibit foaming as compared to a composition comprising the same amount of a diacid having the structure

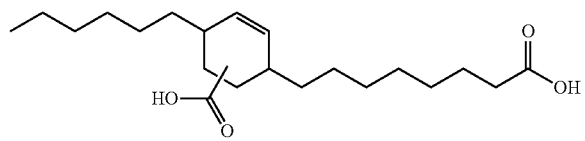

or a diester thereof.

3. The lubricating composition of claim 1, wherein the composition comprises a semi-synthetic metalworking fluid or a full-synthetic metalworking fluid.

4. An aqueous metalworking composition comprising a metal working fluid and an effective amount of a DIACID 1550 partial ester according to the structure:

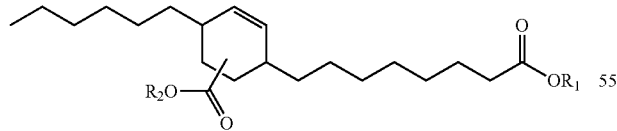

wherein the partial ester is derived from an esterification reaction at $R_1$ or $R_2$ with an alcohol selected from the group consisting of n-pentanol, 1-docecanol, 2-ethyl-1-hexanol, and combinations thereof, and wherein at least one of $R_1$ or $R_2$ but not both is H.

5. The metalworking composition of claim 4, wherein the metalworking composition comprises a semi-synthetic metal working fluid or a synthetic metal working fluid.

6. The metalworking composition of claim 5, wherein the metalworking composition is a semi-synthetic metalworking fluid and further includes a coupling solvent.

7. The metalworking composition of claim 6, wherein the coupling solvent is a glycol ether.

8. The metalworking composition of claim 7, wherein the glycol ether is tripropylene glycol methyl ether or diethylene glycol monobutyl ether.

9. The metalworking composition of claim 4, wherein the metalworking composition and further includes a nonionic surfactant.

10. The metalworking composition of claim 9, wherein the nonionic surfactant is at least one of a alkylphenol ethoxylate, a linear alcohol ethoxylate, or an ethoxylate of a diacid having the structure

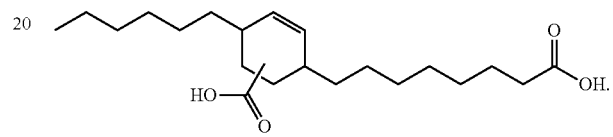

11. The metalworking composition of claim 10, wherein the alkylphenol ethoxylate is at least one of nonyl phenol ethoxylate and octylphenol ethoxylate.

12. The metalworking composition of claim 10, wherein the linear alcohol ethoxylate is at least one of: tall oil fatty acid ethoxylate, and nonylephenol ethoxylate.

13. The metalworking composition of claim 4, further comprising at least one of a biocide and a fungicide.

14. A method of lubricating a metal workpiece by applying the aqueous metalworking composition of claim 4 to the metal workpiece.

15. A metalworking process comprising performing a metalworking operation by flushing, spraying, high pressure spraying, brushing, flowing, fluting, roll coating, immersion, or any combination thereof with the aqueous metalworking composition of claim 4.

16. A compound having the structure:

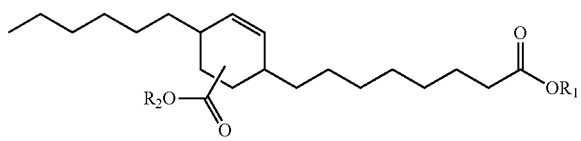

wherein $R_1$ and $R_2$ are independently selected from the group comprising H, alkyl, alkenyl, cycloalkyl, chloroalkyl, chlorocycloalkyl, polyoxyethylene, polyoxypropylene, or a mixture thereof, and wherein at least one of $R_1$ or $R_2$ but not both is H.

17. The compound of claim 16, wherein at least one of $R_1$ or $R_2$ but not both is at least one of alkyl, alkenyl, cycloalkyl, chloroalkyl, chlorocycloalkyl, polyoxyethylene and polyoxypropylene.

18. The compound of claim 17, wherein the compound has the structure:

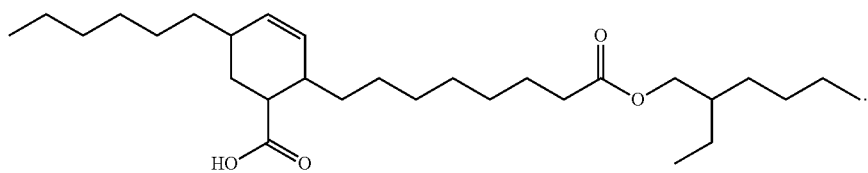 [SMILES: CCCCCCC1C=CC(CCCCCCCC(=O)OCC(CC)CCCC)C(C(=O)O)C1]
19. A composition comprising the compound of claim 16, wherein at least 10 mol % of $R_1$ and $R_2$ is H.
20. The composition of claim 19, wherein up to 90 mol % of $R_1$ and $R_2$ are at least one of alkyl, alkenyl, cycloalkyl, chloroalkyl, chlorocycloalkyl, polyoxyethylene and polyoxypropylene.
* * * * *